US011725230B2

(12) United States Patent
Makrigiorgos et al.

(10) Patent No.: US 11,725,230 B2
(45) Date of Patent: Aug. 15, 2023

(54) SELECTIVE DEGRADATION OF WILD-TYPE DNA AND ENRICHMENT OF MUTANT ALLELES USING NUCLEASE

(71) Applicant: Dana-Farber Cancer Institute, Inc., Boston, MA (US)

(72) Inventors: Gerassimos Makrigiorgos, Chestnut Hill, MA (US); Chen Song, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 871 days.

(21) Appl. No.: 15/739,301

(22) PCT Filed: Jun. 24, 2016

(86) PCT No.: PCT/US2016/039167
§ 371 (c)(1),
(2) Date: Dec. 22, 2017

(87) PCT Pub. No.: WO2016/210224
PCT Pub. Date: Dec. 29, 2016

(65) Prior Publication Data
US 2018/0187242 A1 Jul. 5, 2018

Related U.S. Application Data

(60) Provisional application No. 62/183,854, filed on Jun. 24, 2015.

(51) Int. Cl.
*C12Q 1/68* (2018.01)
*C12Q 1/6806* (2018.01)
*C12P 19/34* (2006.01)
*C12N 15/10* (2006.01)
*C12N 9/22* (2006.01)
*C12Q 1/6883* (2018.01)
*C12N 9/00* (2006.01)
*C07H 21/04* (2006.01)

(52) U.S. Cl.
CPC .......... *C12Q 1/6806* (2013.01); *C12N 9/22* (2013.01); *C12N 15/10* (2013.01); *C12N 15/1093* (2013.01); *C12P 19/34* (2013.01); *C12Q 1/68* (2013.01); *C12Q 1/6883* (2013.01)

(58) Field of Classification Search
None
See application file for complete search history.

(56) References Cited

U.S. PATENT DOCUMENTS

| | | | |
|---|---|---|---|
| 5,656,461 A | 8/1997 | Demers | |
| 5,670,316 A | 9/1997 | Calhoun et al. | |
| 7,435,794 B2* | 10/2008 | Lukyanov | C07K 16/40 435/6.1 |
| 8,440,404 B2 | 5/2013 | Makarov et al. | |
| 10,913,977 B2 | 2/2021 | Makrigiorgos | |
| 11,030,992 B2 | 9/2021 | Makrigiorgos | |
| 11,174,510 B2 | 11/2021 | Makrigiorgos | |
| 11,371,090 B2 | 6/2022 | Makrigiorgos | |
| 2004/0121319 A9* | 6/2004 | Hillis | C12Q 1/6874 702/20 |
| 2006/0057569 A1 | 3/2006 | Charle | |
| 2008/0254453 A1 | 10/2008 | Shapero et al. | |
| 2009/0053698 A1 | 2/2009 | Hayashida | |
| 2009/0068652 A1 | 3/2009 | Taylor et al. | |
| 2009/0099075 A1* | 4/2009 | Barg | A61Q 19/08 435/252.8 |
| 2009/0148842 A1 | 6/2009 | Gormley et al. | |
| 2010/0216648 A1* | 8/2010 | Staehler | C12Q 1/6869 435/6.12 |
| 2012/0237943 A1* | 9/2012 | Soldatov | C12Q 1/6853 435/6.19 |
| 2013/0059734 A1 | 3/2013 | Molloy et al. | |
| 2013/0303385 A1* | 11/2013 | Korlach | C12Q 1/6827 506/4 |
| 2014/0051087 A1 | 2/2014 | Makrigiorgos | |
| 2014/0315726 A1 | 10/2014 | Beatty et al. | |
| 2015/0147760 A1 | 5/2015 | Gupta et al. | |
| 2020/0040388 A1 | 2/2020 | Makrigiorgos et al. | |
| 2022/0290209 A1 | 9/2022 | Makrigiorgos | |

FOREIGN PATENT DOCUMENTS

| | | |
|---|---|---|
| JP | 6-510201 A | 11/1994 |
| JP | 2005-536983 A | 12/2005 |
| JP | 2012-165755 A | 9/2012 |

(Continued)

OTHER PUBLICATIONS

Gu et al., "Depletion of Abundant Sequences by Hybridization (DASH): using Cas9 to remove unwanted high-abundance species in sequencing libraries and molecular counting applications", Genome Biology, 17:41. (Year: 2016).*
Gu et al., "Depletion of Abundant Sequences by Hybridization (DASH): using Cas9 to remove unwanted high-abundance species in sequencing libraries and molecular counting applications", Genome Biology, (2016) 17:41. (Year: 2016).*
International Search Report and Written Opinion dated Sep. 26, 2016 for Application No. PCT/US2016/039167.
International Preliminary Report on Patentability dated Jan. 4, 2018 for Application No. PCT/US2016/039167.
Castellanos-Rizaldos et al., COLD-PCR amplification of bisulfite-converted DNA allows the enrichment and sequencing of rare un-methylated genomic regions. PLoS One. Apr. 11, 2014;9(4):e94103. doi: 10.1371/journal.pone.0094103. eCollection 2014.

(Continued)

*Primary Examiner* — Bradley L. Sisson
(74) *Attorney, Agent, or Firm* — Wolf, Greenfield & Sacks, P.C.

(57) ABSTRACT

The present disclosure provides methods for preparing a target mutant nucleic acid for subsequent enrichment relative to a wild type nucleic acid using nucleases that have a substantially higher activity on double stranded DNA versus single stranded DNA or RNA. The present disclosure also includes methods for enriching a target mutant nucleic acid and for preparing unmethylated/methylated nucleic acids of interest for subsequent enrichment.

20 Claims, 22 Drawing Sheets

(56) References Cited

FOREIGN PATENT DOCUMENTS

| WO | WO-9402643 A1 * | 2/1994 | ........ C12Q 1/6813 |
|---|---|---|---|
| WO | WO 2007/087310 A2 | 8/2007 | |
| WO | WO 2012/129363 A2 | 9/2012 | |
| WO | WO-2012135053 A2 * | 10/2012 | ........ C12Q 1/6858 |
| WO | WO 2012/159089 A1 | 11/2012 | |
| WO | WO 2014/142261 A1 | 9/2014 | |
| WO | WO 2015/013166 A1 | 1/2015 | |
| WO | WO 2015/100427 A1 | 7/2015 | |
| WO | WO 2016/210224 A1 | 12/2016 | |

OTHER PUBLICATIONS

Castellanos-Rizaldos et al., Temperature-tolerant COLD-PCR reduces temperature stringency and enables robust mutation enrichment. Clin Chem. Jul. 2012;58(7):1130-8. doi: 10.1373/clinchem.2012.183095. Epub May 15, 2012.

Chou et al., A comparison of high-resolution melting analysis with denaturing high-performance liquid chromatography for mutation scanning: cystic fibrosis transmembrane conductance regulator gene as a model. Am J Clin Pathol. Sep. 2005;124(3):330-8.

Diehl et al., Detection and quantification of mutations in the plasma of patients with colorectal tumors. Proc Natl Acad Sci U S A. Nov. 8, 2005;102(45):16368-73. Epub Oct. 28, 2005.

Engelman et al., Allelic dilution obscures detection of a biologically significant resistance mutation in EGFR-amplified lung cancer. J Clin Invest. Oct. 2006;116(10):2695-706. Epub Aug. 10, 2006.

Gao et al., DNA-guided genome editing using the Natronobacterium gregoryi Argonaute. Nat Biotechnol. Jul. 2016;34(7):768-73. doi: 10.1038/nbt.3547. Epub May 2, 2016.

Gao et al., Retraction: DNA-guided genome editing using the Natronobacterium gregoryi Argonaute. Nat Biotechnol. Aug. 8, 2017;35(8):797. doi: 10.1038/nbt0817-797a.

Gu et al., Depletion of Abundant Sequences by Hybridization (DASH): using Cas9 to remove unwanted high-abundance species in sequencing libraries and molecular counting applications. Genome Biol. Mar. 4, 2016;17:41. doi: 10.1186/s13059-016-0904-5.

Ito et al., Tet proteins can convert 5-methylcytosine to 5-formylcytosine and 5-carboxylcytosine. Science. Sep. 2, 2011;333(6047):1300-3. doi: 10.1126/science.1210597. Epub Jul. 21, 2011.

Janne et al., A rapid and sensitive enzymatic method for epidermal growth factor receptor mutation screening. Clin Cancer Res. Feb. 1, 2006;12(3 Pt 1):751-8.

Kimura et al., Mutant DNA in plasma of lung cancer patients: potential for monitoring response to therapy. Ann N Y Acad Sci. Jun. 2004;1022:55-60.

Li et al., Replacing PCR with COLD-PCR enriches variant DNA sequences and redefines the sensitivity of genetic testing. Nat Med. May 2008;14(5):579-84. doi: 10.1038/nm1708. Epub Apr. 13, 2008.

Milbury et al., Ice-COLD-PCR enables rapid amplification and robust enrichment for low-abundance unknown DNA mutations. Nucleic Acids Res. Jan. 2011;39(1):e2. doi: 10.1093/nar/gkq899. Epub Oct. 11, 2010.

Murphy et al., Enriching mutant sequences by modulating the denaturation time during PCR. Clin Chem. Jul. 2014;60(7): 1014-6. doi: 10.1373/clinchem.2014.221465. Epub May 5, 2014.

Nilsen et al., The enzyme and the cDNA sequence of a thermolabile and double-strand specific DNase from Northern shrimps (Pandalus borealis). PLoS One. Apr. 22, 2010;5(4):e10295. doi: 10.1371/journal.pone.0010295.

Paez et al., EGFR mutations in lung cancer: correlation with clinical response to gefitinib therapy. Science. Jun. 4, 2004;304(5676):1497-500. Epub Apr. 29, 2004.

Qiu et al., Duplex-specific nuclease-mediated bioanalysis. Trends Biotechnol. Mar. 2015;33(3):180-8. doi: 10.1016/j.tibtech.2014.12.008. Epub Jan. 29, 2015.

Shagin et al., A novel method for SNP detection using a new duplex-specific nuclease from crab hepatopancreas. Genome Res. Dec. 2002;12(12):1935-42.

Thomas et al., High-throughput oncogene mutation profiling in human cancer. Nat Genet. Mar. 2007;39(3):347-51. Epub Feb. 11, 2007.

Thomas et al., Sensitive mutation detection in heterogeneous cancer specimens by massively parallel picoliter reactor sequencing. Nat Med. Jul. 2006;12(7):852-5. Epub Jun. 25, 2006.

Wetmur, DNA probes: applications of the principles of nucleic acid hybridization. Crit Rev Biochem Mol Biol. 1991;26(3-4):227-59.

Yu et al., Base-resolution analysis of 5-hydroxymethylcytosine in the mammalian genome. Cell. Jun. 8, 2012;149(6):1368-80. doi: 10.1016/j.cell.2012.04.027. Epub May 17, 2012.

Bacher et al., Improved Detection of Microsatellite Instability in Early Colorectal Lesions. PLoS One. Aug. 7, 2015; 10(8):e0132727. doi: 10.1371/journal.pone.0132727. eCollection 2015.

Beggs et al., A study of genomic instability in early preneoplastic colonic lesions. Oncogene. Nov. 14, 2013; 32(46):5333-7. doi: 10.1038/onc.2012.584. Epub Dec. 17, 2012.

Buhard et al., HSP110 T17 simplifies and improves the microsatellite instability testing in patients with colorectal cancer. J Med Genet. Jun. 2016; 53(6):377-84. doi: 10.1136/jmedgenet-2015-103518. Epub Feb. 1, 2016.

Chan et al., Cloning of CviPII nicking and modification system from chlorella virus NYs-1 and application of Nt. CviPII in random DNA amplification. Nucleic Acids Res. Nov. 29, 2004; 32(21):6187-99. Print 2004.

Ellegren, Microsatellites: simple sequences with complex evolution. Nat Rev Genet. Jun. 2004; 5(6):435-45.

Gan et al., Applicability of next generation sequencing technology in microsatellite instability testing. Genes (Basel). Feb. 12, 2015; 6(1):46-59. doi: 10.3390/genes6010046.

How-Kit et al., Major improvement in the detection of microsatellite instability in colorectal cancer using HSP110 T17 E-ice-COLD-PCR. HumMutat. Mar. 2018; 39(3):441-453. doi: 10.1002/humu.23379. Epub Dec. 26, 2017.

How-Kit et al., Sensitive detection of KRAS mutations using enhanced-ice-COLD-PCR mutation enrichment and direct sequence identification. Hum Mutat. Nov. 2013; 34(11): 1568-80. doi: 10.1002/humu.22427. Epub Sep. 17, 2013.

Janavicius et al., Microsatellite instability detection by high-resolution melting analysis. Clin Chem, Nov. 2010; 56(11):1750-7, doi: 10.1373/clinchem.2010.150680. Epub Sep. 17, 2010.

Ladas et al., Enhanced detection of microsatellite instability using pre-PCR elimination of wild-type DNA homo-polymers in tissue and liquid biopsies. Nucleic Acids Res. Jul. 6, 2018; 46(12):e74. doi: 10.1093/nar/gky251.

Maruvka et al., Analysis of somatic microsatellite indels identifies driver events in human tumors. Nat Biotechnol. Oct. 2017; 35(10):951-959. doi: 10.1038/nbt.3966. Epub Sep. 11, 2017.

Shaw et al., Microsatellite alterations plasma DNA of primary breast cancer patients. Clin Cancer Res. Mar. 2000; 6(3):1119-24.

Yang et al., Nucleoside analogs to manage sequence divergence in nucleic acid amplification and SNP detection. Nucleic Acids Res. Jul. 6, 2018; 46(12):5902-5910. doi: 10.1093/nar/gky392.

Zheng et al., Quantitative PCR measurements of the effects of introducing inosines into primers provides guidelines for improved degenerate primer design. J Virol Methods. Nov. 2008; 153(2):97-103. doi: 10.1016/j.jviromet.2008.07.029. Epub Sep. 17, 2008.

Extended European Search Report for Application No. EP 16815352.6, dated Oct. 16, 2018.

Castellanos-Rizaldos et al., Enhanced ratio of signals enables digital mutation scanning for rare allele detection. J MolDiagn. May 2015;17(3):284-92. doi: 10.1016/j.jmoldx.2014.12.003. Epub Mar. 13, 2015.

Cullen et al., Thermal denaturation of DNA from bromodeoxyuridine substituted cells. Nucleic Acids Res. Jan. 1976;3(1):49-62.

Milbury et al., Multiplex amplification coupled with COLD-PCR and high resolution melting enables identification of low-abundance mutations in cancer samples with low DNA content.

Song et al., Elimination of unaltered DNA in mixed clinical samples via nuclease-assisted minor-allele enrichment. Nucleic Acids Res. Nov. 2, 2016;44(19):e146. Epub Jul. 18, 2016.

EP 16815352.6, Oct. 16, 2018, Extended European Search Report.

(56) References Cited

OTHER PUBLICATIONS

International Preliminary Report on Patentability dated Mar. 3, 2022 for Application No. PCT/US2020/047098.
International Search Report and Written Opinion dated Feb. 2, 2021 for Application No. PCT/US2020/047098.
Invitation to Pay Additional Fees mailed Nov. 9, 2020 for Application No. PCT/US2020/047098.
Liu et al., Label-free optical detection of single-base mismatches by the combination of nuclease and gold nanoparticles. Biosens Bioelectron. Jul. 15, 2011;26(11):4294-300. doi: 10.1016/j.bios.2011.04.014. Epub May 5, 2011. PMID: 21605966.
Milbury et al., COLD-PCR enrichment of rare cancer mutations prior to targeted amplicon resequencing. Clin Chem. Mar. 2012;58(3):580-9. doi: 10.1373/clinchem.2011.176198. Epub Dec. 21, 2011. PMID: 22194627; PMCID: PMC3418918.
Milbury et al., PCR-based methods for the enrichment of minority alleles and mutations. Clin Chem. Apr. 2009;55(4):632-40. doi: 10.1373/clinchem.2008.113035. Epub Feb. 6, 2009. PMID: 19201784; PMCID: PMC2811432.
Ladas et al. Multiplexed Elimination of Wild-Type DNA and High-Resolution Melting Prior to Targeted Resequencing of Liquid Biopsies. Clin Chem. 2017;63(10):1605-1613. doi:10.1373/clinchem.2017.272849.
Owczarzy et al., Predicting stability of DNA duplexes in solutions containing magnesium and monovalent cations. Biochemistry. May 13, 2008;47(19):5336-53. doi: 10.1021/bi702363u. Epub Apr. 19, 2008.

\* cited by examiner

| 1 | 2 | 3 | 4 | 5 | 6 | 7 |
|---|---|---|---|---|---|---|
| Gene | | Variant | No-DSN (%) | 0.2U-DSN prod (%) | 5%-gDNA ctrl (%) | % given from HDx |
| BRAF | V600E | c.1799T>A | 11.7 | 99.8 | 6.64 | 8% |
| BRAF | V600K | c.1798_1799GT>AA | 6.29 | 97.9 | 2.78 | 4% |
| EGFR | T790M | c.2369C>T | 7.15 | 69.1 | 3.84 | 4.2% |
| FLT3 | ΔI836 | c.2506_2508delATC | 7.18 | 99.9 | 6.13 | 5% |
| IDH1 | R132C | c.394C>T | 7.75 | 99.3 | 5.62 | 5% |
| JAK2 | V617F | c.1849G>T | 8.33 | 69.4 | 5.21 | 5% |
| KRAS | G12A | c.35G>C | 7.05 | 21.3 | 4.41 | 5% |
| KRAS | G12R | c.34G>C | 7.94 | 16.6 | 14 | 5% |
| MEK1 | P124L | c.371C>T | 6.18 | 95.5 | 5.04 | 5% |
| NOTCH1 | L1601P | c.4799T>C | 10 | 64 | 9.55 | 4.80% |
| NRAS | Q61K | c.181C>A | 8.98 | 78.3 | 5.45 | 5% |

FIG. 7B

SELECTIVE DEGRADATION OF WILD-TYPE DNA AND ENRICHMENT OF MUTANT ALLELES USING NUCLEASE

RELATED APPLICATIONS

This application is a national stage of International application number PCT/US2016/039167, filed Jun. 24, 2016, which claims priority under 35 U.S.C. § 119(e) to U.S. provisional application No. 62/183,854, filed Jun. 24, 2015, the contents of both of which are incorporated herein by reference in their entirety.

GOVERNMENT SUPPORT

This invention was made with government support under grant number R21 CA175542 awarded by The National Institutes of Health. The government has certain rights in the invention.

BACKGROUND OF THE INVENTION

A commonly encountered situation in genetic analysis entails the need to identify a low percent of variant DNA sequences ('minority alleles') in the presence of a large excess of non-variant sequences ('majority alleles'). Examples for such situations include the following: identification and sequencing of a few mutated alleles in the presence of a large excess of normal (wild-type) alleles, a commonly encountered situation in cancer (for example, identification of tumor-circulating DNA in blood or in urine of cancer patients (or abnormal DNA in people suspected of having cancer) in the presence of a large excess of wild type alleles); identification of a few methylated alleles in the presence of a large excess of unmethylated alleles (or vice-versa) in epigenetic analysis; identification and genotyping of a few fetal DNA sequences circulating in the maternal blood where a large excess of maternal DNA sequences are also present; identification of emerging mutated strains in infectious agents (bacteria or viruses); and variant sequence detection for crop development.

While reliable high throughput screening methods for germline or high-prevalence somatic mutations have been described, detection of low-prevalence somatic mutations in tumors with heterogeneity, stromal contamination, or in bodily fluids is still problematic. And yet, the clinical significance of identifying these mutations is very important in several situations. For example, in lung adenocarcinoma, low-level EGFR mutations that cannot be identified by regular sequencing can confer positive response to tyrosine kinase inhibitors or drug resistance. Mutations in plasma useful as biomarkers for early detection of cancer or cancer response to treatment, cannot be sequenced using conventional methods due to the high excess of wild type alleles originating from normal tissues. Additionally, mutations in tumors with frequent stromal contamination, such as pancreatic or prostate cancer, can be 'masked' by presence of wild type alleles, thus requiring laborious micro-dissection or resulting in missing mutations altogether.

Beyond cancer, low levels of target DNA in the presence of high levels of non-target DNA occurs in many other fields and applications. For example, the detection of a small amount of fetal alleles within maternal alleles is especially important for prenatal diagnosis during early stages in pregnancy where fetal alleles comprise a low fraction. An especially interesting application to this end is the fact that fetal alleles are substantially hypomethylated compared to maternal alleles. Thus, there is a general need to develop techniques that allow for identification of low level minority alleles (for example, mutated or hypo/hypermethylated alleles) in the presence of high level non-variant majority alleles.

SUMMARY OF THE INVENTION

The present disclosure relates to a novel development ( Nuclease-assisted Mutation Enrichment, NaME) that results to preferential cleavage of wild type nucleic acids, thereby allowing for subsequent enrichment of mutated target sequences of interest. The mutation-enriched sequences can then be screened using any currently available methods for identifying mutations, such as Sanger Sequencing, high resolution melting (HRM), etc.

Accordingly, some aspects of the disclosure provide a method for preparing a target mutant nucleic acid for subsequent enrichment relative to a wild type nucleic acid. The method comprises subjecting a nucleic acid sample comprising a double-stranded wild type nucleic acid and a double-stranded target nucleic acid suspected of containing a mutation to a condition that destabilizes the double stranded wild type and target mutant nucleic acids; contacting the destabilized double stranded wild type and target mutant nucleic acids with a pair of oligonucleotide probes, one of which is complimentary to the wild type nucleic acid top strand and the other is complimentary to the wild type nucleic acid bottom strand, to permit hybridization of the probes to their corresponding sequences on the wild type and target mutant nucleic acids thereby forming complimentary wild-type-probe duplexes on top and bottom strands, and partially complimentary target mutant-probe duplexes, wherein at least one of the probes overlaps a sequence on the target nucleic acid containing the suspected mutation; and exposing the complimentary wild-type-probe duplexes and the partially complimentary target mutant-probe duplexes to a double strand-specific nuclease (DSN), wherein the DSN cleaves the complimentary wild type-probe duplexes but not the partially complimentary target mutant-probe duplexes.

Some aspects of the disclosure provide a method for preparing a target mutant nucleic acid for subsequent enrichment relative to a wild type nucleic acid comprising exposing a nucleic acid sample comprising a double-stranded wild type nucleic acid and a double-stranded target nucleic acid suspected of containing a mutation to a double strand-specific nuclease (DSN) and a pair of oligonucleotide probes, one of which is complimentary to the wild type nucleic acid top strand and the other is complimentary to the wild type nucleic acid bottom strand, to create a reaction mixture, wherein at least one of the probes overlaps a sequence on the target nucleic acid containing the suspected mutation; and subjecting the reaction mixture to a condition that destabilizes the double stranded wild type and target mutant nucleic acids to permit hybridization of the probes to their corresponding sequences on the wild type and target mutant nucleic acids thereby forming complimentary wild-type-probe duplexes on top and bottom strands, and partially complimentary target mutant-probe duplexes, wherein the DSN cleaves the complimentary wild type-probe duplexes but not the partially complimentary target mutant-probe duplexes.

In some embodiments, the condition that destabilizes the double stranded wild type and mutant nucleic acids to permit hybridization of the probes to their corresponding sequences on the wild type and mutant nucleic acids comprises addition of an organic solvent and/or an increase in temperature combined with a thermostable DSN.

Some aspects of the disclosure provide a method for preparing a target mutant nucleic acid for subsequent enrichment relative to a wild type nucleic acid comprising exposing a nucleic acid sample comprising a double-stranded wild type nucleic acid and a double-stranded target nucleic acid suspected of containing a mutation to a pair of oligonucleotide probes, one of which is complimentary to the wild type nucleic acid top strand and the other is complimentary to the wild type nucleic acid bottom strand, to create a reaction mixture, wherein at least one of the probes overlaps a sequence on the target nucleic acid containing the suspected mutation; subjecting the reaction mixture to a denaturing temperature to permit denaturation of the wild type nucleic acid and the target mutant nucleic acid; reducing the temperature of the reaction mixture to permit formation of complimentary wild type-probe duplexes on top and bottom strands and partially complimentary target mutant-probe duplexes; and exposing the reaction mixture to a double strand-specific nuclease (DSN), wherein the DSN cleaves the complimentary wild type-probe duplexes but not the partially complimentary target mutant-probe duplexes.

In some embodiments, the method is used to prepare an unmethylated target nucleic acid of interest for subsequent enrichment, and wherein prior to implementing the NaME protocol described herein on the reaction mixture, the nucleic acid sample is treated with sodium bisulfite and one of the oligonucleotide probes is complimentary to top strand of the methylated nucleic acid of interest, while the other oligonucleotide probe is complimentary to the bottom strand of the methylated nucleic acid of interest.

In some embodiments, the method is used to prepare a methylated target nucleic acid of interest for subsequent enrichment, and wherein prior to implementing the NaME protocol described herein on the reaction mixture, the nucleic acid sample is treated with sodium bisulfite and one of the oligonucleotide probes is complimentary to top strand of the unmethylated nucleic acid of interest, while the other oligonucleotide probe is complimentary to the bottom strand of the unmethylated nucleic acid of interest.

In some embodiments, the method is used to prepare both an unmethylated target nucleic acid of interest and a methylated target nucleic acid of interest for subsequent enrichment, wherein the method comprises: (i) a pair of oligonucleotide probes, one of which is complimentary to top strand of the methylated form of the unmethylated target nucleic acid of interest, while the other is complimentary to the bottom strand of the methylated form of the unmethylated target nucleic acid of interest, (ii) a pair of oligonucleotide probes, one of which is complimentary to top strand of the unmethylated form of the methylated target nucleic acid of interest, while the other is complimentary to the bottom strand of the unmethylated form of the methylated target nucleic acid of interest; and wherein prior to implementing the NaME protocol described herein on the reaction mixture, the nucleic acid sample is treated with sodium bisulfite.

In some embodiments, the method is used to prepare multiple target nucleic acids of interest, some of which are methylated target nucleic acids of interest, and some of which are unmethylated target nucleic acids of interest, and the method comprises (i) a pair of oligonucleotide probes, one of which is complimentary to top strand of the methylated form of each unmethylated target nucleic acid of interest, while the other is complimentary to the bottom strand of the methylated form of each unmethylated target nucleic acid of interest, (ii) a pair of oligonucleotide probes, one of which is complimentary to top strand of the unmethylated form of each methylated target nucleic acid of interest, while the other is complimentary to the bottom strand of the unmethylated form of each methylated target nucleic acid of interest.

Some aspects of the disclosure provide a method for preparing a target mutant nucleic acid for subsequent enrichment relative to a wild type nucleic acid, the method comprising the steps of: (a) exposing a nucleic acid sample comprising a double-stranded wild type nucleic acid and a double-stranded target nucleic acid suspected of containing a mutation to a thermostable double strand-specific nuclease (DSN) and a pair of oligonucleotide probes, one of which is complimentary to the wild type nucleic acid top strand and the other is complimentary to the wild type nucleic acid bottom strand, to create a reaction mixture, wherein at least one of the probes overlaps a sequence on the target nucleic acid containing the suspected mutation; (b) subjecting the reaction mixture to a denaturing temperature to permit denaturation of the wild type nucleic acid and the target mutant nucleic acid; and (c) reducing the temperature to permit hybridization of the probes to their corresponding sequences on the wild type and target mutant nucleic acids thereby forming complimentary wild type-probe duplexes on top and bottom strands, and partially complimentary target mutant-probe duplexes, wherein the DSN cleaves the complimentary wild type-probe duplexes but not the partially complimentary target mutant-probe duplexes.

In some embodiments, steps (b) and (c) are repeated for two or more cycles. In some embodiments, the reaction mixture further comprises an organic solvent. In some embodiments, the denaturing temperature is between 65-85° C.

Furthermore, in some embodiments step (c) of reducing the temperature is performed by applying a decreasing temperature gradient between temperatures that permit hybridization of probes having different Tm to their corresponding sequences on the target DNA. For example, a decreasing temperature gradient from 67° C. to 64° C. can be applied during DSN digestion, to allow diverse probes that have distinct Tms of 64-67° C. to hybridize effectively to their respective targets. ('Touch-down NaME'). The temperature gradient can preferably range between 2-20° C.

Some aspects of the disclosure provide a method for enriching a target mutant nucleic acid, the method comprising the steps of: (a) preparing an amplification reaction mixture comprising: a double-stranded wild type nucleic acid, a double-stranded target nucleic acid suspected of containing a mutation, a thermostable double strand-specific nuclease (DSN), a pair of oligonucleotide probes, one of which is complimentary to the wild type nucleic acid top strand and the other is complimentary to the wild type nucleic acid bottom strand, wherein at least one of the probes overlaps a sequence on the target nucleic acid containing the suspected mutation and PCR amplification components; (b) subjecting the reaction mixture to a denaturing temperature to permit denaturation of the wild type nucleic acid and the target mutant nucleic acid; (c) reducing the temperature to permit hybridization of the probes to their corresponding sequences on the wild type and target mutant nucleic acids thereby forming complimentary wild type-probe duplexes on top and bottom strands, and partially complimentary target mutant-probe duplexes, wherein the DSN cleaves the complimentary wild type-probe duplexes but not the partially complimentary target mutant-probe duplexes; and (d) subjecting the reaction mixture to an amplification condition thereby enriching the uncleaved target mutant nucleic acid relative to the cleaved wild type nucleic acid.

In some embodiments the amplification condition is such that amplification is applied to the probes rather than the hybridized nucleic acid. In some embodiments, a purification step is applied following probe binding to top-and-bottom DNA target strands, either before or after DSN cleavage, to remove excess unbound probes. Then following DSN cleavage the uncut probes are amplified (instead of amplifying the target DNA) and identified/quantified. Since probes that bind WT DNA will have been selectively digested by DSN, the presence of any given probe after amplification indicates a mutation under the region covered by this probe.

In some embodiments, steps (b) and (c) are repeated for two or more cycles before executing step (d). In some embodiments, steps (b), (c) and (d) are repeated for two or more cycles. In some embodiments, the reaction mixture further comprises an organic solvent. In some embodiments, the denaturing temperature is between 65-85° C. In some embodiments, the primers used for PCR amplification have a melting temperature that is below the temperature applied in step (c). In some embodiments, the amplification condition is COLD-PCR.

Some aspects of the disclosure provide a method for preparing unmethylated nucleic acids of interest for subsequent enrichment relative to corresponding methylated nucleic acids comprising the steps of: (a) ligating bisulfite-resistant adaptors to double stranded nucleic acids of interest; (b) subjecting the adaptor-linked nucleic acids to sodium bisulfite treatment and a nucleic acid amplification reaction to form double-stranded bisulfite-treated nucleic acids; (c) subjecting the bisulfite-treated nucleic acids to a temperature that permits preferential denaturation of unmethylated nucleic acids while methylated nucleic acids remain double-stranded; (d) exposing the unmethylated and methylated nucleic acids to double strand-specific nuclease (DSN) and conditions for optimal DSN activity, wherein the DSN cleaves the methylated double-stranded nucleic acids but not the unmethylated single-stranded nucleic acids.

Some aspects of the disclosure provide a method for preparing unmethylated nucleic acids of interest for subsequent enrichment relative to corresponding methylated nucleic acids comprising the steps of: (a) ligating bisulfite-resistant adaptors to double stranded nucleic acids of interest; (b) subjecting the adaptor-linked nucleic acids to sodium bisulfite treatment and a nucleic acid amplification reaction to form double-stranded bisulfite-treated nucleic acids; (c) subjecting the bisulfite-treated nucleic acids to a denaturing temperature that permits denaturation of both unmethylated and methylated nucleic acids to form unmethylated and methylated single stranded nucleic acids; (d) reducing the temperature to permit preferential formation of methylated duplexes, but not unmethylated duplexes; and (e) exposing the unmethylated and methylated nucleic acids to double strand-specific nuclease (DSN) and conditions for optimal DSN activity, wherein the DSN preferentially cleaves the methylated duplexes but not the unmethylated single-stranded nucleic acids.

Some aspects of the disclosure provide a method for preparing methylated nucleic acids of interest for subsequent enrichment relative to corresponding unmethylated nucleic acids comprising the steps of: (a) ligating bisulfite-resistant adaptors to double stranded nucleic acids of interest; (b) subjecting the adaptor-linked nucleic acids to sodium bisulfite treatment and a nucleic acid amplification reaction to form double-stranded bisulfite-treated nucleic acids; (c) subjecting the bisulfite-treated nucleic acids to a temperature that permits preferential denaturation of unmethylated nucleic acids while methylated nucleic acids remain double-stranded; and (d) exposing the unmethylated and methylated nucleic acids to an exonuclease and conditions for optimal exonuclease activity, wherein the exonuclease cleaves the unmethylated single-stranded nucleic acids but not the methylated double-stranded nucleic acids.

Some aspects of the disclosure provide a method for preparing methylated nucleic acids of interest for subsequent enrichment relative to corresponding unmethylated nucleic acids comprising the steps of: (a) ligating bisulfite-resistant adaptors to double stranded nucleic acids of interest; (b) subjecting the adaptor-linked nucleic acids to sodium bisulfite treatment and a nucleic acid amplification reaction to form double-stranded bisulfite-treated nucleic acids; (c) subjecting the bisulfite-treated nucleic acids to a denaturing temperature that permits denaturation of both unmethylated and methylated nucleic acids to form unmethylated and methylated single stranded nucleic acids; (d) reducing the temperature to permit preferential formation of methylated duplexes, but not unmethylated duplexes; and (e) exposing the unmethylated and methylated nucleic acids to an exonuclease and conditions for optimal exonuclease activity, wherein the exonuclease preferentially cleaves the unmethylated single-stranded nucleic acids, but not the methylated duplexes.

In some embodiments, the nucleic acid amplification reaction of step (b) is selected from the group consisting of: PCR; full COLD-PCR, fast COLD-PCR; ice-COLD-PCR, temperature-tolerant COLD-PCR and limited denaturation time COLD-PCR. In some embodiments, the cleaved unmethylated single stranded nucleic acids and the uncleaved methylated duplexes are subjected to an amplification condition using the bisulfite resistant adaptors ligated in step (a). In some embodiments, the amplification condition is selected from the group consisting of: PCR, full COLD-PCR, fast COLD-PCR; ice-COLD-PCR, temperature-tolerant COLD-PCR and limited denaturation time COLD-PCR. In some embodiments, naturally AT-rich sequences are removed prior to the sodium bisulfite treatment.

In any of the foregoing methods, the probes are in a molar excess of 100-fold to 1 billion-fold compared to the wild type and target nucleic acids. In any of the foregoing methods, one of the probes overlaps a sequence on the top strand of the target nucleic acid containing the mutation, while the other probe overlaps a sequence on the bottom strand of the target nucleic acid containing the mutation and the two probes partially overlap each other. In any of the foregoing methods, each probe comprises a locked nucleic acid (LNA), peptide nucleic acid (PNA), xeno nucleic acid (XNA), nucleic acid with any known modified base or RNA. In any of the foregoing methods, the method is used to prepare two or more different target mutant nucleic acids for subsequent enrichment relative to corresponding wild type nucleic acids, and the method further comprises one or more additional pairs of probes directed to the different wild type nucleic acids, wherein for each pair of probes, one of the probes is complimentary to the wild type nucleic acid top strand and the other is complimentary to the wild type nucleic acid bottom strand. In any of the foregoing methods, the nucleic acid sample comprises genomic DNA or circulating DNA in urine, plasma or other bodily fluids.

In any of the foregoing methods, the methods further comprise enriching the nucleic acids for regions of interest prior to implementing NaME protocol described herein as follows: contacting the nucleic acid sample with bait oligonucleotides that bind to different nucleic acids of interest on top and bottom strands, permitting binding of the bait oligonucleotides to the nucleic acids of interest on top and bottom strands, and isolating the bait oligonucleotides with the nucleic acids of interest bound thereto from remaining nucleic acids. In some embodiments, the bait oligonucleotides are biotinylated at one end. In some embodiments, the bait oligonucleotides are attached to beads.

In any of the foregoing methods, prior to implementing the NaME protocol described herein, the nucleic acid sample is subjected to an amplification condition.

In any of the foregoing methods, the methods further comprise enriching the target mutant nucleic acid relative to the wild type nucleic acid by subjecting the reaction mixture with cleaved wild type-probe duplexes and uncleaved target mutant nucleic acids to an amplification condition thereby enriching the uncleaved target mutant nucleic acid relative to the cleaved wild type nucleic acid. In some embodiments, the amplification condition is selected from the group consisting of: PCR, COLD-PCR, ligation mediated PCR or COLD-PCR using common ligated adaptors, multiplex PCR, and isothermal amplification.

In any of the foregoing methods, each probe can be optionally modified at the 3' end to prevent polymerase extension.

In any of the foregoing methods, the methods further comprise enriching the target mutant nucleic acid relative to the wild type nucleic acid by subjecting the reaction mixture with cleaved wild type-probe duplexes and uncleaved target mutant nucleic acids to a further DNA degradation condition which hydrolyzes enzymatically the DSN-cleaved wild type-probe duplexes, with the degradation initiated at the position of the cleavage.

In any of the foregoing methods, the methods further comprise analyzing the reaction mixture with cleaved wild type-probe duplexes and uncleaved target mutant nucleic acids using one or more of the methods selected from the group consisting of: MALDI-TOF, HR-Melting, Di-deoxysequencing, Single-molecule sequencing, massively parallel sequencing (MPS), pyrosequencing, SSCP, RFLP, dHPLC, CCM, digital PCR and quantitative-PCR.

In some embodiments of any one of the provided methods, the DSN enzyme is a DNA guided or RNA guided enzyme. In some embodiments of any one of the provided methods, the enzyme is an RNA guided enzyme, e.g., Cas9. In some embodiments of any one of the provided methods, the enzyme is a DNA guided enzyme, e.g., an Argonaute enzyme.

Some aspects of the disclosure provide a method for preparing a target mutant nucleic acid for subsequent enrichment relative to a wild type nucleic acid comprising subjecting a nucleic acid sample comprising a double-stranded wild type nucleic acid and a double-stranded target nucleic acid suspected of containing a mutation to a condition that destabilizes the double stranded wild type and target mutant nucleic acids; contacting the destabilized double stranded wild type and target mutant nucleic acids with a pair of oligonucleotide probes, one of which is complimentary to the wild type nucleic acid top strand and the other is complimentary to the wild type nucleic acid bottom strand, to permit hybridization of the probes to their corresponding sequences on the wild type and target mutant nucleic acids thereby forming complimentary wild-type-probe duplexes on top and bottom strands, and partially complimentary target mutant-probe duplexes, wherein at least one of the probes overlaps a sequence on the target nucleic acid containing the suspected mutation, and wherein one or both probes comprise a locked nucleic acid (LNA), peptide nucleic acid (PNA), xeno nucleic acid (XNA), or a nucleic acid with any known modified base or RNA which is capable of blocking PCR amplification; and subjecting the complimentary wild-type-probe duplexes on top and bottom strands, and partially complimentary target mutant-probe duplexes to an ving a amplification condition. The probe(s) that overlap the mutation position act to block PCR amplification, e.g., acting as a clamp, for the wild-type top and bottom DNA strands, thereby inhibiting amplification of the wild-type nucleic acid. When the probe duplexes with a partially complimentary target mutant sequence, it is less able to inhibit PCR amplification, thereby permitting selective amplification of the mutant nucleic acid as compared to the wild-type, without a need for a cleaving enzyme (e.g., DSN).

Each of the embodiments and aspects of the invention can be practiced independently or combined. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

These and other aspects of the inventions, as well as various advantages and utilities will be apparent with reference to the Detailed Description. Each aspect of the invention can encompass various embodiments as will be understood.

All documents identified in this application are incorporated in their entirety herein by reference.

BRIEF DESCRIPTION OF THE DRAWINGS

FIG. 7B is a table summarizing the mutation abundance found in a DSN reaction performed directly on fragmented genomic DNA via an 11-plex assay. The 11 mutated targets were formed using DNA from Horizon Dx. In the figure, column 1 shows the name of the target gene, columns 2 and 3 represent the mutation position and mutation type, respectively, column 4 shows the mutation abundance as derived via digital PCR when DSN is omitted; column 5 shows the mutation abundance when DSN is applied (NaME), column 6 represents the mutation abundance when both DSN and the probes are omitted, and column 7 shows the expected mutation abundance according to the Horizon manufacturer, without any treatment.

DETAILED DESCRIPTION OF THE INVENTION

Figure 1A:
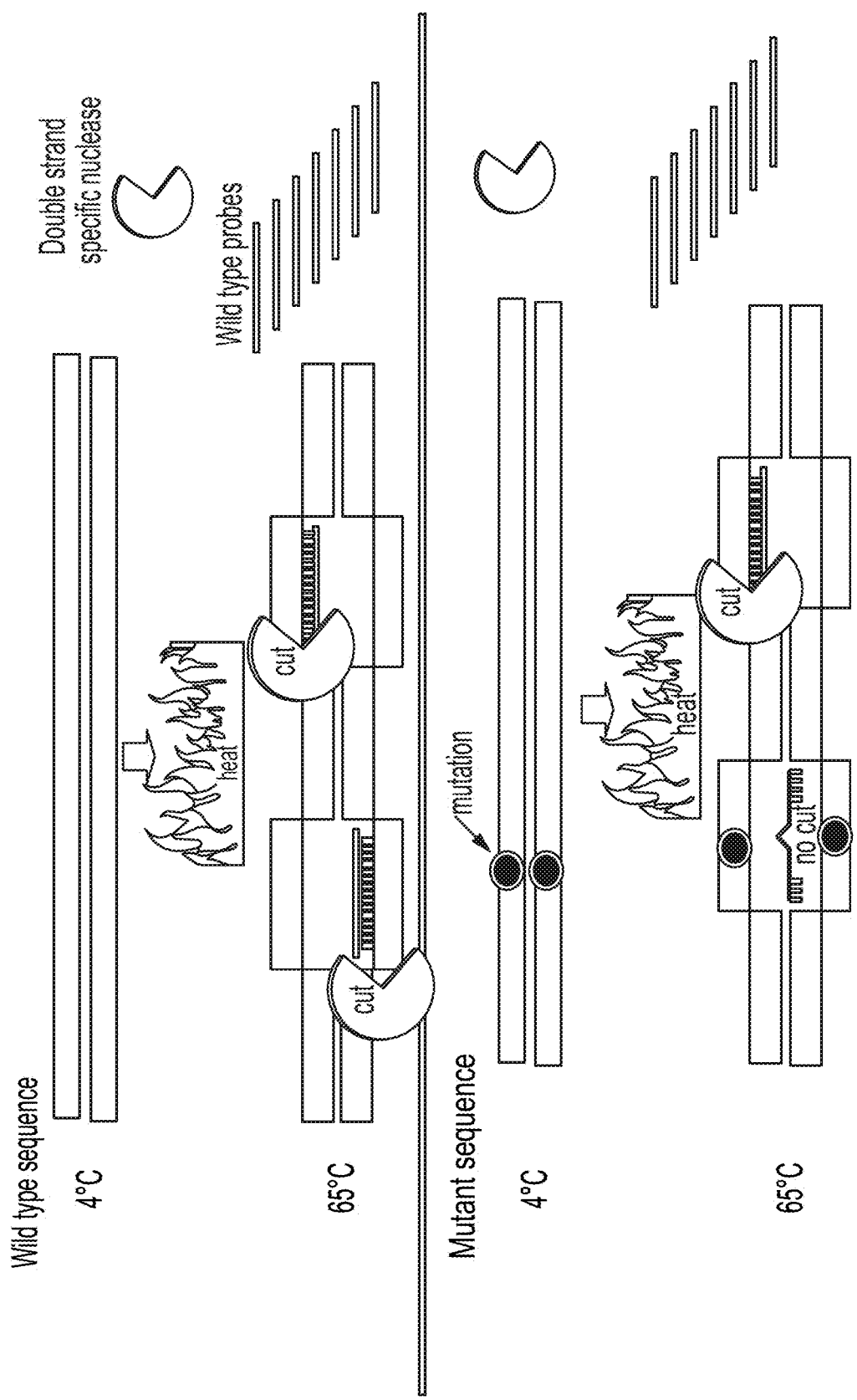
FIG. 1A is a schematic the selective degradation of wild-type double-stranded DNA using duplex specific nuclease (DSN) and sequence selective oligonucleotides ('probes') at elevated temperatures. A DNA denaturation step prior to DSN action may optionally be applied in order to generate single stranded DNA prior to probe binding and selective wild type degradation of both DNA strands.

In most applications involving detection of low-prevalence somatic mutations, the mutant alleles are detected following a polymerase chain reaction (PCR) step that amplifies both mutant and wild type alleles. Methods have also been described to preferentially amplify the mutated alleles over wild-type alleles (e.g. co-amplification at lower denaturation temperature or COLD-PCR and improved and complete enrichment COLD PCR or ice-COLD-PCR; Li J, Wang L, Mamon H, Kulke M H, Berbeco R, Makrigiorgos G M. Replacing PCR with COLD-PCR enriches variant DNA sequences and redefines the sensitivity of genetic testing. Nat Med 2008; 14:579-84; Milbury C A, Li J, Makrigiorgos G M. Ice-COLD-PCR enables rapid amplification and robust enrichment for low-abundance unknown DNA mutations. Nucleic Acids Res; 39:e2). However, the enrichment that can be obtained via such PCR-based methods has a limit, since after several cycles of synthesis, the polymerase unavoidably introduces mis-incorporations (PCR errors) that are subsequently scored as mutations. Repeated amplifications can also introduce mis-priming which results in the amplification of unwanted non-target sequences. Furthermore, there are powerful genetic analysis methods currently emerging ('third generation sequencing' Nanopore, Pac-Bio systems) that may obviate the use of PCR altogether. Therefore, mutation enrichment methods that reduce the amount of PCR performed, or that can operate without PCR, or in conjunction with PCR if so required, are important.

The present disclosure is based, at least in part, on the novel development of a technique, Nuclease-assisted Mutation Enrichment (NaME) that results in the preferential cleavage of non-variant/wild type DNA or RNA, thereby allowing for subsequent selective enrichment of variant (mutant) target sequences. Thus, NaME can be used before, during, or after an amplification step, such as PCR, or without any amplification, depending on the application. Subsequently, the mutation-enriched sequences can be screened via any currently available method for identifying mutations, including Sanger Sequencing, high resolution melting (HRM), SSCP, next generation massively parallel sequencing, and MALDI-TOF for known mutations; and Single Molecule Sequencing-or third generation sequencing for high-throughput sequencing of low-level mutations. NaME can also be applied to detect low levels of un-methylated alleles (Methylation-Sensitive Nuclease-assisted minor-allele Enrichment or MS-NaME) in a background of methylated alleles (or vice-versa).

The methods described herein greatly improve the current detection limits of mutation/methylation detection technologies, thereby enhancing reliability of patient-specific mutation screening, for example, in heterogeneous tumor samples or in circulating DNA. The methods described herein also enable high multiplexity of targets (i.e., enable the simultaneous screening of a panel of DNA regions), thus enabling high-throughput methods to be used for somatic mutation detection, (for example, massively parallel sequencing, MPS). NaME is particularly useful in the field of circulating biomarkers for cancer applications, pre-natal diagnostic applications, and infectious disease applications.

'Wild type target sequence' refers to a nucleic acid that is more prevalent in a nucleic acid sample than a corresponding target sequence (e.g, same region of gene but different nucleic acid sequence). The wild type sequence makes-up over 50% of the total wild type sequence+mutant target sequence in a sample. The wild type sequence can be expressed at the RNA and/or DNA level 10×, 15×, 20×, 25×, 30×, 35×, 40×, 45×, 50×, 60×, 70×, 80×, 90× 100×, 150×, 200× or more than the target sequence. For example, a sample (e.g., blood sample) may contain numerous normal cells and few cancerous cells. The normal cells contain wild-type alleles (non-mutant) sequences, while the small number of cancerous cells contain target sequences. As used herein, a 'wild type strand' refers to a single nucleic acid strand of a wild type sequence. The term 'wild-type' typically refers to the most common polynucleotide sequence or allele for a certain gene in a population. Generally, the wild-type allele will be obtained from normal cells.

The wild type sequence is about 13-2000 nucleotides long. In some embodiments, the wild type sequence is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Wild type sequences will share at least 50%, 60%, 70%, 80%, 85%, 90%, 91%, 92%, 93%, 94%, 95%, 96%, 97%, 98%, 99% or more homology to the corresponding target sequence, but will differ by at least one nucleotide from the target sequence. In some embodiments, the at least one nucleotide is a methylated cytosine. In some embodiments, the at least one nucleotide is an unmethylated cytosine. Wild type sequences according to the invention can be amplified by PCR with the same pair of primers as that used for the mutant sequence.

A 'target nucleic acid' or 'target sequence', used interchangeably herein, refers to a nucleic acid that is less prevalent in a nucleic acid sample than a corresponding wild type sequence. The target sequence makes-up less than 50% of the total amount of wild type sequence+target sequence in a sample. Preferably the target sequence is expressed at the RNA and/or DNA level 1:10, 1:15, 1:20, 1:25×, 1:30, 1:35, 1:40, 1:45, 1:50, 1:60, 1:70, 1:80, 1:90, 1:100, 1:150, 1:200× or less than the wild type sequence. In some embodiments, the target sequence is a mutant allele. For example, a sample (e.g., blood sample) may contain numerous normal cells and few cancerous cells. The normal cells contain wild-type (i.e., non-mutant) sequences, while the small number of cancerous cells contain target mutant sequences. In some embodiments, the target sequence is repeat sequences that occur at large numbers in human genome (including but not limited to ALU elements, LINE elements, SINE elements, di-nucleotide repeats, tri-nucleotide repeats). Altered repeat sequences occur often in diseased states and application of the present invention in detecting alterations in repeat sequences are of interest. In some embodiments, the methods described herein are directed to detecting fetal DNA in a nucleic acid sample obtained from a mother. In this embodiment, the fetal DNA is the target sequence while the more prevalent mother DNA is the wild type sequence. In some embodiments, the target sequence is a methylated allele. In some embodiments, the target sequence is an unmethylated allele. As used herein, a "target strand" refers to a single nucleic acid strand of a target sequence.

In some embodiments, the target sequence is 13-2000 nucleotides long. In some embodiments, the target sequence is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Target sequences share at least 50%, 60%, 70%, 80%, 85%, 90%, 91%, 92%, 93%, 94%, 95%, 96%, 97%, 98%, 99% or more homology to the corresponding wild type sequence, but differs by at least one nucleotide from the wild type sequence. In some embodiments, the at least one nucleotide is a methylated cytosine. In some embodiments, the at least one nucleotide is an unmethylated cytosine. Target sequences according to the invention can be amplified via PCR with the same pair of primers as those used for the wild type sequence.

'Target mutant sequence' or 'mutant target sequence' refers to a nucleic acid that is less prevalent in a nucleic acid sample than a corresponding wild type sequence. The target mutant sequence typically makes-up less than 50% of the total amount of wild type sequence+mutant sequence in a sample. The target mutant sequence may be expressed at the RNA and/or DNA level 1:10, 1:15, 1:20, 1:25×, 1:30, 1:35, 1:40, 1:45, 1:50, 1:60, 1:70, 1:80, 1:90, 1:100, 1:150, 1:200× or less than the wild type sequence. For example, a sample (e.g., blood sample) may contain numerous normal cells and few cancerous cells. The normal cells contain wild-type (non-mutant) alleles, while the small number of cancerous cells contain target mutant sequences. In some embodiments, the invention is directed to detecting fetal DNA in a nucleic acid sample obtained from a mother. In this embodiment, the target mutant sequence is the fetal DNA while the more prevalent mother DNA is the wild type sequence. As used herein, a target mutant sequence is meant to include fetal DNA obtained from a pregnant mother. In some embodiments, the present disclosure is directed to detecting one or more methylated alleles in the presence of a large excess of unmethylated alleles, or vice versa in epigenetic analysis.

The target mutant sequence is about 13-2000 nucleotides long. In some embodiments, the target mutant sequence is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Target mutant sequences share at least 50%, 60%, 70%, 80%, 85%, 90%, 91%, 92%, 93%, 94%, 95%, 96%, 97%, 98%, 99% or more homology to the corresponding wild type sequence, but differs by at least one nucleotide from the wild type sequence. Mutant target sequences according to the invention can be amplified via PCR with the same pair of primers as those used for the wild type sequence.

The term 'mutant' refers to a nucleotide change (i.e., a single or multiple nucleotide substitution, deletion, insertion, or methylation, or alteration in the number of polynucleotide repeats) in a nucleic acid sequence. A nucleic acid which bears a mutation has a nucleic acid sequence (mutant allele) that is different in sequence from that of the corresponding wild-type sequence. The methods described herein are especially useful in preferentially cleaving wild type sequences, thereby allowing for selective enrichment of several or numerous mutant target sequences simultaneously. The mutant alleles can contain between 1 and 500 nucleotide sequence changes. A mutant allele may have 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400 or 500 nucleotide sequence changes compared to a corresponding wild-type allele. Typically, a mutant allele will contain between 1 and 10 nucleotide sequence changes, and more typically between 1 and 5 nucleotide sequence changes. The mutant allele will have 50%, 60%, 70%, 80%, 85%, 90%, 91%, 92%, 93%, 94%, 95%, 96%, 97%, 98%, 99% or more homology to the wild-type allele. Generally, the mutant allele will be obtained from diseased tissues or cells and is associated with a disease state.

As used herein, a 'region of interest' is a sequence that will be interrogated for variations such as clinically relevant mutations, and methylation/unmethylation patterns. 'Enriching a mutant target sequence' refers to increasing the amount of a mutant target sequence and/or increasing the ratio of mutant target sequence relative to the corresponding wild type sequence in a sample. For example, where the ratio of mutant sequence to wild type sequence is initially 5% to 95% in a sample, the mutant sequence may be preferentially amplified in an amplification reaction so as to produce a ratio of 70% mutant sequence to 30% wild type sequence. Thus, there is a 14 fold enrichment of the mutant sequence relative to the wild type sequence in this hypothetical example. Generally, enrichment of a mutant target sequence results in a 2× to 200× increase in the mutant target sequence relative to the wild type sequence prior to enrichment. The enrichment of the mutant target sequence is at least a 2×, 3×, 4×, 5×, 6×, 7×, 8×, 9×, 10×, 15×, 20×, 25×, 30×, 35×, 40×, 45×, 50×, 60×, 70×, 80×, 90×100×, 150×, 200× or more fold enrichment. Enrichment of a mutant target sequence results in a sample having 10%, 15%, 20%, 25%, 30%, 35%, 40%, 45%, 50%, 55%, 60%, 65%, 70%, 80%, 90%, 95% or more, mutant target sequence compared to wild type sequence (e.g., 10% mutant target sequence: 90% wild type sequence to 95% mutant target sequence: 5% wild type sequence).

'Allele' refers to alternative forms of a gene, portion thereof or non-coding region of DNA that occupy the same locus or position on homologous chromosomes that have at least one difference in the nucleotide sequence. The term allele can be used to describe DNA from any organism including but not limited to bacteria, viruses, fungi, protozoa, molds, yeasts, plants, humans, non-humans, animals, and archaebacteria. The alleles may be found in a single cell (e.g., two alleles, one inherited from the father and one from the mother) or within a population of cells (e.g., a wild-type allele from normal tissue and a somatic mutant allele from diseased tissue).

An allele can be 13-2000 nucleotides long. In one embodiment the allele is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Alleles will generally share 50%, 60%, 70%, 80%, 85%, 90%, 91%, 92%, 93%, 94%, 95%, 96%, 97%, 98%, 99% or more homology to each other. Alleles according to the invention can be amplified by PCR with the same pair of primers.

In one embodiment, the methods described herein are used to enrich a polymorphism. Any given gene may have none, one, or many allelic forms (polymorphism). Common mutational changes which give rise to alleles may be the result of natural or artificial (e.g., chemical carcinogens) deletions, additions, or substitutions of nucleotides. Each of these types of changes may occur alone, or in combination with the others, one or more times in a given sequence.

As used herein the term 'melting temperature' or I'm' refers to the temperature at which a polynucleotide dissociates from its complementary sequence. Generally, the Tm may be defined as the temperature at which one-half of the Watson-Crick base pairs in a duplex nucleic acid molecule are broken or dissociated (i.e., are 'melted') while the other half of the Watson-Crick base pairs remain intact in a double stranded conformation. In other words, the Tm is defined as the temperature at which 50% of the nucleotides of two complementary sequences are annealed (double strands) and 50% of the nucleotides are denatured (single strands). Tm, therefore defines a midpoint in the transition from double-stranded to single-stranded nucleic acid molecules (or, conversely, in the transition from single-stranded to double-stranded nucleic acid molecules).

The Tm can be estimated by a number of methods, for example by a nearest-neighbor calculation as per Wetmur 1991 (Wetmur, J. G. 1991. DNA probes: applications of the principles of nucleic acid hybridization. Crit Rev Biochem Mol Biol 26: 227-259, hereby incorporated by reference) and by commercial programs including Oligo™ Primer Design and programs available on the internet. Alternatively, the Tm can be determined though actual experimentation. For example, double-stranded DNA binding or intercalating dyes, such as ethidium bromide or SYBR-green (Molecular Probes) can be used in a melting curve assay to determine the actual Tm of the nucleic acid. Additional methods for determining the Tm of a nucleic acid are well known in the art and described herein.

As used herein, 'reaction mixture' refers to a mixture of constituents including but not limited to a nucleic acid sample comprising a double-stranded wild type nucleic acid and a double-stranded target nucleic acid suspected of containing a mutation, and a pair of oligonucleotide probes that are complimentary to top and bottom strands of the wild type nucleic acid. The reaction mixture can also include reagents, such as, but not limited to, salt(s), buffer(s), and enzyme(s) such as double strand-specific nuclease (DSN), exonuclease, and polymerase.

As used herein, a nucleic acid sample refers to any substance containing or presumed to contain a nucleic acid of interest (target and wild type sequences) or which is itself a nucleic acid containing or presumed to contain a target nucleic acid of interest. The term "nucleic acid sample" thus includes a sample of nucleic acid (genomic DNA, cDNA, RNA), cell, organism, tissue, or fluid, including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules. The nucleic acid sample may be obtained from mammals, viruses, bacteria or plants. In some embodiments, the nucleic acid sample is DNA circulating in plasma, urine or other bodily fluids.

As used herein "oligonucleotide probes" refer to molecules comprising two or more deoxyribonucleotides or ribonucleotides. The methods described herein utilize a pair of oligonucleotide probes, one of which is complimentary to the wild type nucleic acid top strand and the other is complimentary to the wild type nucleic acid bottom strand. By "complimentary" it is meant that the probes hybridize without any mismatches to the sequences in the top and bottom stands of the wild type nucleic acid. The oligonucleotide probes are non-identical, i.e., the sequences of the two probes are different from each other. In some embodiments, the probes do not overlap each other, i.e., they do not bind to each other. At least one of the probes overlaps a sequence on the target nucleic acid containing the suspected mutation, i.e., the probe hybridizes to the sequence on the target nucleic acid containing the suspected mutation with at least one mismatch thereby forming a "partially complimentary" target mutant-probe duplex.

In some embodiments, one of the probes overlaps a sequence on the top strand of the target nucleic acid containing the mutation, while the other probe overlaps a sequence on the bottom strand of the target nucleic acid containing the mutation. Thus, the probes hybridize respectively to the top and bottom sequences on the target nucleic acid containing the suspected mutation with at least one mismatch. In such embodiments, the probes partially overlap each other. However, they do not bind substantially to each other.

The oligonucleotide probes may be anywhere between 5 and 100 bases long. In some embodiments, the probes are 5, 10, 20, 30, 40, 50, 60, 70, 80, 90, or 100 bases long. In some embodiments, the probes are in a molar excess of 100-fold- to 1 billion-fold compared to the wild type and target nucleic acids (e.g., 100-fold, 500-fold, 1000-fold, 10,000-fold, 50,000-fold, 100,000-fold, 500,000-fold, 1 million-fold, 500-million fold, 100 million-fold, 1 billion-fold in excess as compared to the wild type and target nucleic acids). In some embodiments the probes are in a molar concentration of 1 µM, 10 µM, 50 µM, 100 µM, 200 µM, 300 µM, 400 µM, 500 µM, 600 µM, 700 µM, 800 µM, 900 µM, or 1,000 µM in the reaction.

By "selectively cleaved" or "preferentially cleaved" is meant that the subject methods preferentially cut, i.e., cleave, deoxyribonucleic acid molecules present in perfectly matched double-stranded nucleic acids, e.g., DNA-DNA duplexes and DNA-RNA duplexes. Perfectly matched double-stranded nucleic acids are hybrid structures between complementary strands where no mismatches are present, as compared to partially complimentary nucleic acid duplexes of the same length. Thus, in the methods described herein complimentary DNA containing duplex nucleic acids (i.e., without any mismatches) are cleaved to a much greater extent than partially complimentary nucleic acid duplexes (i.e., with one or more mismatches), non-DNA containing nucleic acid duplexes and/or single-stranded nucleic acids. In other words, the subject methods are able to cleave or cut perfectly matched nucleic acids duplexes in a sample at a much greater rate than other nucleic acid molecules that may be present in the sample being treated, where the rate of perfectly matched nucleic acids duplex cleavage is typically at least 5 fold, at least 10 fold, at least 50 fold, or at least 100 fold greater than the rate of cleavage of other nucleic acids that may be present in the sample being treated.

As used herein, "primers' refers to oligonucleotides that anneal to opposite strands of a mutant target and wild type sequence so as to form an amplification product during a PCR reaction.

NaME on Double Stranded DNA

Accordingly, some aspects of the disclosure provide methods for preparing a target mutant nucleic acid for subsequent enrichment relative to a wild type nucleic acid. The subsequent enrichment can be achieved by applying amplification conditions to the produced reaction mixture.

In some embodiments, the method comprises subjecting a nucleic acid sample comprising a double-stranded wild type nucleic acid and a double-stranded target nucleic acid suspected of containing a mutation to a condition that destabilizes the double stranded wild type and target mutant nucleic acids; contacting the destabilized double stranded wild type and target mutant nucleic acids with a pair of oligonucleotide probes, one of which is complimentary to the wild type nucleic acid top strand and the other is complimentary to the wild type nucleic acid bottom strand, to permit hybridization of the probes to their corresponding sequences on the wild type and target mutant nucleic acids thereby forming complimentary wild-type-probe duplexes on top and bottom strands, and partially complimentary target mutant-probe duplexes, wherein at least one of the probes overlaps a sequence on the target nucleic acid containing the suspected mutation; and exposing the complimentary wild-type-probe duplexes and the partially complimentary target mutant-probe duplexes to a double strand-specific nuclease (DSN), wherein the DSN cleaves the complimentary wild type-probe duplexes but not the partially complimentary target mutant-probe duplexes.

In some embodiments, the method comprises exposing a nucleic acid sample comprising a double-stranded wild type nucleic acid and a double-stranded target nucleic acid suspected of containing a mutation to a double strand-specific nuclease (DSN) and a pair of oligonucleotide probes, one of which is complimentary to the wild type nucleic acid top strand and the other is complimentary to the wild type nucleic acid bottom strand, to create a reaction mixture, wherein at least one of the probes overlaps a sequence on the target nucleic acid containing the suspected mutation; and subjecting the reaction mixture to a condition that destabilizes the double stranded wild type and target mutant nucleic acids to permit hybridization of the probes to their corresponding sequences on the wild type and target mutant nucleic acids thereby forming complimentary wild-type-probe duplexes on top and bottom strands, and partially complimentary target mutant-probe duplexes, wherein the DSN cleaves the complimentary wild type-probe duplexes but not the partially complimentary target mutant-probe duplexes.

NaME utilizes nucleases (DNases) that show a strong preference for cleaving double stranded DNA versus single stranded DNA or RNA. DNases that can be used in the methods described herein include, but are not limited to, native shrimp dsDNase, recombinant shrimp dsDNase, King crab nuclease (DSN) and bovine DNase I. NaME takes advantage of the DSN properties to cleave specific sequences from both top and bottom DNA strands of wild-type DNA as shown on FIG. 1A. In contrast, mutation-containing DNA is not cleaved or cleaved to a significantly less extent than wild type DNA. Hence, a subsequent PCR reaction after DSN digestion amplifies preferentially the mutant alleles that remain substantially intact, and leads to enrichment of mutant versus wild type alleles.

For the purposes of the present disclosure, the term "double-strand specific nuclease" or "DSN" includes DNA/RNA guided enzymes which have preferential activity on double-stranded DNA, as compared to single stranded DNA. Examples of such enzymes that can be employed in conjunction with NaME include the RNA-guided Cas9 enzymes (Gu et al, *Depletion of Abundant Sequences by Hybridization (DASH): Using Cas9 to remove unwanted high-abundance species in sequencing libraries and molecular counting applications* Genome Biology 2016; 17, 41), or the Argonaute DNA-guided enzymes (Gao et al, *DNA-guided genome editing using the Natronobacterium gregoryi Argonaute*, Nature Biotechnology May 2016 advanced online publication). These DNA/RNA guided enzymes digest DNA with high preference when the probe ('guide oligonucleotide') is fully matched to the target DNA, and less so when there is a mismatch. By employing probes targeting both top and bottom DNA strands in an overlapping fashion as described in the present invention, NAME can be applied with DNA/RNA guided enzymes, in the same manner as when using other DSN nucleases described herein.

During NaME, (FIG. 1A) DSN and a pair of oligonucleotide probes that match the top and bottom strands of the wild type nucleic acid of interest are added to (i.e., exposed or contacted with) a nucleic acid sample comprising double-stranded wild type nucleic acid and double-stranded target nucleic acid suspected of containing a mutation to create a reaction mixture. The nucleic acid sample is exposed to the DSN and the oligonucleotide probes at a low temperature at which the DSN is inactive (e.g., 4° C.). At least one of the oligonucleotide probes overlaps sequences on the target nucleic acid that are suspected of containing clinically important mutations (e.g. KRAS codon 12/13 sequences; p53 sequences; tri-nucleotide repeat sequences; etc.). The second oligonucleotide binds the opposite target nucleic acid strand from the first oligonucleotide probe, and can have similar length as the first oligonucleotide. In some embodiments, this second probe is designed to match a sequence on the target nucleic acid that normally does not contain mutations. In some embodiments, the probes are in a molar excess of 100-fold, 500-fold, 1000-fold, 10,000-fold, 50,000-fold, 100,000-fold, 500,000-fold, 1 million-fold, 500-million fold, 100 million-fold, 1 billion-fold compared to the wild type and target nucleic acids.

The reaction mixture is then subjected to a condition that destabilizes the double stranded wild type and mutant nucleic acids to permit hybridization of the probes to their corresponding sequences on the wild type and mutant nucleic acids thereby forming complimentary wild-type-probe duplexes on top and bottom strands, and partially complimentary mutant-probe duplexes. By "destabilizing" it is meant that the double stranded wild type and target mutant nucleic acids denature to such an extent so as to allow the probes to hybridize to their corresponding sequences, but the wild type and target mutant nucleic acids do not denature completely. A condition that destabilizes the double stranded wild type and mutant nucleic acids to permit hybridization of the probes to their corresponding sequences on the wild type and mutant nucleic acids include addition of an organic solvent such as, but not limited to DMSO, betaine or formamide and/or an increase in temperature combined with a thermostable DSN. The increase in temperature is such that it enables specific probe hybridization to its corresponding sequence. The temperature of the reaction mixture is raised to a temperature that destabilizes the double stranded structure (e.g., 65° C.-80° C. including 65° C., 70° C., 75° C., 80° C.) but does not denature it completely. This destabilizing temperature is typically about 10-20° C. below the melting temperature (Tm) of the nucleic acid sequence. At this temperature, the oligonucleotide probes invade and bind to their corresponding sequences on the wild type and mutant nucleic acids. The probes fully match the sequences on the wild type nucleic acid and can, thus, form complimentary wild type-probe duplexes (i.e., with no mis-matches).

If a suspected mutation is present on the target nucleic acid, the binding between the probe and the target nucleic acid is inefficient and results in partially complimentary mutant-probe duplexes (i.e., with mis-matches). The complimentary wild type-probe duplexes are recognized and cleaved by the DSN enzyme, In contrast, the partially complimentary mutant-probe duplexes remains substantially intact.

In some embodiments, one of the oligonucleotide probes overlaps a sequence on the target nucleic acid that is suspected of containing a mutation while the second probe is designed to match a sequence at a different position on the target nucleic acid that normally does not contain mutations (FIG. 1A). Hence, the approach shown on FIG. 1A typically leads to cleavage of both strands for wild type nucleic acid while only a single DNA strand of the mutant nucleic acid is cleaved.

In some embodiments, the methods described herein are performed by first destabilizing the double-stranded wild type nucleic acid and the double-stranded target nucleic acid suspected of containing a mutation. The destabilized wild type nucleic acid and the target mutant nucleic acid are then contacted with the oligonucleotide probes to permit hybridization of the probes to their corresponding sequences on the wild type and target mutant nucleic acids thereby forming complimentary wild-type-probe duplexes on top and bottom strands, and partially complimentary target mutant-probe duplexes. By "contacting" it is meant that the probes are added to the nucleic acids and the components are mixed, or the nucleic acids are added to the probes and the components are mixed. The duplexes are then exposed to DSN which preferentially cuts the complimentary wild type-probe duplexes but not the partially complimentary target mutant-probe duplexes.

Some aspects of the disclosure provide methods for preparing a target mutant nucleic acid for subsequent enrichment relative to a wild type nucleic acid comprising exposing a nucleic acid sample comprising a double-stranded wild type nucleic acid and a double-stranded target nucleic acid suspected of containing a mutation to a pair of oligonucleotide probes, one of which is complimentary to the wild type nucleic acid top strand and the other is complimentary to the wild type nucleic acid bottom strand, to create a reaction mixture, wherein at least one of the probes overlaps a sequence on the target nucleic acid containing the suspected mutation; subjecting the reaction mixture to a denaturing temperature to permit denaturation of the wild type nucleic acid and the target mutant nucleic acid; reducing the temperature of the reaction mixture to permit formation of complimentary wild type-probe duplexes on top and bottom strands and partially complimentary target mutant-probe duplexes; and exposing the reaction mixture to a double strand-specific nuclease (DSN), wherein the DSN cleaves the complimentary wild type-probe duplexes but not the partially complimentary target mutant-probe duplexes.

In these methods, the double stranded wild type and target nucleic acids in the presence of the two probes are first denatured by subjecting the reaction mixture to a denaturing temperature, while also optionally including organic solvents like DMSO, betaine or formamide. The denaturing temperature should be sufficiently high so as to allow the full denaturation of the wild type and target nucleic acids (e.g., 75° C., 80° C., 85° C., 90° C., or 95° C.). In some embodiments, the denaturing temperature is about 1° C. to 30° C. above the Tm of the wild type and nucleic acid sequence (e.g., 1° C., 5° C., 10° C., 15° C., 20° C., 25° C., 30° C. above the Tm of the wild type and nucleic acid sequence).

Next the temperature of the reaction mixture is decreased allowing the wild type and target nucleic acids to hybridize with the oligonucleotide probes to form complimentary wild type-probe duplexes on top and bottom strands (i.e., with no mis-matches) and partially complimentary mutant-probe duplexes (i.e., with mis-matches). In some embodiments, this hybridization temperature is 40° C., 45° C., 50° C., 55° C., 60° C., 65° C., 70° C., or 75° C.). At this hybridization temperature, since the two probes are in high excess relative to the target nucleic acid, they bind first to their respective targets, i.e., while the two parent strands of the wild type and target nucleic acids have not yet re-associated and remain substantially single-stranded. In some embodiments, the probes are in a molar excess of 100-fold, 500-fold, 1000-fold, 10,000-fold, 50,000-fold, 100,000-fold, 500,000-fold, 1 million-fold, 500-million fold, 100 million-fold, 1 billion-fold compared to the wild type and target nucleic acids.

Figure 1B:
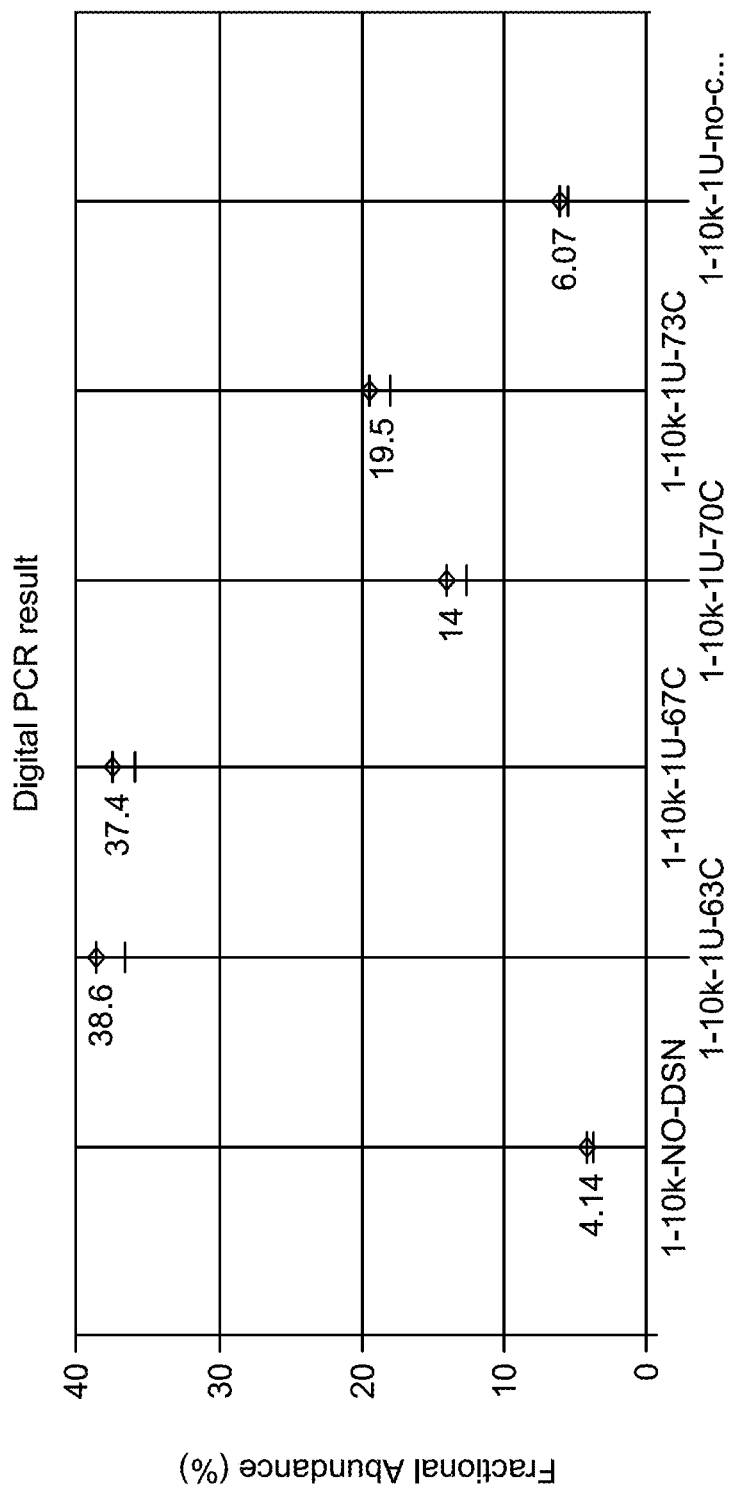
FIG. 1B shows the validation of NaME-based mutation enrichment as described in FIG. 1A via digital PCR (ddPCR) for a mutated KRAS amplicon with 5% original mutation abundance (mutation abundance=fractional ratio of mutant to wild-type DNA, expressed as a percentage). In this example, the DNA did not undergo a 95° C. denaturation step; the DNA, two probes, and DSN were mixed and the temperature was elevated (67° C.) to de-stabilize the duplex and enable probe binding. A range of temperatures was applied to identify the optimal temperatures for WT-specific digestion. Following DSN action, the DSN was inactivated via heating at 95° C. and droplet digital PCR (ddPCR) was applied to the digested sample. ddPCR quantifies the mutation enrichment achieved by measuring fractional mutation abundance before and after DSN action.

In this method, DSN is, optionally, not added from the beginning in order to avoid partial or total inactivation of the DSN at the denaturing temperature. DSN is added once the temperature is reduced to allow formation of complimentary wild type—probe duplexes on top and bottom strands and partially complimentary mutant-probe duplexes. DSN then preferentially degrades the complimentary wild type-probe duplexes, while the partially complimentary mutant-probe duplexes remains substantially intact. The DSN activity can then be stopped, for example, by heating the sample to 95° C. for 1-10 min to inactivate the DSN. A subsequent PCR reaction amplifies preferentially the mutated alleles that remain substantially intact, while the DSN-digested wild type alleles do not amplify. FIG. 1B demonstrates quantification of the fractional mutation abundance following this PCR reaction. It can be seen that in the absence of DSN and/or both probes the mutation abundance is low (4-6%) while in the presence of DSN and both probes the resulting mutation abundance is 37-38%, i.e. demonstrating the enrichment of the mutated alleles using NaME.

In some embodiments, the subsequent PCR reaction amplifies the probes rather than the hybridized nucleic acid. In this approach, a purification step is applied following probe binding to top-and-bottom DNA target strands, either before or after DSN cleavage, to remove excess unbound probes (e.g., using a DNA affinity column, such as QIAquick® PCR purification kit commercially available from QIAGEN). Then following DSN cleavage the uncut probes are amplified (instead of amplifying the target DNA) and identified/quantified. Since probes that bind WT DNA will have been selectively digested by DSN, the presence of any given probe after amplification indicates a mutation under the region covered by this probe.

NaME Using Overlapping Probes

Figure 2:
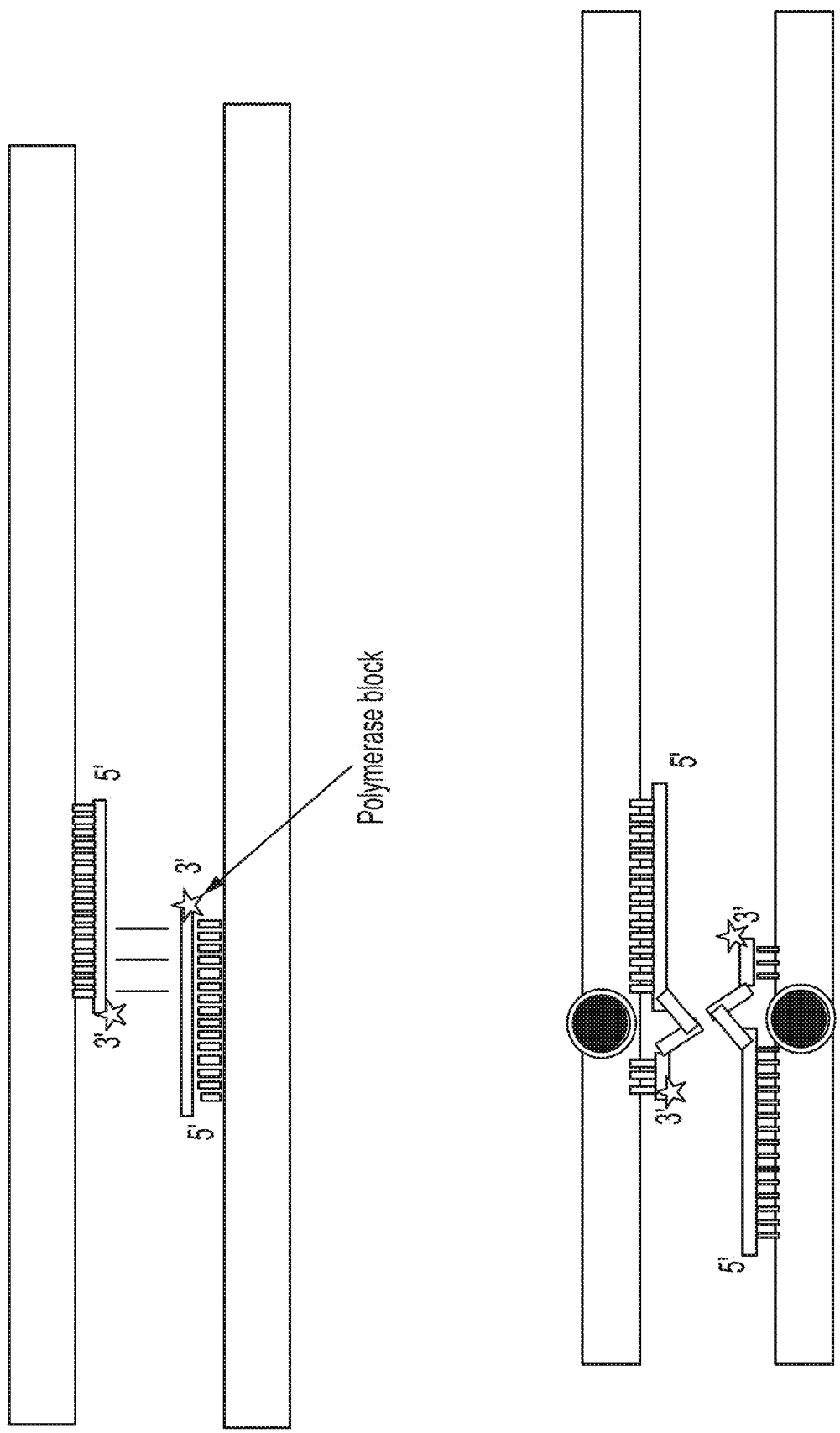
FIG. 2 is a schematic showing the use of partially overlapping probes to provide selectivity simultaneously on both DNA strands when binding a mutation. Probes are preferably 3'-blocked to prevent subsequent polymerase extension.
Figure 3:
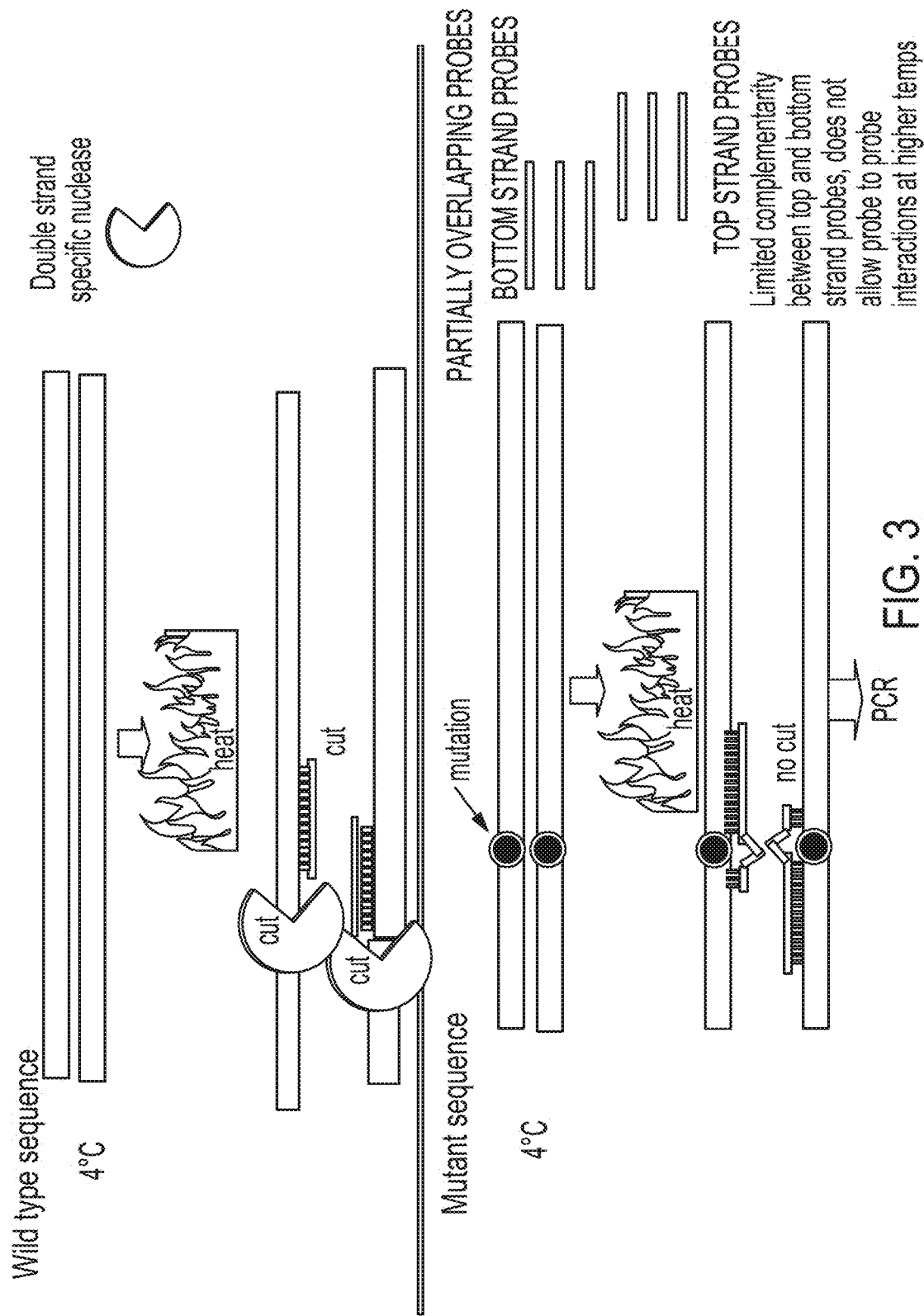
FIG. 3 is a schematic showing the use of duplex specific nuclease and partially overlapping sequence selective oligonucleotides to enable the selective degradation of double-stranded, or denatured, DNA. With the mutant sequence, there is limited complementarity between the top and bottom strand probes, which prohibits probe-to-probe interactions at higher temperatures.

In some embodiments of the methods described herein, the probes are constructed such that one of the probes overlaps a sequence on the top strand of the target nucleic acid containing the mutation, while the other probe overlaps a sequence on the bottom strand of the target nucleic acid containing the mutation of interest and the two probes partially overlap each other (FIGS. 2 and 3). The two probes overlap only partially, so that they do not bind substantially to each other in solution at the temperatures used for NaME during DSN digestion (e.g., 65° C.-70° C.). Accordingly, it is important during probe hybridization to their corresponding sequences to retain a temperature low enough for probe binding to the template, but high enough so that it does not allow substantial probe-to-probe binding. This approach increases the specificity of the process for mutated sequences, and the mutation enrichment becomes much more pronounced than when using only one mutation-specific probe with a second probe which matches the wild-type nucleic acid (FIG. 1A).

In some embodiments, a thermostable DSN, such as but not limited to, king crab nuclease is used in the methods described herein. In some embodiments, a non-thermostable DSN, such as but not limited to, native shrimp dsDNase, recombinant shrimp dsDNase, and bovine DNase I is used in the methods described herein. If a non-thermostable DSN is used during NaME, then the overlap between the probes designed must be such that at the temperature used for probe-nucleic acid duplex formation (e.g., 37-45° C. there is minimal binding of the probes to each other, while they still bind specifically to genomic DNA targets). One way to reduce the Tm of the probes to match the optimal temperature of the nuclease used is to add organic solvents (DMSO, formamide) that lower the Tm of the probes. For example, instead of probes with a Tm of 65° C. matching the optimal temperature of thermostable DSN enzyme, one may use shrimp nuclease in the presence of 10% DMSO which reduces the probe Tm as well as the Tm of probe-probe overlap regions.

For the purposes of the present disclosure, the term "double-strand specific nuclease" or "DSN" includes DNA/RNA guided enzymes which have preferential activity on double-stranded DNA, as opposed to single stranded DNA. Examples of such enzymes that can be employed in conjunction with NaME include the RNA-guided Cas9 enzymes (Gu et al, *Depletion of Abundant Sequences by Hybridization (DASH): Using Cas9 to remove unwanted high-abundance species in sequencing libraries* and *molecular counting applications* Genome Biology 2016; 17, 41), or the Argonaute DNA-guided enzymes (Gao et al, *DNA-guided genome editing using the Natronobacterium gregoryi Argonaute*, Nature Biotechnology May 2016 advanced online publication). These DNA/RNA guided enzymes digest DNA with high preference when the probe ('guide oligonucleotide') is fully matched to the target DNA, and less so when there is a mismatch. By employing probes targeting both top and bottom DNA strands in an overlapping fashion as described in the present invention, NAME can be applied with DNA/RNA guided enzymes, in the same manner as when using other DSN nucleases described herein.

In some embodiments, prior to implementing the methods described herein, the nucleic acid sample is subjected to an amplification condition. In some embodiments, the methods described herein further comprise enriching the target mutant nucleic acid relative to the wild type nucleic acid by subjecting the reaction mixture containing cleaved wild type-probe duplexes and uncleaved target mutant nucleic acids to an amplification condition thereby enriching the uncleaved target mutant nucleic acid relative to the cleaved wild type nucleic acid. Any known amplification condition can be used. In some embodiments, the amplification condition is selected from the group consisting of: PCR, ligation mediated PCR using common ligated adaptors, multiplex PCR, using multiple pairs of primers, PCR of repeat elements using primers specific for ALU, LINE 1, poly-nucleotide repeats, micro-satellites and other repeat elements spread over the genome, arbitrarily-primed PCR (AP-PCR) and isothermal amplification (such as but not limited to displacement amplification based on phi-29 based; or Loop Mediated LAMP amplification; or any other iso-thermal mode of amplification). The wild type nucleic acid will not amplify during this amplification step since it was cleaved selectively by DSN. The mutation-enriched amplified product can then be analyzed for mutations using any available method such as MALDI-TOF, HR-Melting, Di-deoxy-sequencing, Single-molecule sequencing, massively parallel sequencing (MPS), pyrosequencing, single strand conformational polymorphism SSCP, restriction fragment length polymorphism RFLP, denaturing high precision liquid chromatography dHPLC, chemical cleavage of mismatches CCM, capillary electrophoresis, digital PCR and quantitative-PCR.

The probes used in the methods described herein preferably contain a 3'-block to polymerase extension, so that if the NaME-reaction product is subsequently amplified there is no interference of the probes with the amplification reaction. A 3'-polymerase block can comprise a simple phosphate; or abasic site; or any other modification that prevents polymerase synthesis past the block. In addition, for added discrimination of wild type versus mutant sequences during NaME, in some embodiments, each probe comprises a locked nucleic acid (LNA), peptide nucleic acid (PNA), xeno nucleic acid (XNA), nucleic acid with any known natural or modified base such as dITP or 2,6-diaminopurine dATP or RNA that increases the destabilization caused by a mutation-induced mismatch between the oligonucleotide probe and its target nucleic acid.

In some cases part of the probes used in the methods provided herein can comprise one or more random nucleotides, so that the probe can be directed against a plurality of DNA targets. For example, a probe can include a core region of one or more nucleotides which are complimentary to the wild-type nucleic acid sequence in a region of interest. e.g., a suspected mutation site. Any one or more of the remaining nucleotides in the probe may be selected randomly from any or all possible nucleotides. The probe containing the core region plus one or more random nucleotides can form a duplex with a fully complimentary wild-type nucleic acid sequence which also contains the core region. A cleavage enzyme, e.g., DSN, can be used to cleave the complimentary wild-type probe duplexes, but not the partially complimentary target mutant-probe duplexes.

In some embodiments, the methods described herein are used to prepare two or more different target mutant nucleic acids for subsequent enrichment relative to corresponding wild type nucleic acids. In such embodiments, one or more additional pairs of probes directed to the different wild type nucleic acids are used. For each pair of probes, one of the probes is complimentary to the wild type nucleic acid top strand, while the other is complimentary to the wild type nucleic acid bottom strand.

In all embodiments described above, it is also understood that the concentration of probes for the top and bottom DNA strands does not necessarily need be the same. Thus one may combine a high concentration of probe for the bottom strand and a low concentration of probe for the top strand, or vice versa. Probe concentrations can also be different for each DNA target when many targets are simultaneously enriched. Optimized concentrations depending on sequence context, local sequence Tm and mutation being targeted can be applied. Furthermore a subsequent PCR amplification reaction following application of DSN can utilize equal amounts of primers or different amounts of primers for each DNA strand (asymmetric PCR, or Linear After The Exponential, L.A.T.E PCR).

NaME Applied Directly on Genomic DNA

Figure 4:
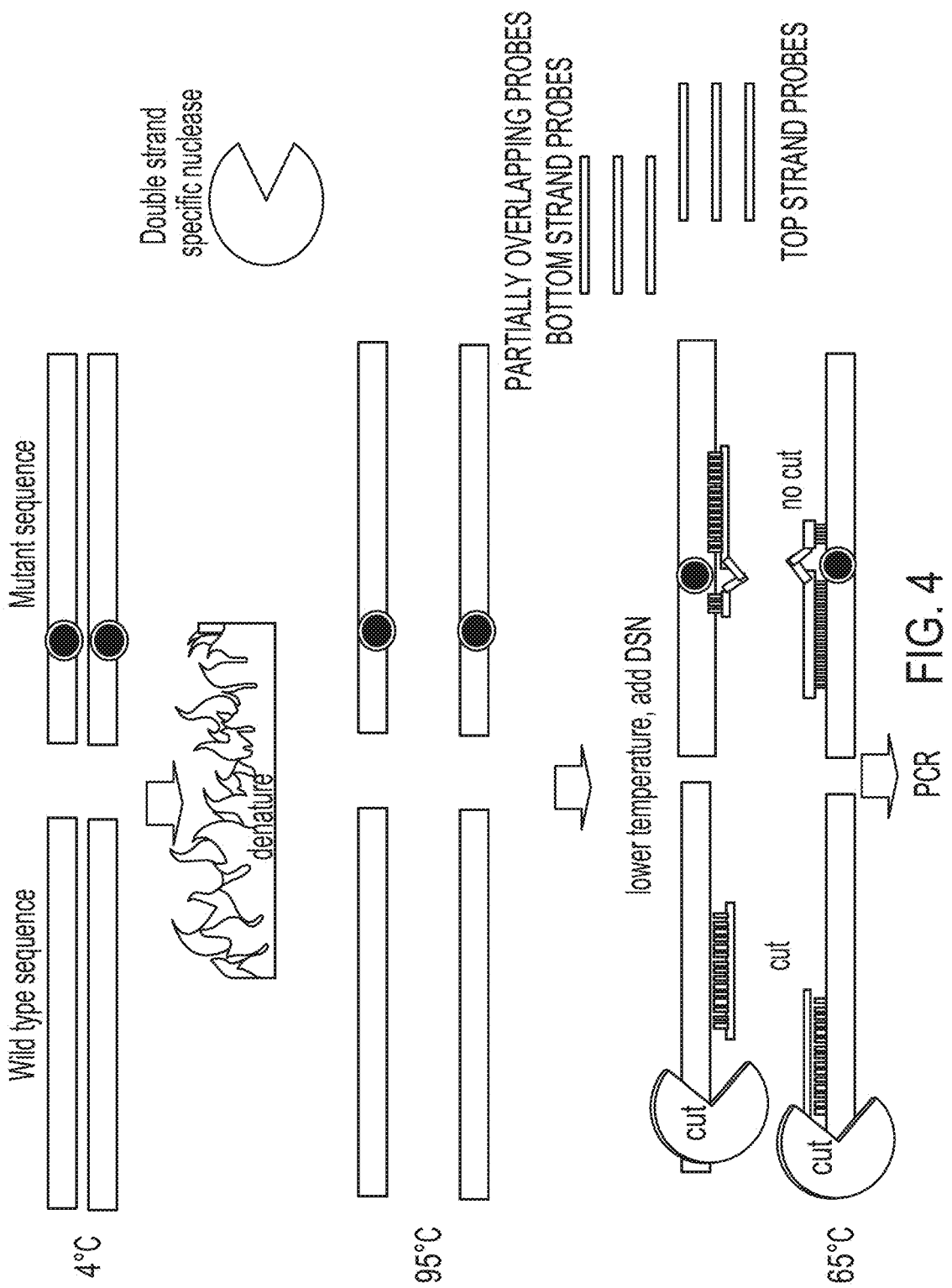
FIG. 4 is a schematic showing wild-type allele degradation directly from fragmented genomic DNA (i.e. not pre-amplified DNA). Note that a multiplex approach can be taken; thousands of probes can be used simultaneously on selected DNA targets of interest.

In some embodiments, the methods described herein are performed directly on genomic DNA. The genomic DNA can optionally be fragmented prior to application of NaME (FIG. 4). In this approach, NaME is applied by (a) fragmenting the genomic DNA using enzymatic or physical means; (b) adding overlapping (or non-overlapping) probes that address both top and bottom DNA strands and optionally denaturing both the wild type and target nucleic acids (for example, at 95° C.); (c) reducing the temperature to, for example, 60-70° C. to enable probes to find their respective targets prior to substantial renaturation of the parent DNA strands, and keeping the temperature high enough to minimize probe-to-probe interactions; (d) adding DSN to selectively cleave one or more (multiple) complimentary wild type-probe duplexes DNA targets while leaving the partially complimentary target mutant-probe duplexes substantially intact. The resulting reaction mixture with cleaved wild type-probe duplexes and uncleaved target mutant nucleic acids can be amplified using methods known in the art, such as but not limited to, PCR, COLD-PCR, ligation-mediated PCR or COLD-PCR using common ligated adaptors, multiplex-PCR or isothermal amplification (such as phi-29 based; or LAMP-based; or any other isothermal mode of amplification) thereby enriching the target mutant nucleic acid as compared to the wild type. This amplified product can be examined for mutations using any available method, such as but not limited to, MALDI-TOF, HR-Melting, Di-deoxy-sequencing, Single-molecule sequencing, massively parallel sequencing (MPS), pyrosequencing, SSCP, RFLP, dHPLC, CCM, digital PCR and quantitative-PCR (the wild type nucleic acid will not amplify during this amplification step since it was selectively cleaved by DSN).

Figure 5:
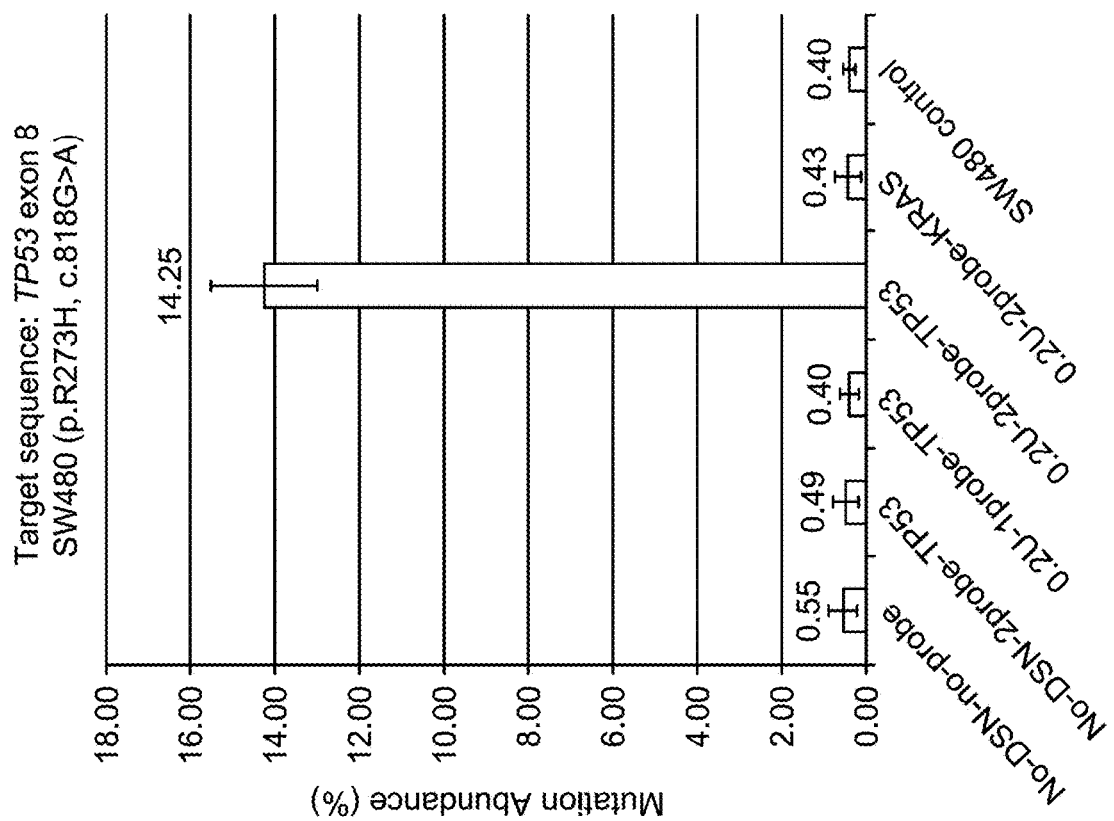
FIG. 5 shows the results of a single-plex assay showing the major increase in mutation abundance of mutational sequences following a DSN reaction directly on fragmented genomic DNA for a selected TP53 exon 8 target sequence. The mutation abundance is quantified before and after treatment of the sample with DSN, using ddPCR. The mutation abundance increases only if both top and bottom probes are included in the reaction, in addition to DSN nuclease.
Figure 5:
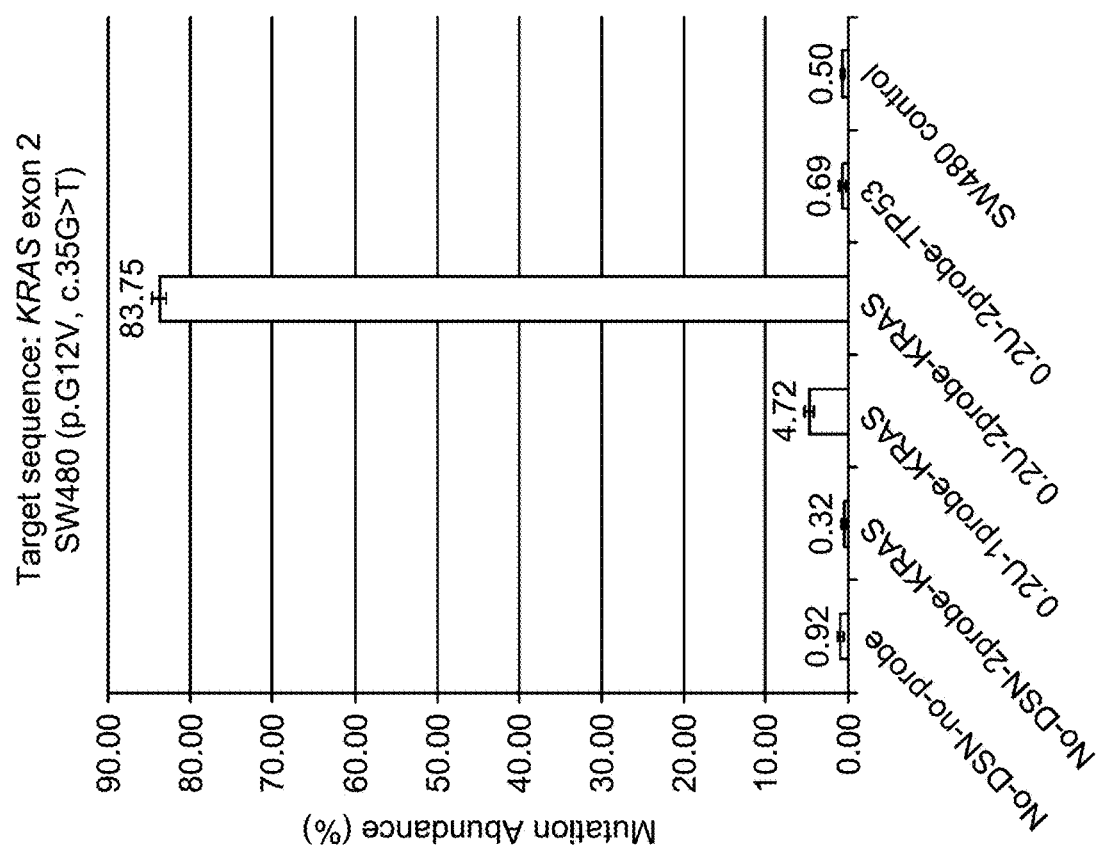
Figure 6:
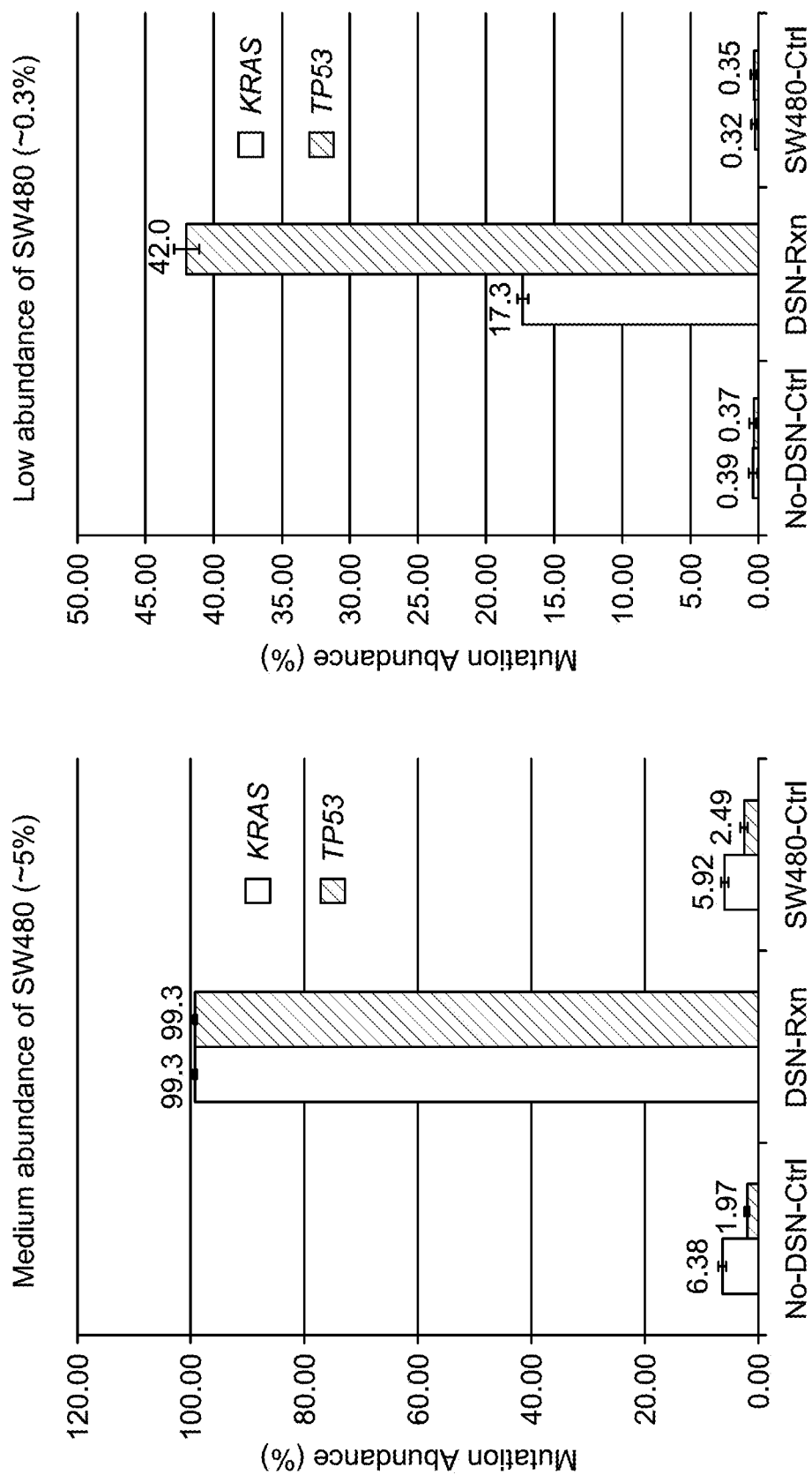
FIG. 6 shows the results of a duplex assay, showing the mutation abundance of a sample containing mutated KRAS and p53 at 5% or 0.3% original abundance, following a DSN reaction directly on fragmented genomic DNA.
Figure 7A:
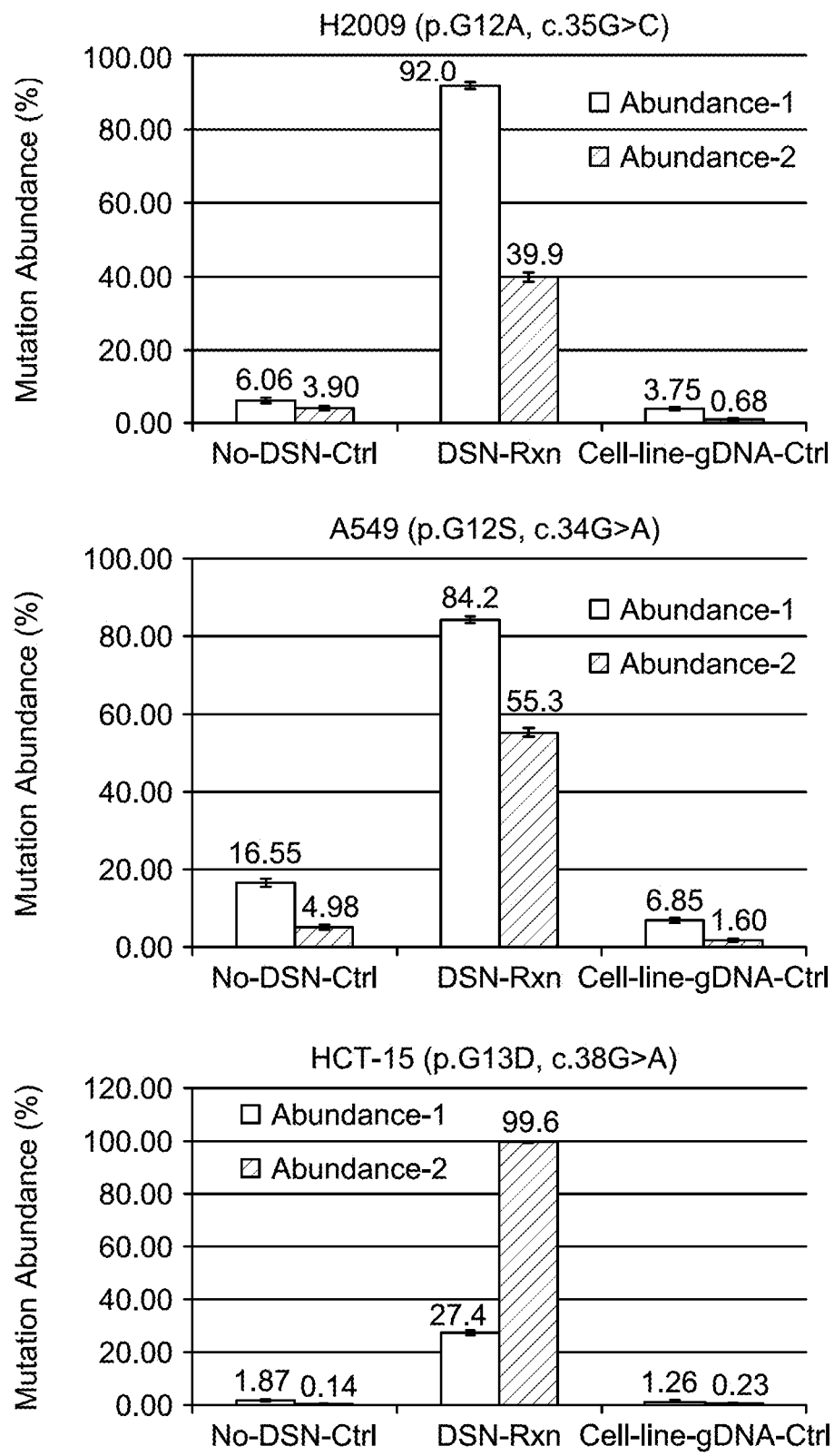
FIG. 7A shows the results of a DSN reaction on genomic DNA for a single-plex assay using DNA mutated at three different positions on KRAS exon 2 in three different cell lines: H2009, A549, and HCT-15.

FIG. 5 depicts the enrichment of an original ~1% mutation to an 83% mutation and a 0.5% mutation to 14% mutation, following application of NaME directly to genomic DNA. FIG. 6 shows a duplex application of NaME on two mutated targets simultaneously, in KRAS and TP53 genes. FIG. 7A shows application of NaME using two overlapping probes covering 3 different mutations in codons 12 and 13 of Kras, and indicating that any mutation under the probes will be enriched during NaME. And FIG. 7B demonstrates simultaneous enrichment of 11 different targets when NaME is applied directly from genomic DNA. For each target, a separate pair of overlapping probes was designed, and all probes are included in a single reaction during NaME.

In some embodiments the probes used are directed against poly-nucleotide repeats that are widespread around the genome, so that multiple targets are addressed via NaME simultaneously, using a single pair of probes. For example, if the target is a poly-A-containing sequence, two overlapping probes are used, one for bottom strand containing poly-T and one for top strand containing poly-A in this case. To increase the length of the probe, one may also add an optional number of inosines that can generically bind to neighboring bases.

Combination of NaME with Massively Parallel Sequencing (MPS).

Figure 8:
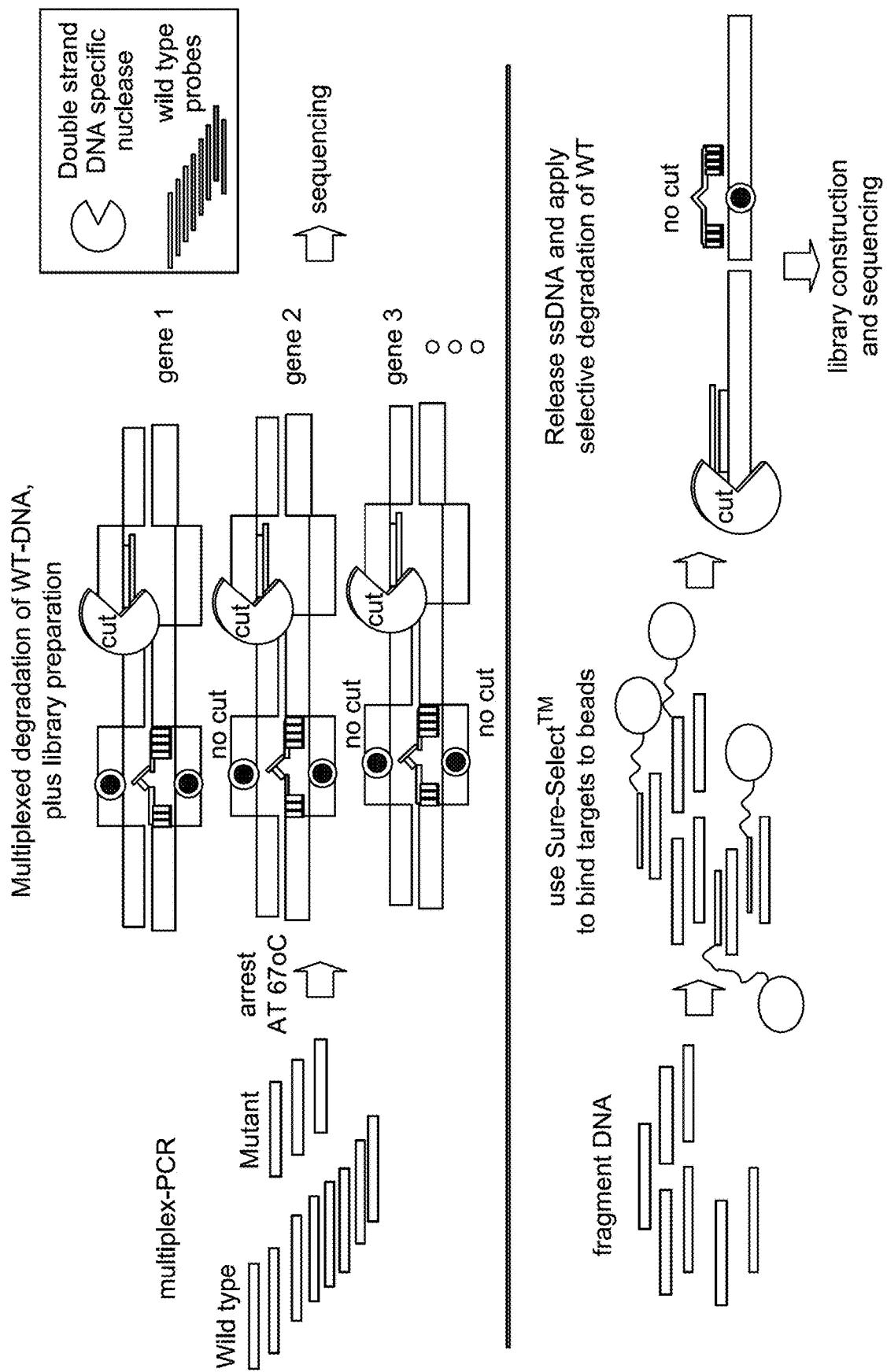
FIG. 8 is a schematic illustrating two approaches to selective degradation of wild-type DNA prior to targeted re-sequencing: one after multiplexed PCR (top), and one prior to PCR (bottom) using selective binding of DNA targets to beads. In the latter situation, the probes utilized are designed to be partially overlapping each other and bind both top and bottom DNA target strands. In addition, they are biotinylated. These probes are first used without DSN to bind their targets and to immobilize selected DNA targets to beads. The non-immobilized DNA is then removed from the solution. The temperature then is then adjusted accordingly, and NaME is applied as described above.

In some embodiments, the methods described herein may be used in conjunction with massively parallel sequencing (MPS). MPS is currently the most advanced approach for mutation identification. Sample ('library') preparation for MPS is a very important step prior to applying genome-wide or exome-wide sequencing or targeted re-sequencing. NaME provides a unique advantage for sample preparation prior to MPS, as it can enrich predictably numerous targets for mutations, thereby enabling MPS to identify easily mutations that are originally at very low abundance, without requiring an excessive number of sequence reads. This enables cost reduction and increased sensitivity and simplicity. FIG. 8 provides an example of NaME—enhanced sample preparation process prior to MPS. In this approach, multiplexed NaME (using overlapping probes against numerous gene mutations simultaneously as described in previous sections) is applied to the original starting material in order to cleave selectively wild type nucleic acid on all targets of interest simultaneously. The sample is then amplified to enrich preferentially the mutated DNA targets. Finally, the resulting mutation-enriched DNA is used for routine library construction prior to MPS.

In some embodiments, multiplexed application of NaME on numerous targets of interest can be applied directly from denatured genomic DNA as described in FIG. 4. Following this, a multiplexed PCR can be applied using primers addressing the DNA targets of interest (for example, but not limited to, the primers used in the Life-Technologies Ampliseq kit, or the Illumina Trueseq kit.). The multiplexed PCR products will now be enriched for mutations in view of the NaME treatment, thus the resulting library preparation will provide mutation enriched DNA for targeted re-sequencing.

In some embodiments, prior to implementing the NaME method described herein, targets of interest are captured from genomic DNA within molecular inversion probes (MIPS); or using the 'bait' oligonucleotides approach. In some embodiments, the MIPS or the bait oligonucleotides are biotinylated (e.g., similar to those included in the Agilent SureSelect™ kit, but re-designed to capture both top and bottom target DNA strands as per previous sections). In some embodiments, the bait oligonucleotides are attached to beads. The nucleic acid sample is contacted with the bait oligonucleotides that bind to selected targets of interest and binding of the bait oligonucleotides to the targets of interest is enabled. Next the bait oligonucleotides with the regions of interest bound thereto are isolated from the remaining nucleic acids. Finally, the isolated targets are released from beads and multiplexed NaME (using overlapping probes addressing both top and bottom DNA strands and annealing to numerous targeted gene mutations simultaneously) is used to cleave the different wild type nucleic acids simultaneously. Following this, PCR and library construction using the mutation-enriched sample can be used prior to MPS.

In some embodiments, the probe oligonucleotides that can be used in the methods described herein systematically tile a genomic region of interest, for example, chromosome Y. In some embodiments, degenerate oligonucleotide probes are synthesized that cover all AT-rich regions, all GC rich regions, gene promoters; or CpG islands. Any genomic fraction of interest can be targeted for selective cleavage 'at will' using multiple overlapping probes targeting both top and bottom strands and designed as described herein.

Mutation Enrichment Using NaME in the Absence of Subsequent Amplification.

In all embodiments described thus far, in order to produce a sample with enriched mutated target sequences, an amplification step is conducted following application of DSN digestion of the wild type DNA alleles. Alternatively, another way to enrich the mutated target sequences is to eliminate the wild type sequences (without amplification). Thus, in some embodiments, the reaction mixture with cleaved wild type-probe duplexes and uncleaved target mutant nucleic acids is subjected to a further DNA degradation condition which hydrolyzes enzymatically the DSN-cleaved wild type-probe duplexes, with the degradation initiated at the position of the cleavage. The "DNA degradation condition" includes contacting the reaction mixture with cleaved wild type-probe duplexes and uncleaved target mutant nucleic acids to an exonuclease (e.g., using exo I or exo III or Klenow fragment of *E. coli* DNA polymerase I that digest DNA from the 3'-end) under conditions of optimal exonuclease activity (that is, the temperature, pH ion concentrations etc. are maintained to provide optimal enzyme activity).

In this approach, genomic DNA can either be not fragmented, or it may be randomly fragmented as described in preceding sections. If the DNA is fragmented, the fragmented genomic DNA is first ligated to adaptors that are resistant to 3'-exonuclease digestion (e.g., by using adaptors that have a 3'-terminal phosphorothioate linkage). Next, the DNA sample is denatured and NaME is applied as described in previous sections to generate cleavage of wild type sequences while leaving intact the mutated sequences. Next, an exonuclease digestion is applied (e.g., using exo I or exo III or Klenow fragment of *E. coli* DNA polymerase I that digest DNA from the 3'-end). Exonuclease will digest all sequences that do not have an exonuclease resistant 3'-end, i.e. without 3'-terminal phosphorothioate. Since DSN-nicked fragments do not have a 3'-terminal phosphorothioate, they will be fully digested by the enzyme, thereby eliminating wild type DNA strands. Digestion will proceed from the 3'-position of the DSN-induced nick all the way to the 5'end, while leaving the (un-nicked) mutated target sequences intact. Optionally, one may also digest wild-type sequences from the 5'-end of the nick all the way to the 3'-end by using *E. coli* DNA polymerase I that has 5' to 3' exonuclease activity. Following the complete digestion of the DSN-nicked, wild type sequences, an endpoint detection method that does not require amplification, such as a single molecule sequencing approach (Nanopore system; or Pacific-Bio system) can be used to sequence the mutation-enriched DNA sample. This embodiment that does not rely on any form of nucleic acid amplification and can be particularly useful in the sequencing of small genomes (e.g., bacterial or viral genomes) where low level mutations are currently difficult to detect in view of the relatively high error rate of these sequencing systems. The approach can be combined with selective capture of genomic fragments on beads, to reduce the complexity of a larger genome followed by NaME to eliminate wild type DNA and enrich mutated target sequences in the absence of amplification.

Mutation Scanning Using NaME

Figure 12A:
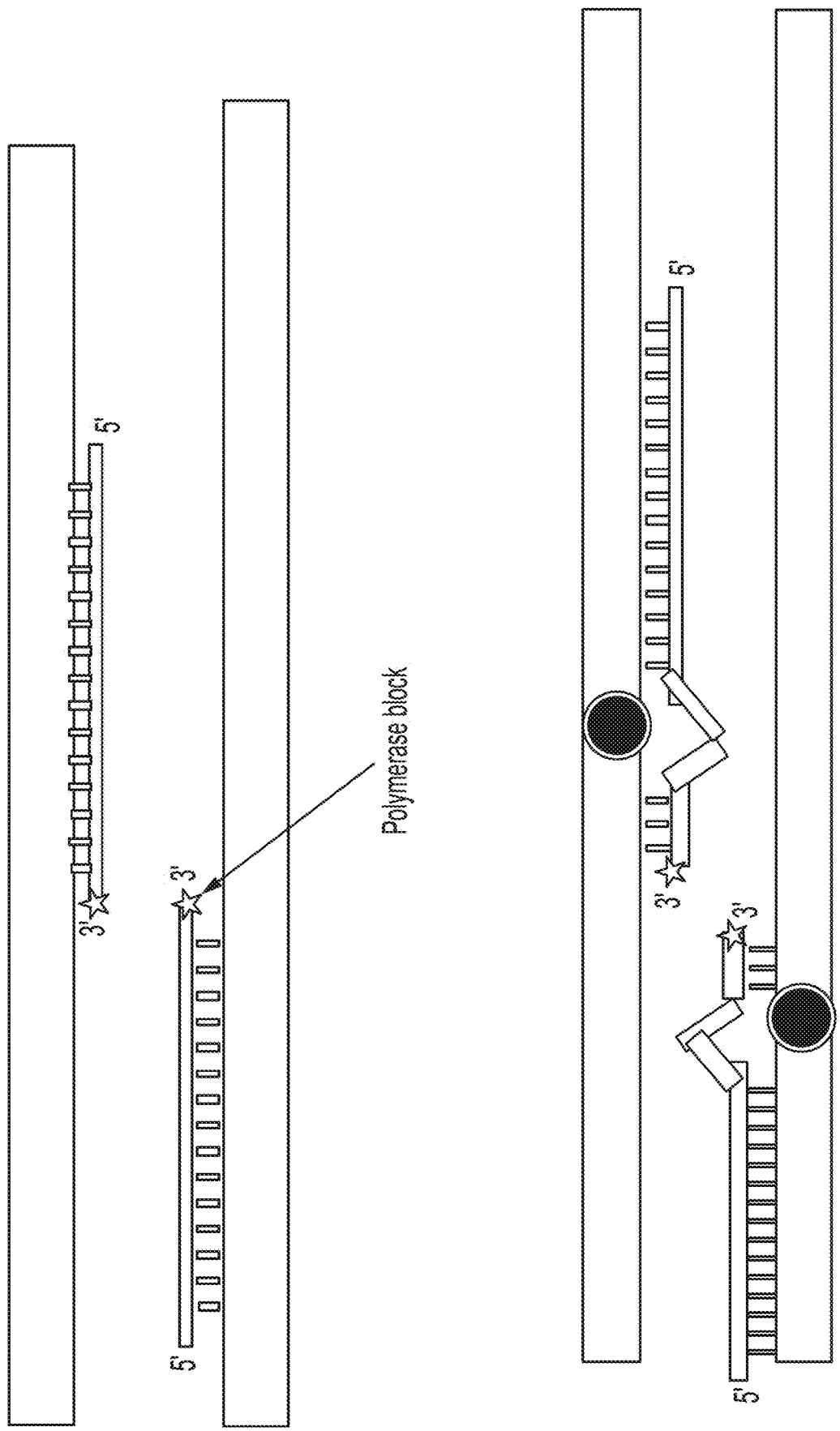
FIG. 12A is schematic illustrating mutation scanning using two or more longer (non-overlapping) probes on opposite strands. Probes are preferentially 3'-blocked to prevent polymerase extension, and may contain modified bases, such as LNA, PNA, XNA, deoxy-inosine triphosphate (dITP), or contain dUTP, or comprise RNA. In some cases part of the probes can comprise one or more random nucleotides, so that the probe can be directed against a plurality of DNA targets. The total combined sequence under the two probes is interrogated during NaME: if there is a mutation anywhere under the two probes, it will prevent strand cutting.
Figure 12B:
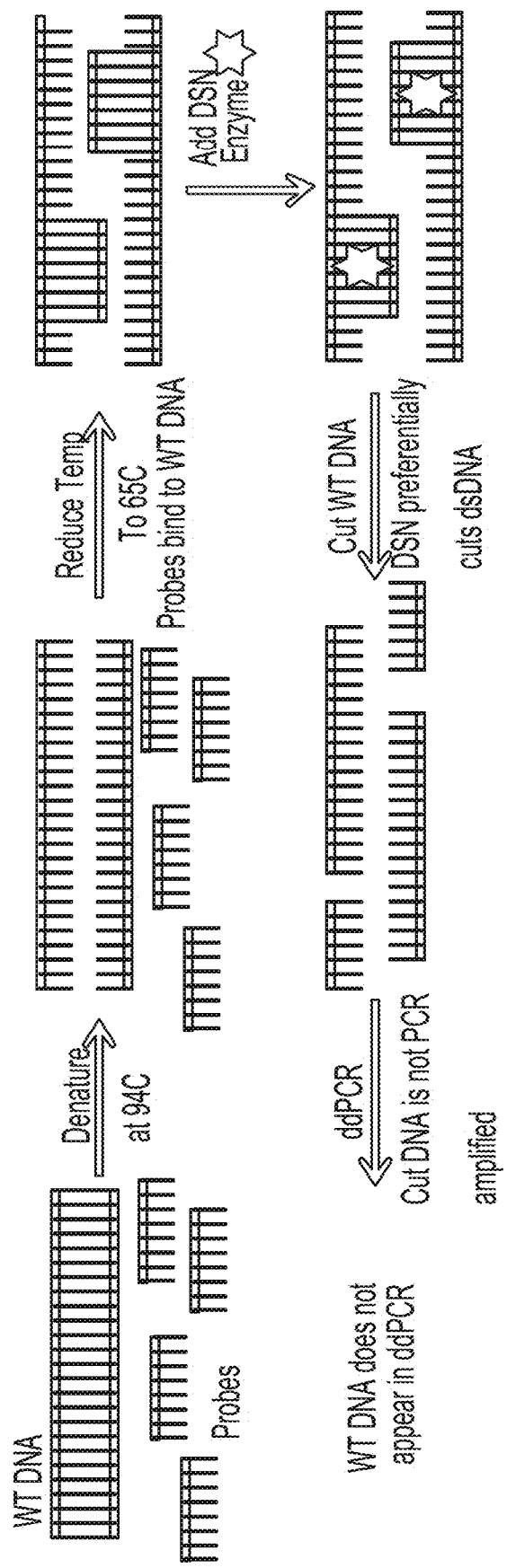
FIGS. 12B-12C show that the combination of denaturation and DSN for mutation scanning as described in 12A results in the preferential cutting of wild-type DNA. A mutation present anywhere under the two probes results in the amplification of the mutated DNA during subsequent PCR or digital PCR. The effects of probe length and concentration on mutation enrichment are depicted in the graphs.
Figure 12C:
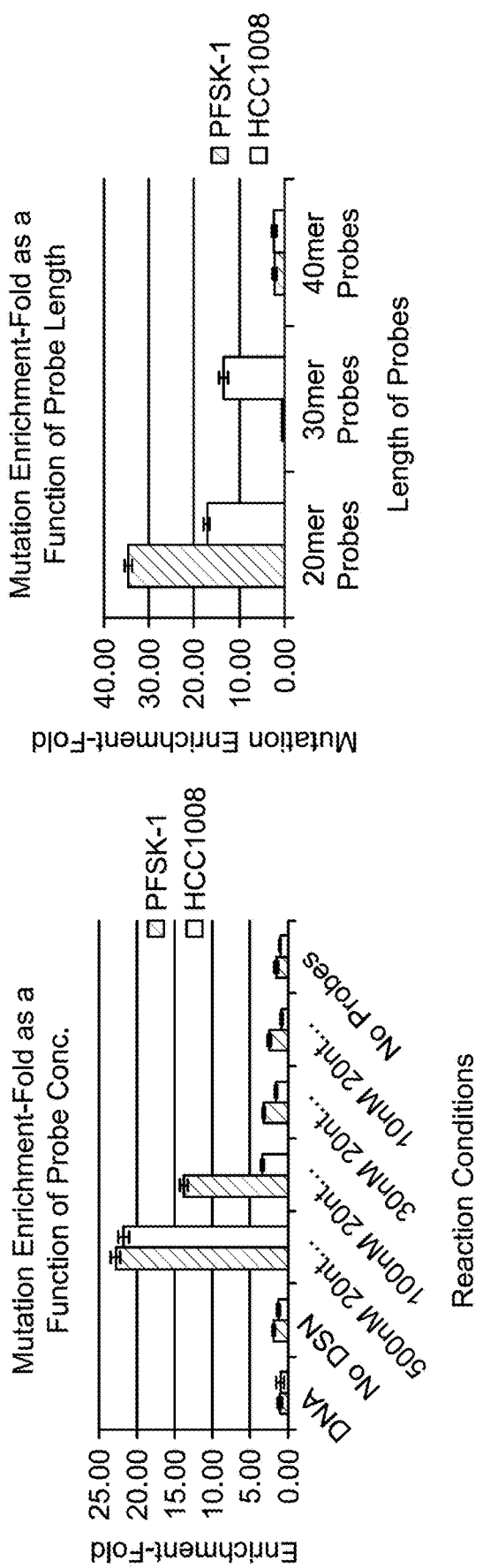
Figure 12D:
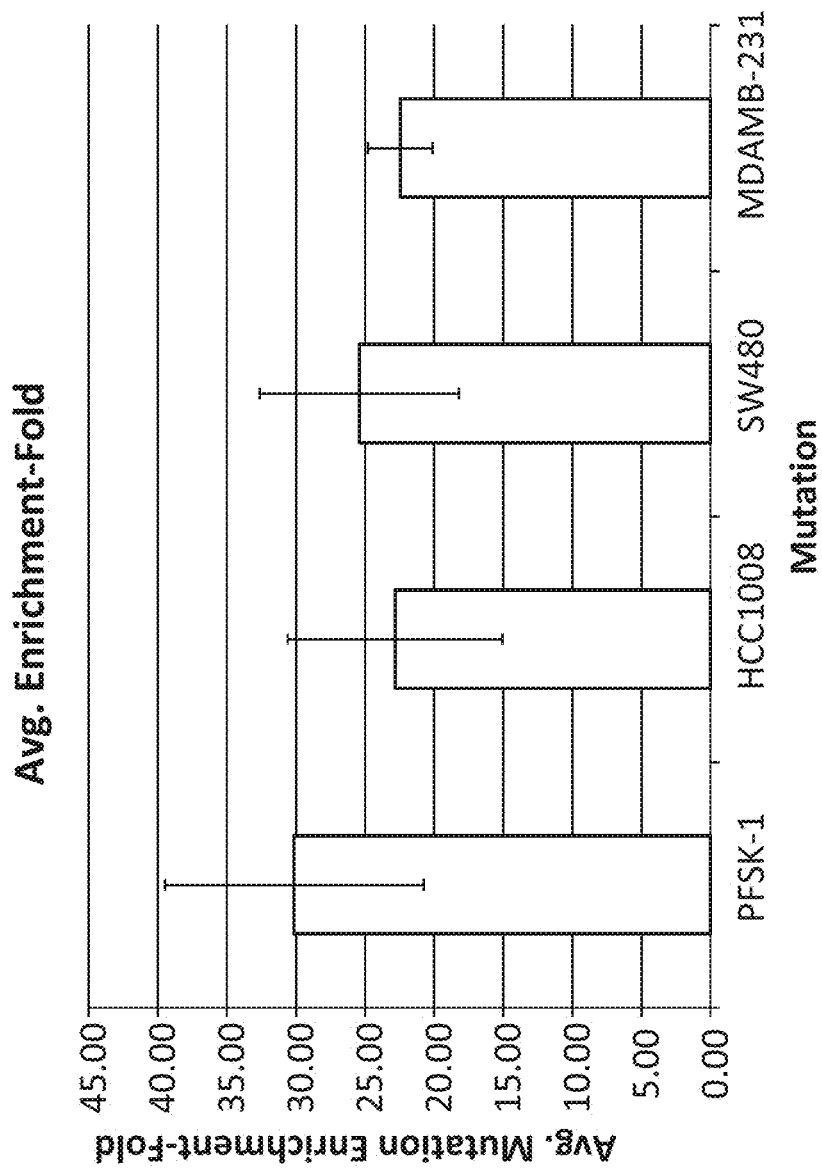
FIG. 12D shows mutation scanning using two adjacent probes and DSN in NaME as described in 12A. The graph presents the average mutation enrichment-fold of each listed mutation.

Often there is a need to scan for mutations in long DNA regions (as opposed to identifying known mutations at a single hotspot position, such as KRAS). Using two longer probes that are complementary to adjacent DNA sequences (one probe on bottom strand and the second, adjacent probe, on the top strand) one can adapt NaME for 'mutation scanning'. For example, probes of 50-70 bp can be used to cover a region of 100-140 base pairs. If there is a mutation at any position along these 140 base pairs, the corresponding strand will not be substantially cleaved by DSN. Hence, the mutant strand will survive and will lead to a subsequent PCR product that can be sequenced (FIG. 12A). In this way, longer regions on tumor suppressor genes like p53 can be enriched for mutations irrespective of the mutation position (FIGS. 12B and 12C).

NaME Application with RNA or ssDNA

Figure 13:
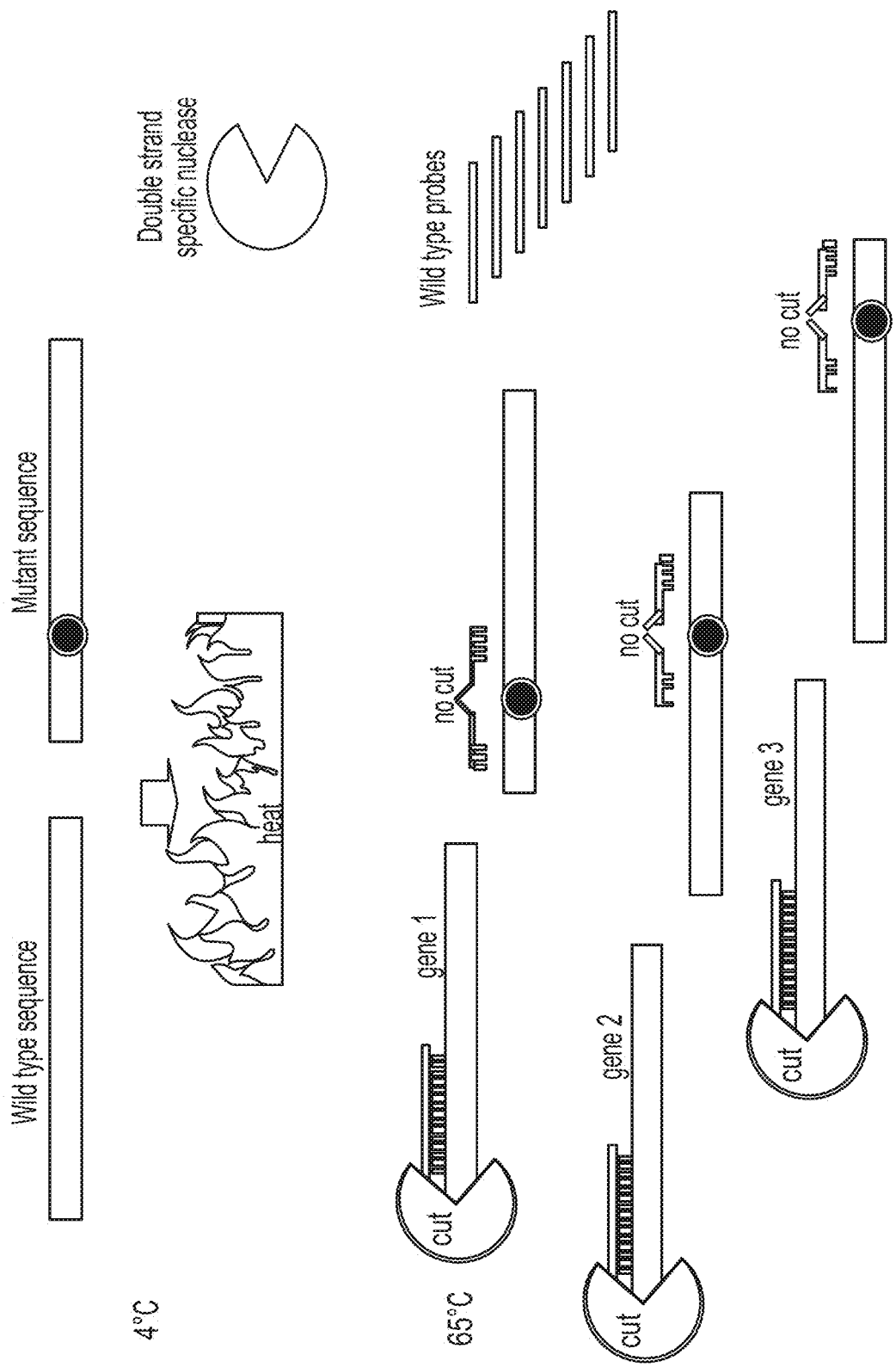
FIG. 13 is a schematic representing the application of NaME with RNA or single-stranded DNA. Multiplexed wild-type nucleic acid degradation is used to enrich mutants prior to cDNA synthesis or PCR.

In some embodiments, the methods described herein can be used to selectively cleave wild type cDNA, or mRNA or DNA in single stranded format. For this approach (FIG. 13), only a single probe per targeted gene would be needed, as opposed to one probe on each opposite strand used in dsDNA.

Methylation-Sensitive NaME (with Probes)

Figure 14:
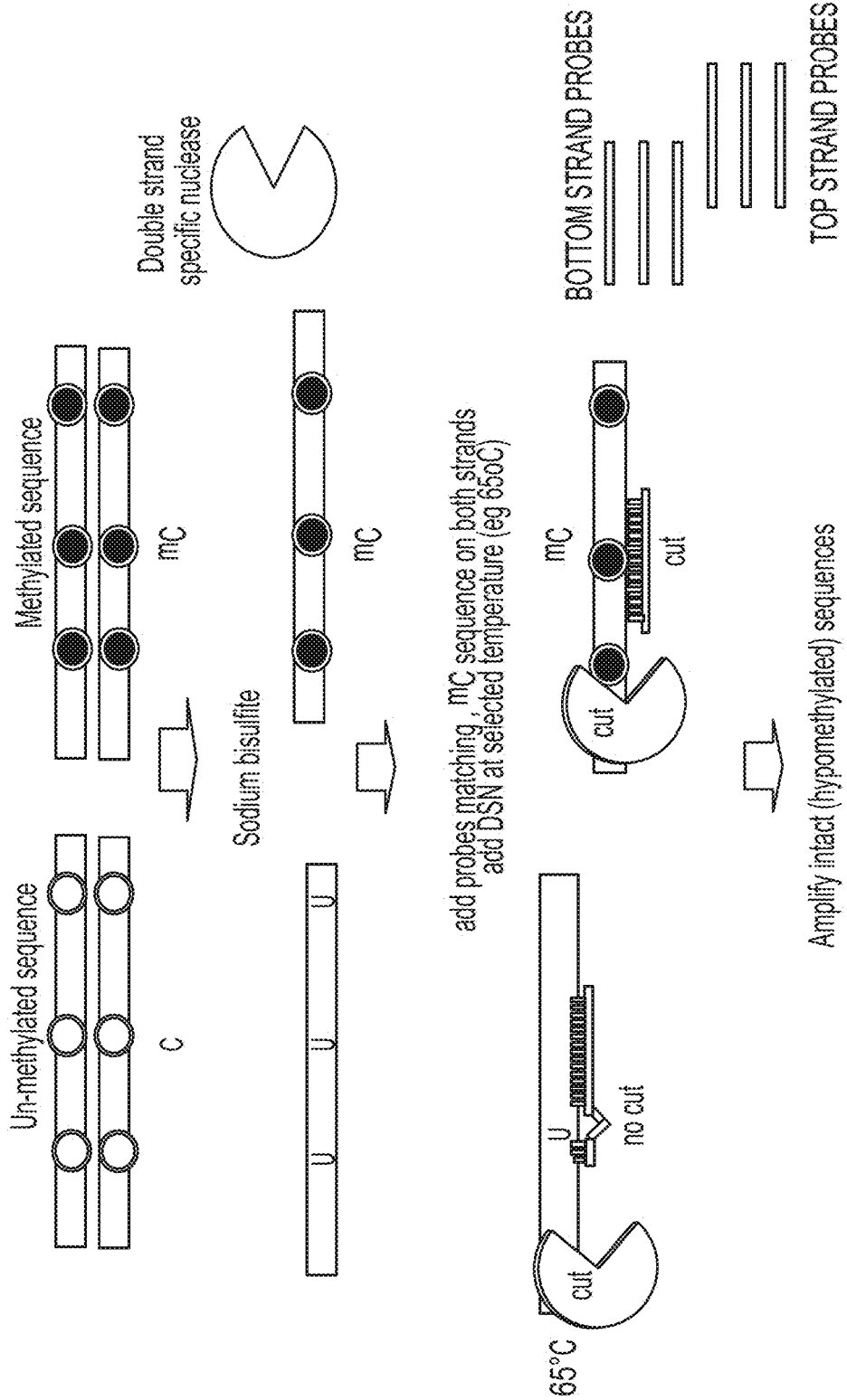
FIG. 14 is a schematic showing hypomethylation enrichment from fragmented genomic DNA using probes designed to match the methylated alleles on the target sequences.

In some embodiments, the methods described herein are used to prepare an unmethylated target nucleic acid of interest for subsequent enrichment. In such embodiments, prior to implementing NaME on the reaction mixture, the nucleic acid sample is treated with sodium bisulfite (bisulfite converts all cytosines to uracils, unless the cytosines are methylated at CpG dinucleotide positions). The pair of oligonucleotide probes used in these methods are complimentary to top and bottom strands of the methylated nucleic acid of interest, that is, one of the oligonucleotide probes is complimentary to top strand of the methylated nucleic acid of interest, while the other oligonucleotide probe is complimentary to the bottom strand of the methylated nucleic acid of interest following bisulfite conversion. The probes will, thus, form complimentary (i.e., without any mismatches) duplexes with the top and bottom strands in alleles that contain fully methylated DNA. In contrast, the probes will form partially complimentary duplexes with the alleles containing unmethylated cytosines because of mismatches at the positions of uracils (which used to be cytosines before bisulfite conversion). As a result, the methylated duplexes will be cleaved by DSN, while the unmethylated duplexes will remain substantially intact for subsequent amplification (FIG. 14).

Since NaME works well with mismatches caused by single point mutations, it can be expected that presence of several mismatches on a sequence due to conversion of multiple cytosines makes DSN match/mismatch discrimination work even better. Thus, one can optionally also use probes that are longer, (for example, 50-200 bp or longer) with this approach. Furthermore, in contrast to regular double stranded DNA, bisulfite converted DNA remains single stranded after chemical treatment, and the two DNA strands are not complementary to each other any longer. Accordingly, one may optionally use probes matching only the top DNA strand, or matching only the bottom DNA strand following bisulfite conversion of DNA.

One can use thousands of probes covering all promoters and tiling entire genomic regions. For example, genomic DNA is digested into smaller fragments, using physical shearing for random fragmentation or restriction enzyme fragmentation (using enzymes that are methylation-independent). DNA is randomly fragmented, end repaired, and ligated to methylated adaptors that are resistant to bisulfite conversion. This is a standard first step in whole genome bisulfite sequencing preparations. Next, the sample is treated with sodium bisulfite, to convert unmethylated C to U (FIG. 14). The DNA at this point comprises mostly single stranded sequences. Next, the NaME procedure is applied, by adding DSN plus a large set of synthesized oligonucleotide probes designed to match the methylated bisulfite-converted version of the regions of interest (for example, an entire tumor suppressor gene like TP53 or BRCA1; or a large portion of chromosome 21 if trisomy 21 is under examination for pre-natal diagnostics; or all promoters in oncogenes; or regions that are differentially methylated among various tissues in order to assist definition of the tissue of origin when examining circulating DNA or other liquid biopsies). The probes will form perfectly double stranded DNA (i.e., complimentary duplexes) in alleles that contained fully methylated DNA. Both top and bottom strands of the original DNA need to be addressed by the oligonucleotides used, as both parent DNA strands need to be selectively digested and prevented from subsequent amplification. Alleles with unmethylated DNA will remain undigested, because the probes will contain mismatches at the positions of uracils (bisulfite converted cytosines). As a result, DSN will not cut these sequences, thereby allowing their subsequent amplification (FIG. 14). Following selective cleavage of methylated targets of interest, an amplification condition, such as PCR using the common adaptors, can be applied followed by sequencing of the sample. Alternatively on can apply PCR of repeat elements using primers specific for bisulfite-treated ALU, LINE 1 and other repeat elements spread over the genome; or arbitrarily-primed PCR (AP-PCR); or COLD-PCR. Isothermal forms of amplification may also be used in the place of PCR. This approach is of relevance to many applications such as cancer diagnosis/therapy (for detecting global hypomethylation), to prenatal diagnosis (e.g. for detecting placental DNA which contains fetal sequences that are substantially unmethylated), and to other diseases known to result/cause hypomethylation, such as systemic lupus erythymatosis.

In some embodiments, e.g., following sodium bisulfite treatment, the method is applied in the opposite manner, that is, to prepare a methylated target nucleic acid of interest for subsequent enrichment. In such embodiments, the pair of oligonucleotide probes used are fully complimentary to top and bottom strands of the unmethylated nucleic acid of interest, that is, one of the oligonucleotide probes is complimentary to top strand of the unmethylated nucleic acid of interest, while the other oligonucleotide probe is complimentary to the bottom strand of the unmethylated nucleic acid of interest following its bisulfite conversion. This results in the preferential removal of the unmethylated regions of the targets of interest.

In some embodiments, e.g., following bisulfite treatment, the method is used to prepare both an unmethylated target nucleic acid of interest and a (different) methylated target nucleic acid of interest for subsequent enrichment. The method comprises: (i) a pair of oligonucleotide probes, one of which is complimentary to top strand of the methylated form of the unmethylated target nucleic acid of interest, while the other is complimentary to the bottom strand of the methylated form of the unmethylated target nucleic acid of interest, (ii) a pair of oligonucleotide probes, one of which is complimentary to top strand of the unmethylated form of the methylated target nucleic acid of interest, while the other is complimentary to the bottom strand of the unmethylated form of the methylated target nucleic acid of interest; and wherein prior to implementing NaME protocol described herein on the reaction mixture, the nucleic acid sample is treated with sodium bisulfite.

In some embodiments, the method is used to prepare multiple target nucleic acids of interest, some of which are methylated target nucleic acids of interest, and some of which are unmethylated target nucleic acids of interest. In such embodiments, (i) a pair of oligonucleotide probes, one of which is complimentary to top strand of the methylated form of each unmethylated target nucleic acid of interest, while the other is complimentary to the bottom strand of the methylated form of each unmethylated target nucleic acid of interest, and (ii) a pair of oligonucleotide probes, one of which is complimentary to top strand of the unmethylated form of each methylated target nucleic acid of interest, while the other is complimentary to the bottom strand of the unmethylated form of each methylated target nucleic acid of interest are used. Prior to implementing NaME on the reaction mixture, the nucleic acid sample is treated with sodium bisulfite. Thus, the methods described herein allow for the simultaneously removal of (a) unmethylated promoters in tumor suppressor genes (so that it becomes easy to reveal the methylated genes of interest), and (b) methylated promoters of oncogenes (so that it becomes easy to reveal the unmethylated genes of interest). In this way one can enrich for methylated oncogene promoters, as well as for unmethylated oncogene promoters, simultaneously.

Finally, similar approaches to those described above using bisulfite treatment of DNA to selectively enrich 5-methylcytosine (5mC)-based differentially methylated/unmethylated DNA regions may also be applied to selectively enrich different epigenetic DNA modifications of interest, such as 5-hydroxy-methylation (5hmC). 5-hydroxy-methylation is an epigenetic modification functionally and biologically different from 5-methylcytosine-modification. Thus it is important to measure separately these two modifications. One way to separate DNA containing 5hmC from that containing 5mC is TAB-seq (tet-assisted bisulfite sequencing, Ito S et al, Science 2011 333(6047):1300-1303; and Yu M et al, Cell 2012: 149:1368-80). In TAB-seq, genomic 5hmC is first protected with protected by glucosylation, prior to performing bisulfite conversion. The DNA is then treated with a Tet enzyme, converting 5mC to 5caC, while leaving the glycosylated 5-hydroxy-methylation untouched. Any C's read in the resulting sequencing are thus interpreted as 5-hydroxy-methylated. Accordingly, depending on whether bisulfite treatment is applied directly, OR following glucosylation, the present invention can be directed to enriching either 5-methylcytosine-containing DNA or 5-hydroxy-methylcytosine containing DNA.

Nuclease Chain Reaction

Some aspects of the disclosure relate to a method for preparing a target mutant nucleic acid for subsequent enrichment relative to a wild type nucleic acid, using a 'chain reaction approach'. The method comprises the steps of: (a) exposing a nucleic acid sample comprising a double-stranded wild type nucleic acid and a double-stranded target nucleic acid suspected of containing a mutation to a thermostable double strand-specific nuclease (DSN) and a pair of oligonucleotide probes, one of which is complimentary to the wild type nucleic acid top strand and the other is complimentary to the wild type nucleic acid bottom strand, to create a reaction mixture, wherein at least one of the probes overlaps a sequence on the target nucleic acid containing the suspected mutation; (b) subjecting the reaction mixture to a denaturing temperature to permit denaturation of the wild type nucleic acid and the target mutant nucleic acid; and (c) reducing the temperature to permit rapid hybridization of the probes to their corresponding sequences on the wild type and target mutant nucleic acids thereby forming complimentary wild type-probe duplexes on top and bottom strands, and partially complimentary target mutant-probe duplexes, wherein the DSN cleaves the complimentary wild type-probe duplexes and but not the partially complimentary target mutant-probe duplexes.

Figure 9:
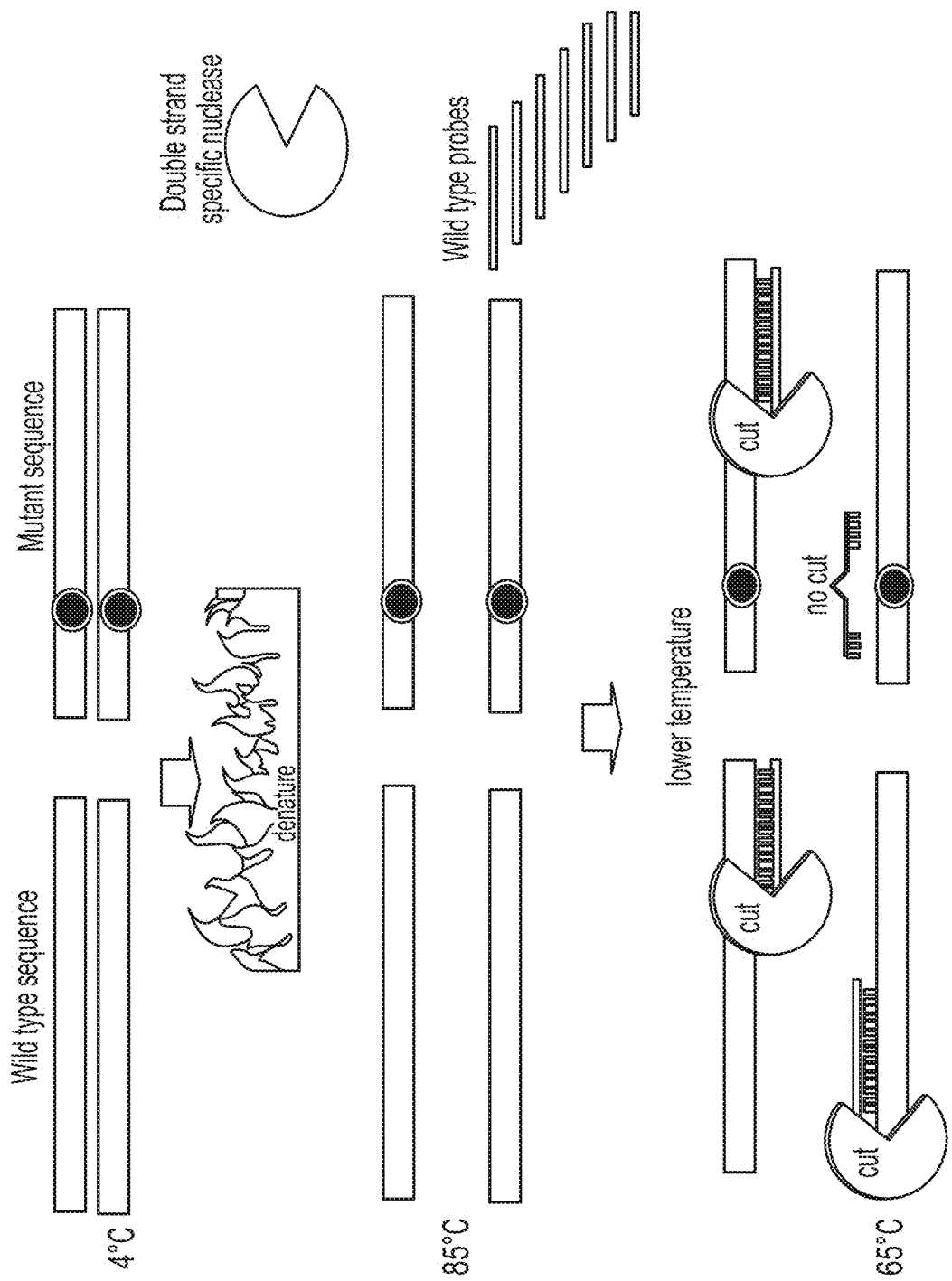
FIG. 9 is a schematic illustrating the 'nuclease chain reaction'. Wild-type degradation is combined with denaturation cycles during the DSN digestion process resulting in improved discrimination between mutant and WT and, therefore, better mutation enrichment. Note that, following brief denaturation at 85° C. and cooling to 65° C., the reaction cycles again at 85° C. before substantial re-hybridization of the two strands can occur.

More specifically, in some embodiments, NaME can be applied in a temperature cycling fashion, including successive brief denaturation cycles followed by DSN incubation in the presence of probes (FIG. 9). The thermostable DSN is included in the reaction mixture from the beginning despite the use of denaturing temperature. The temperature is raised such that it allows denaturation of the wild type nucleic acid and the target mutant nucleic acid without destroying the DSN enzyme which is simultaneously present in the reaction mixture. In some embodiments, this denaturing temperature is 65° C., 70° C., 75° C., 80° C., or 85° C.). In some embodiments, an organic solvent that can lower the Tm of the nucleic acids is included in the reaction mixture. The solvent lowers the Tm of the nucleic acids, without inhibiting the activity of DSN. Examples of such solvents include, but are not limited to DMSO, betaine or formamide. In some embodiments, 10-15% of DMSO is included in the reaction mixture.

After briefly denaturing the wild type and target nucleic acids, the temperature is lowered to permit hybridization of the probes to their corresponding sequences on the wild type and mutant nucleic acids. This hybridization temperature allows for DSN activity. In some embodiments, this hybridization temperature is 50° C., 55° C., 60° C., 65° C., or 70° C.). Since the oligonucleotide probes are in high excess as compared to the wild type and target nucleic acids, they bind to their corresponding sequences and form complimentary wild type-probe duplexes on top and bottom strands, and partially complimentary mutant-probe duplexes. The thermostable DSN then digests the wild type-probe complimentary duplexes, while the partially complimentary mutant-probe duplexes remain intact.

In some embodiments, steps (b) (denaturing step) and (c) (hybridization/DSN incubation step) are repeated for one or more cycles. In some embodiments, these steps are repeated for 1, 2, 3, 4, 5, 6, 7, 8, 9, 10, 20, 30, 40, or 50 cycles. The hybridization/DSN incubation step is only applied intermittently (for example, 2-4 min) and is interrupted by another denaturation cycle, followed by lowering the temperature again for DSN digestion, and so on. In this way it is possible to maximize the difference between wild type and mutant nucleic acid cleavage, while still preventing substantial re-hybridization of the two parent nucleic acid strands (which would lead to indiscriminate destruction of the nucleic acid, whether mutant or not).

In some embodiments, the method further comprises enriching the target mutant nucleic acid relative to the wild type nucleic acid by subjecting the reaction mixture with cleaved wild type-probe duplexes and uncleaved target mutant nucleic acids to an amplification condition such as but not limited to PCR, COLD-PCR, ligation mediated PCR or COLD-PCR using common ligated adaptors, multiplex PCR, and isothermal amplification (such as but not limited to displacement amplification based on phi-29 based; or Loop Mediated LAMP amplification; or any other isothermal mode of amplification).

In some embodiments, one of the probes overlaps a sequence on the top strand of the target nucleic acid containing the mutation, while the other probe overlaps a sequence on the bottom strand of the target nucleic acid containing the mutation and the two probes partially overlap each other.

In some embodiments, the method is used to prepare two or more different target mutant nucleic acids for subsequent enrichment relative to corresponding wild type nucleic acids and the method further comprises one or more additional pairs of probes directed to the different wild type nucleic acids, wherein for each pair of probes, one of the probes is complimentary to the wild type nucleic acid top strand and the other is complimentary to the wild type nucleic acid bottom strand.

NaME-PCR

Figure 10:
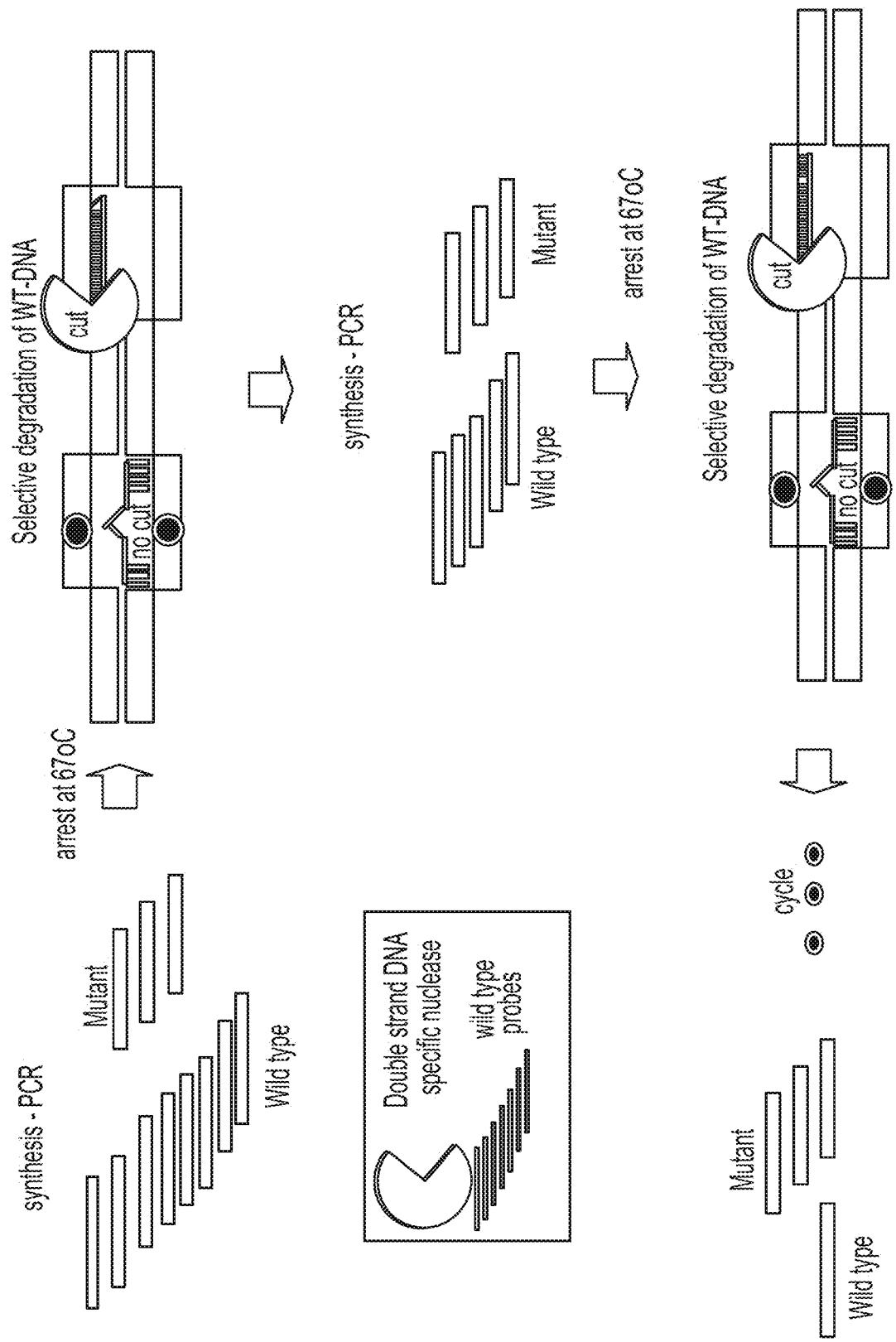
FIG. 10 is a schematic illustrating the PCR-NaME chain reaction where both PCR amplification and nuclease chain reaction operate simultaneously on the sample, in a single tube. The successive cycles of PCR synthesis and wild-type-specific degradation lead to improved enrichment of mutated sequences.

Some aspects of the present disclosure provide methods that combine the NaME process with PCR amplification in a single step as shown in FIG. 10. Accordingly, aspects of the disclosure provide a method for enriching a target mutant nucleic acid, the method comprising the steps of: (a) preparing an amplification reaction mixture comprising: a double-stranded wild type nucleic acid, a double-stranded target nucleic acid suspected of containing a mutation, a thermostable double strand-specific nuclease (DSN), a pair of oligonucleotide probes, one of which is complimentary to the wild type nucleic acid top strand and the other is complimentary to the wild type nucleic acid bottom strand, wherein at least one of the probes overlaps a sequence on the target nucleic acid containing the suspected mutation and PCR amplification components; (b) subjecting the reaction mixture to a denaturing temperature to permit denaturation of the wild type nucleic acid and the target mutant nucleic acid; (c) reducing the temperature to permit hybridization of the probes to their corresponding sequences on the wild type and target mutant nucleic acids thereby forming complimentary wild type-probe duplexes on top and bottom strands, and partially complimentary target mutant-probe duplexes, wherein the DSN cleaves the complimentary wild type-probe duplexes but not the partially complimentary target mutant-probe duplexes; and (d) subjecting the reaction mixture to an amplification condition thereby enriching the uncleaved target mutant nucleic acid relative to the cleaved wild type nucleic acid.

In this approach, NaME and PCR are performed in a single tube. All PCR components such as but not limited to primers, dNTPs, polymerase and polymerase buffer are included together with DSN and oligonucleotide probes in the reaction mixture. In this manner, the wild type nucleic acid is successively selectively destroyed by DSN while also re-synthesized by PCR, so that the total target DNA remains the same or increases, while at the same time continuously enriching the mutated DNA during the cycling process. In some embodiments, the method is performed in COLD-PCR format, instead of standard PCR.

DSN is compatible with most PCR buffers used commercially; hence DSN cleavage works in a PCR environment. Since both enzymes, DSN and polymerase, are thermostable it is possible to operate a combined reaction in a common thermocycler. The amplification condition applied in step (d) permits annealing of primer pairs to the wild type and target mutant nucleic acids followed by extension thereby enriching the target mutant nucleic acid relative to wild type.

In some embodiments, steps (b) (denaturing step) and (c) (hybridization/DSN incubation step) are repeated for two or more cycles before executing step (d) (PCR amplification). In some embodiments, these steps are repeated for 1, 2, 3, 4, 5, 6, 7, 8, 9, 10, 20, 30, 40, or 50 cycles. In some embodiments, steps (b) (denaturing step), (c) (hybridization/DSN incubation step) and (d)(amplification step) are repeated for two or more cycles. In some embodiments, these steps are repeated for 1, 2, 3, 4, 5, 6, 7, 8, 9, 10, 20, 30, 40, or 50 cycles.

In some embodiments, the reaction mixture further comprises an organic solvent that can lower the Tm of the nucleic acids is included in the reaction mixture. The solvent lowers the Tm of the nucleic acids, without inhibiting the activity of DSN. Examples of such solvents include, but are not limited to DMSO, betaine or formamide.

The denaturing temperature used is such that it allows denaturation of the wild type nucleic acid and the target mutant nucleic acid without destroying the DSN enzyme which is simultaneously present in the reaction mixture. In some embodiments, this denaturing temperature is 65° C., 70° C., 75° C., 80° C., or 85° C. applied for time periods of 1 sec, 30 sec, 1 min, 2 min, 3 min, 4 min, 5 min, 6 min, 7 min, 8 min, 9 min, or 10 min.

In some embodiments, one of the probes overlaps a sequence on the top strand of the target nucleic acid containing the mutation, while the other probe overlaps a sequence on the bottom strand of the target nucleic acid containing the mutation and the two probes partially overlap each other. In some embodiments, the probes are modified at the 3' end to prevent polymerase extension and to ensure that the probes do not act as primers during NaME-PCR. In some embodiments, the primers used for PCR amplification have a melting temperature that is below the temperature applied in step (c). This ensures that the primers do not bind to the nucleic acids during the time DSN is used to selectively cleave wild type nucleic acid. For example, the Tm of the primers can be 55° C. while the hybridization/DSN incubation step is performed above 65° C. where the primers do not interfere.

In some embodiments, the method is used to enrich two or more different target mutant nucleic acids relative to wild type nucleic acids and the method further comprises one or more additional pairs of probes directed to the different wild type nucleic acids, wherein for each pair of probes, one of the probes is complimentary to the wild type nucleic acid top strand and the other is complimentary to the wild type nucleic acid bottom strand.

FIG. 10 depicts a process of sequential DNA synthesis via PCR (during which DSN does not have enough time for substantial cleavage of the nucleic acids, while polymerase acts within seconds to synthesize templates) followed by arresting amplification for 10 min at 65° C. during which DSN acts selectively on wild type nucleic acid. At this temperature, primers do not bind, and hence polymerase synthesis does not proceed. This is then followed by more DNA synthesis via PCR and more DSN digestion and so on in a sequential process. The end product is DNA comprising mainly mutant DNA. The product can be directly sequenced or analyzed for mutations using other known methods.

Figure 11:
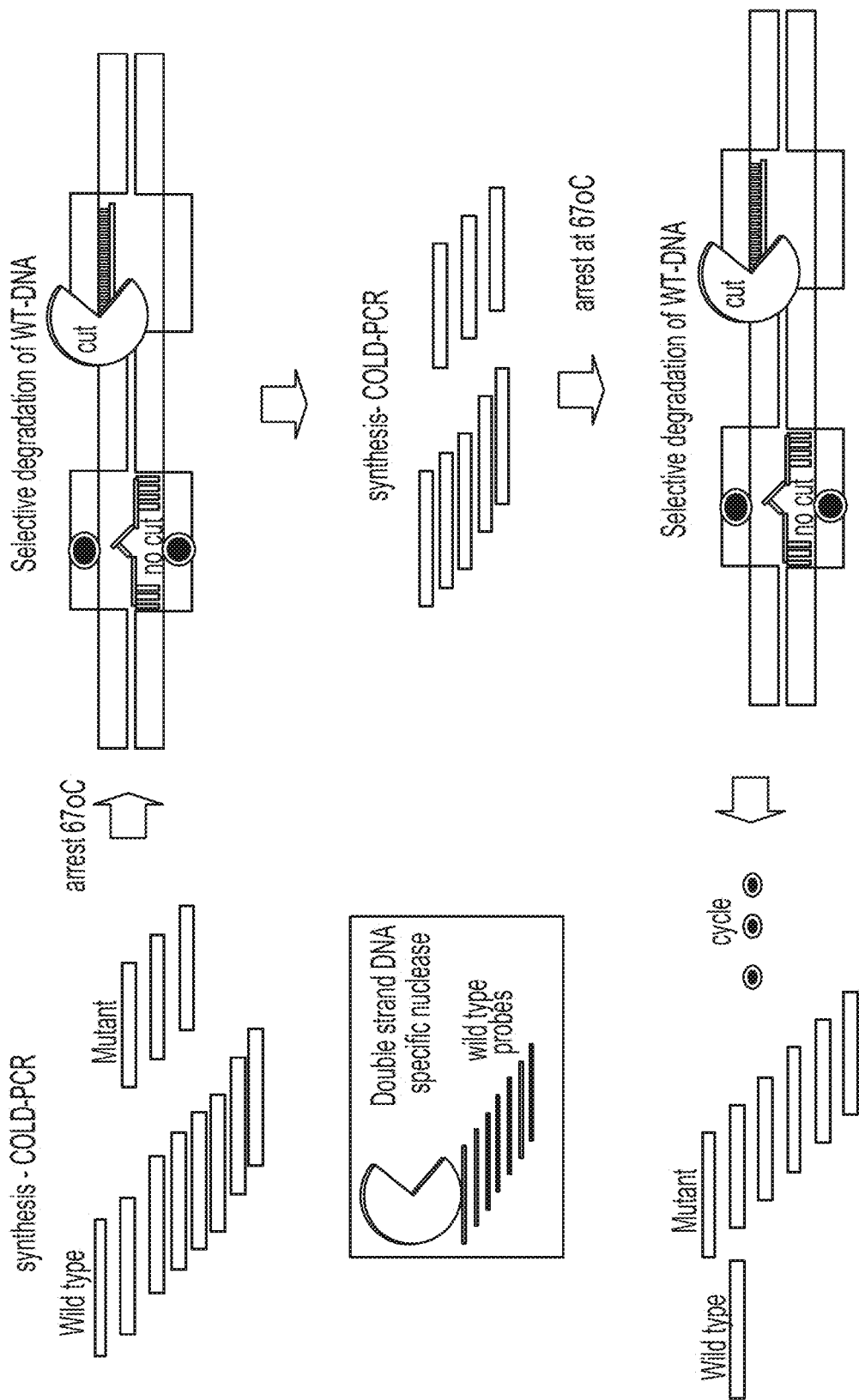
FIG. 11 is a schematic illustrating COLD-PCR-NaME. The successive cycles of mutant-specific synthesis and wild-type-specific degradation enrich for mutated sequences.

FIG. 11 depicts combination of NaME with COLD-PCR (COLD-NaME-PCR) for even greater enrichment of mutation containing nucleic acid. Conditions for COLD-PCR are applied that enable selective amplification of mutation containing nucleic acid during PCR, followed by selective cleavage of wild type nucleic acid using DSN in sequential single tube reactions. All types of COLD-PCR can be used, including but not limited to, full COLD, fast COLD, ICE-COLD PCR or Limited Denaturation Time LDT-COLD-PCR. Methods to perform COLD-PCR are highly compatible with NaME-PCR and have been described previously (see, for example, Li J, Wang L, Mamon H, Kulke M H, Berbeco R, Makrigiorgos G M. Nat Med 2008; 14:579-84; Milbury C A, Li J, Makrigiorgos G M. Nucleic Acids Res;

39:e2; Murphy D M, Castellanos-Rizaldos E, Makrigiorgos G M. Clin Chem. 2014 60:1014-6; the contents of which are incorporated by reference herein).

Methylation-Sensitive NaME—No Probes

Some aspects of the disclosure provide methods for preparing unmethylated or methylated nucleic acids of interest using temperature-based preferential enrichment of the alleles of interest on a genome wide level using enzymes such as DSN or exonuclease. In this approach, no probes need to be used. Genomic DNA is digested to smaller fragments. Following end repair and bisulfite-resistant adaptor ligation, bisulfite treatment is applied. Now the unmethylated sequences revert to a lower Tm in view of the C>T conversion, while methylated sequences remain at high Tm. Next, PCR is applied using the ligated adaptors, in order to generate amplified double stranded DNA library. (Alternatively one can apply PCR of repeat elements using primers specific for bisulfite-treated ALU, LINE 1 and other repeat elements spread over the genome, in order to apply the method to repeat sequences only; or arbitrarily-primed PCR (AP-PCR) to apply the method to large, arbitrary genomic fractions; or one can apply COLD-PCR. Isothermal forms of amplification may also be used in the place of PCR).

Following amplification, one may use either preferential denaturation approach, or a preferential hybridization approach to enrich unmethylated sequences. The two approaches are described below.

For preferential denaturation approach, the temperature is raised to a level of choice that generates partial or complete denaturation of lower Tm sequences. These include the originally unmethylated sequences which due to the C>U conversion resulted to a C>T conversion in the final PCR product, reverting to a lower Tm than the methylated sequences. High Tm sequences remain double stranded. These include the highly methylated GC-rich sequences. One of ordinary skill can determine the Tm of the sequences using methods known in the art and as described herein. The temperature used for this preferential denaturation of the low Tm sequences includes, but is not limited to 50° C., 55° C. 60° C. 66° C., 70° C., 75° C., 78° C., 80° C., or 85° C.). Next, DSN is added and the nucleic acids are exposed to conditions optimal for DSN activity. Conditions optimal for DSN activity include the most favorable conditions that allow the enzyme to work most efficiently for cleaving complimentary duplexes. The optimum DSN activity may be affected by conditions which include temperature; pH; and salt concentrations. In some embodiments, the temperature used for optimal for DSN activity includes, but not limited to 50° C., 55° C., 60° C., 65° C., or 70° C. The originally unmethylated sequences with lower Tm, (as well as naturally AT-rich sequences with lower Tm) will be denatured (i.e., will become single stranded) and therefore will escape DSN digestion, while the originally methylated sequences will be cleaved since they will remain in double stranded formation at the denaturation temperature chosen. A subsequent amplification of the remaining sequences using the ligated common adaptors will amplify preferentially the intact unmethylated sequences and will enable downstream massively parallel sequencing of unmethylated alleles. In some embodiments, the preferential denaturation of genomic DNA is performed in the presence of organic solvents that can lower the Tm of the nucleic acids. Examples include but are not limited to betaine, DMSO, or formamide. It is known that betaine generates a narrower melting peak for DNA duplexes, hence by adding betaine the discrimination between high and low Tm sequences at a given denaturation temperature will be 'sharper'.

Accordingly, in some embodiments, the method comprises the steps of: (a) ligating bisulfite-resistant adaptors to double stranded nucleic acids of interest; (b) subjecting the adaptor-linked nucleic acids to sodium bisulfite treatment and a nucleic acid amplification reaction to form double-stranded bisulfite-treated nucleic acids; (c) subjecting the bisulfite-treated nucleic acids to a temperature that permits preferential denaturation of unmethylated nucleic acids while methylated nucleic acids remain double-stranded; and (d) exposing the unmethylated and methylated nucleic acids to double strand-specific nuclease (DSN) and conditions for optimal DSN activity, wherein the DSN cleaves the methylated double-stranded nucleic acids but not the unmethylated single-stranded nucleic acids.

Alternatively, for preferential re-hybridization approach, a complete denaturation step is applied. The denaturing temperature should be sufficiently high so as to allow the full denaturation of the nucleic acids (e.g., 75° C., 80° C., 85° C., 90° C., or 95° C.). In some embodiments, the denaturing temperature is applied for 30 seconds, 1 min, 2 min, or 3 min. In some embodiments, the denaturing temperature of 95° C. is applied for 2 min. Following this, the temperature is lowered to a level that allows methylated (or other high Tm) sequences to re-hybridize rapidly (due to their higher Tm), while unmethylated sequences stay substantially single stranded. Next, application of DSN enzyme at conditions for optimal DSN activity digests preferentially the methylated duplexes. In some embodiments, the re-hybridization takes place in the presence of an organic solvent such as DMSO which lowers the Tm of the nucleic acid in combination with concurrent digestion using DSN (that is, instead of adding DSN in a later step). Use of organic solvents such as DMSO allows temperatures compatible with DSN action (e.g., 60-75° C.) to be applied during re-hybridization. Finally, a PCR amplification step can be applied to amplify preferentially the non-digested, unmethylated alleles followed by sequencing.

Accordingly, in some embodiments, the method comprises the steps of: (a) ligating bisulfite-resistant adaptors to double stranded nucleic acids of interest; (b) subjecting the adaptor-linked nucleic acids to sodium bisulfite treatment and a nucleic acid amplification reaction to form double-stranded bisulfite-treated nucleic acids; (c) subjecting the bisulfite-treated nucleic acids to a denaturing temperature that permits denaturation of both unmethylated and methylated nucleic acids to form unmethylated and methylated single stranded nucleic acids; (d) reducing the temperature to permit preferential formation of methylated duplexes, but not unmethylated duplexes; and (d) exposing the unmethylated and methylated nucleic acids to double strand-specific nuclease (DSN) and conditions for optimal DSN activity, wherein the DSN preferentially cleaves the methylated duplexes but not the unmethylated single-stranded nucleic acids.

Bisulfite conversion of DNA has formed the basis of identifying the methylation state of individual genes. With the advent of high throughput parallel sequencing methods, this technology has extended to the sequencing of libraries of bisulfite-treated DNA. The approach involves fragmenting DNA, ligating adaptors, bisulfite treatment and then amplifying the libraries for high throughput sequencing (see, for example, US 2013/0059734, US 2008/0254453, US 2009/0148842 and U.S. Pat. No. 8,440,404).

In a reverse approach that aims to enrich the methylated alleles, following preferential denaturation of the lower Tm sequences (which includes unmethylated alleles), treatment with any enzyme with selective action against single stranded (as opposed to double stranded) DNA such as but not limited to exonuclease I, or III is applied to remove the single stranded sequences. Subsequently, the remaining sequences (including the substantially methylated alleles) can be amplified and sequenced. Accordingly, in some embodiments, the method comprises the steps of: (a) ligating bisulfite-resistant adaptors to double stranded nucleic acids of interest; (b) subjecting the adaptor-linked nucleic acids to sodium bisulfite treatment and a nucleic acid amplification reaction to form double-stranded bisulfite-treated nucleic acids; (c) subjecting the bisulfite-treated nucleic acids to a temperature that permits preferential denaturation of unmethylated nucleic acids while methylated nucleic acids remain double-stranded; and (d) exposing the unmethylated and methylated nucleic acids to an exonuclease and conditions for optimal exonuclease activity, wherein the exonuclease cleaves the unmethylated single-stranded nucleic acids but not the methylated double-stranded nucleic acids.

In some embodiments, the method comprises the steps of: (a) ligating bisulfite-resistant adaptors to double stranded nucleic acids of interest; (b) subjecting the adaptor-linked nucleic acids to sodium bisulfite treatment and a nucleic acid amplification reaction to form double-stranded bisulfite-treated nucleic acids; (c) subjecting the bisulfite-treated nucleic acids to a denaturing temperature that permits denaturation of both unmethylated and methylated nucleic acids to form unmethylated and methylated single stranded nucleic acids; (d) reducing the temperature to permit preferential formation of methylated duplexes, but not unmethylated duplexes; and (d) exposing the unmethylated and methylated nucleic acids to an exonuclease and conditions for optimal exonuclease activity, wherein the exonuclease preferentially cleaves the unmethylated single-stranded nucleic acids, but not the methylated duplexes.

In some embodiments, the nucleic acid amplification reaction used to form double-stranded bisulfite-treated nucleic acids is selected from the group consisting of: PCR; full COLD-PCR, fast COLD-PCR; ice-COLD-PCR; temperature-tolerant COLD-PCR; LDT-COLD-PCR; AP-PCR; and repeat element PCR (ALU, LINE1, and other repeat sequences). In some embodiments, the resultant cleaved unmethylated single stranded nucleic acids and the uncleaved methylated duplexes are subjected to an amplification condition using the bisulfite resistant ligated adaptors. In some embodiments, the amplification condition is selected from the group consisting of: PCR; LDT-COLD-PCR; AP-PCR; and repeat element PCR (ALU, LINE1, and other repeat sequences).

Figure 15:
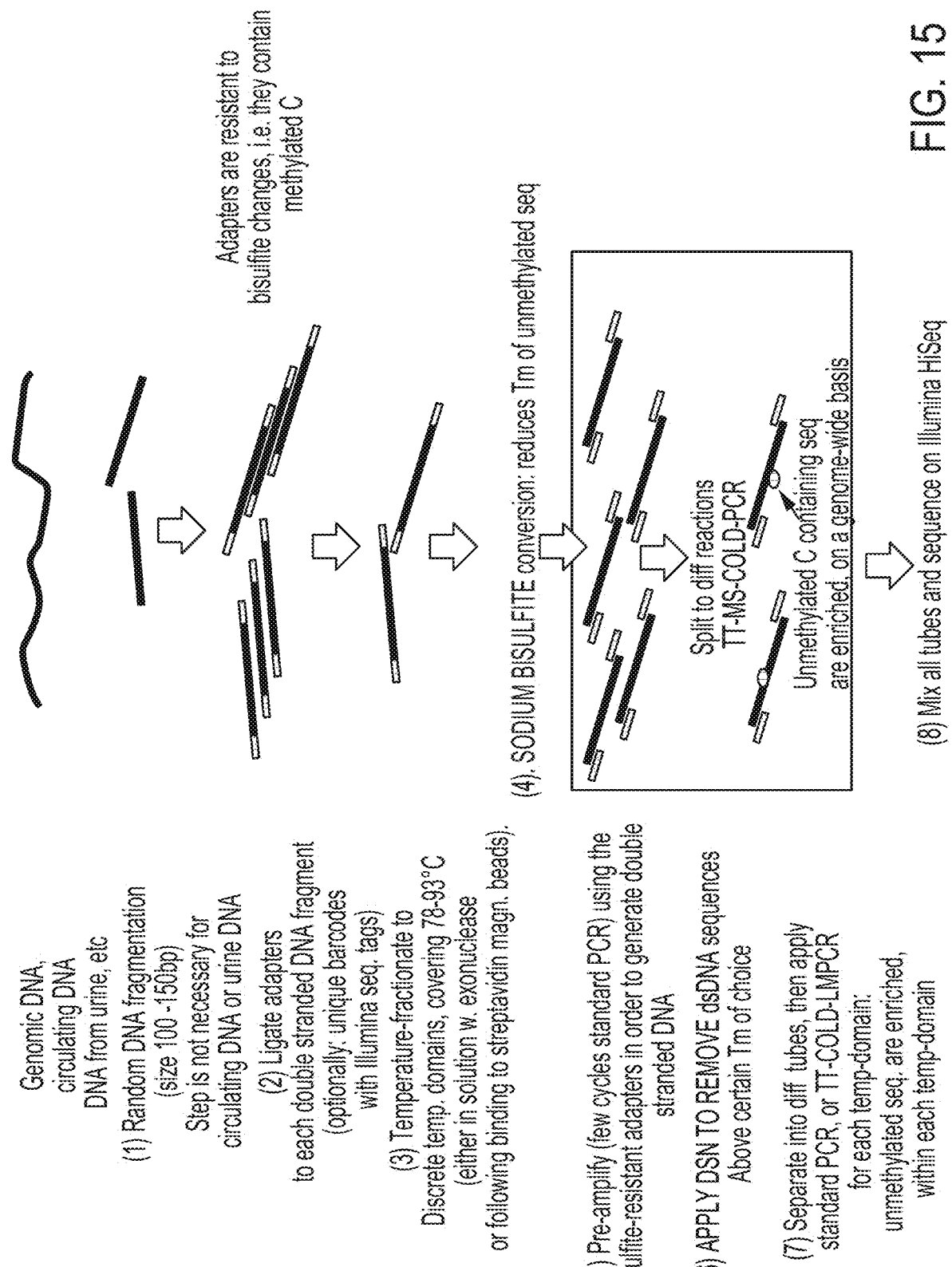
FIG. 15 shows the enrichment of unmethylated DNA sequences and methylation-sensitive temperature-tolerant-COLD-PCR following preferential DSN digestion of the sequences having a Tm higher than the Tm of choice. This scheme is a genome-wide application and does not require the use of gene-specific probes or selection of target sequences. The scheme enriches and amplifies hypo-methylated alleles on a genome-wide basis.

The specific advantage of performing the genome-wide amplification in COLD-PCR format is that, by employing a desired denaturation temperature during amplification, COLD-PCR provides an additional enrichment of lower-Tm sequences, as has been demonstrated previously by using COLD-PCR on unmethylated single gene sequences (Castellanos-Rizaldos, E., Milbury, C. A., Karatza, E., Chen, C.C., Makrigiorgos, G. M. and Merewood, A. (2014) COLD-PCR amplification of bisulfite-converted DNA allows the enrichment and sequencing of rare un-methylated genomic regions. PLoS One, 9, e94103.). Sequences with Tm above the selected denaturation temperature do not amplify during COLD-PCR. Any of the described COLD-PCR formats can be used to amplify selected fractions of un-methylated sequences from the genome (full COLD-PCR (11); fast COLD-PCR (11); ice-COLD-PCR (12); temperature-tolerant COLD-PCR (13); and limited denaturation time LDT-COLD-PCR, Murphy D M, Castellanos-Rizaldos E, Makrigiorgos G M. Clin Chem. 2014 60:1014-6). Each COLD-PCR format will achieve amplification of different genomic fractions. For example, fast COLD-PCR utilizes a single denaturation temperature, hence any sequence with Tm above this temperature will not be amplified at all. Alternatively, temperature tolerant COLD-PCR utilizes successive steps of increasing denaturation temperatures covering a broad range of temperatures (e.g. a range of 10° C. in 10 steps of 1° C. each), hence amplifying a broader range of unmethylated sequences from the genome. Depending on the application, different COLD-PCR programs can be employed. FIG. 15 describes the combination of DSN digestion of methylated sequences with tandem temperature tolerant COLD-PCR amplification of unmethylated sequences for further enrichment of globally unmethylated alleles.

In some embodiments of the methods used for preparing unmethylated or methylated nucleic acids of interest without using oligonucleotide probes, the naturally AT-rich sequences are removed prior to the sodium bisulfite treatment. Specifically, in the approaches described herein for preferential amplification of un-methylated DNA (or methylated DNA), a bisulfite step is applied that converts sequences that were originally at higher Tm (GC-rich sequences that are un-methylated) to lower Tm sequences (due to the C>T conversion). In contrast, methylated alleles retain their high Tm. In this way, a preferential denaturation step followed by DSN digestion and by subsequent amplification preferentially enriches the unmethylated alleles. However, during this amplification step, sequences with naturally low Tm will also be amplified irrespective of their methylation status (for example, AT-rich sequences). In some embodiments, such sequences with melting temperature (Tm) below a temperature of choice are removed to avoid these multiple 'normal, non-informative' sequences with low Tm to amplify in competition to the target sequences, thereby overwhelming the amplification of the sequences of interest.

Figure 16:
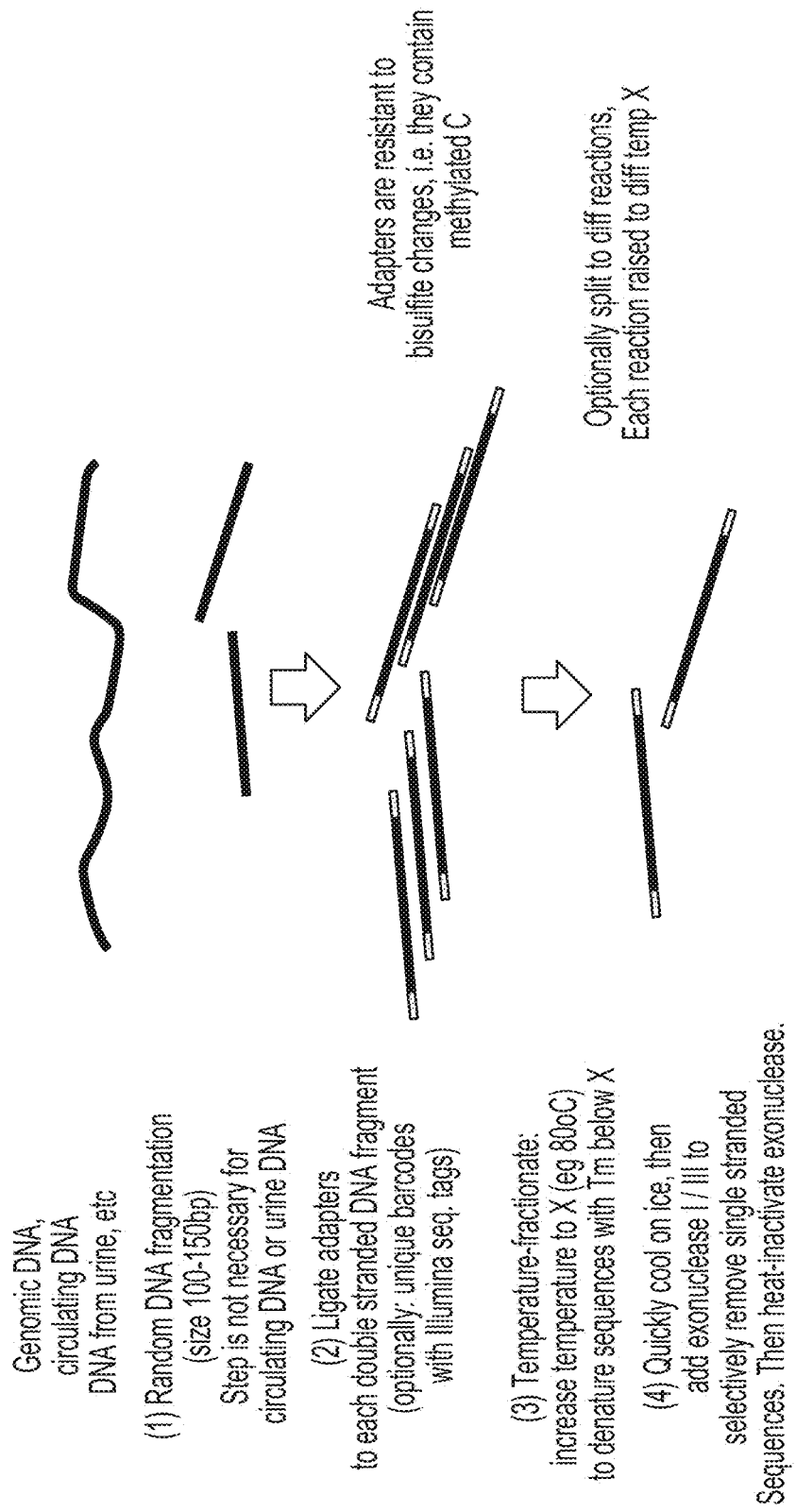
FIG. 16 depicts the process of using exonuclease-based temperature fractionation of DNA fragments to remove lower Tm fragments prior to bisulfite conversion.

Such 'non-informative' sequences can be substantially depleted from the sample before performing the bisulfite conversion step as follows:

(a) Removing lower-Tm sequences. A temperature-based fractionation of the starting material is performed just prior to sodium bisulfite treatment (FIG. 16). Following shearing of genomic DNA, the DNA is treated with an enzyme that creates blunt ends (e.g. 'end repair') such as but not limited to T7 DNA polymerase. Next, the temperature is raised to a desired cutoff temperature. This desired cut off temperature is the temperature at which sequences having a lower Tm need to be selectively removed. As an example, let it be assumed that the desired cut off temperature is 80° C. By raising the temperature to 80° C. for time periods of 1 sec-5 min (e.g., 1 sec, 5 secs, 15 secs, 30 secs, 45 secs, 1 min, 2 mins, 3 mins, 4, mins, or 5 mins), DNA fragments with Tm below 80° C. will be substantially denatured, while other fragments with Tm above 80° C. will remain substantially double stranded. Next, the temperature is quickly lowered, for example, by placing the sample on ice. Next, an enzyme that degrades preferentially single stranded DNA is added (for example, exonucleases I or III) and the temperature is raised to the optimal temperature for this enzyme activity (for example, 37° C.) for 1 min-60 min (e.g., 1 min, 5 mins, 10 mins, 20 mins, 30 mins, 40 mins, 45 mins, 50 mins, 55 mins, or 60 mins). Due to the complexity of genomic DNA, during this time period there is no substantial re-naturation of the single stranded fragments that undergo denaturation, and these become degraded by the enzyme. Finally, the exonuclease is heat inactivated. This process yields double stranded DNA fragments with Tm higher than about 80° C. In this way, fragments with Tm substantially lower than the chosen cutoff temperature are substantially depleted. In some embodiments, the process is repeated for additional rounds if more strict temperature fractionation is needed. The additional rounds can be at the same temperature (for example, 80° C.) or different temperatures (for example, 82-85° C.). Following removal of sequences with Tm below the desired cut off temperature, a sodium bisulfite step is applied to selectively convert C to U in unmethylated CpG positions in nucleic acids. Accordingly, these unmethylated DNA fragments will now revert to sequences with lower Tm. Because the majority of sequences with naturally lower Tm (for example, AT-rich sequences) has been removed during exonuclease-based temperature fractionation, it is now possible to remove higher Tm methylated sequences by preferential DSN digestion of double-stranded sequences, as well to amplify preferentially the unmethylated sequences via an amplification step such as PCR (or COLD-PCR) without interference of the lower Tm AT-rich sequences.

(b) Solid Support-Based Temperature Fractionation

Figure 17:
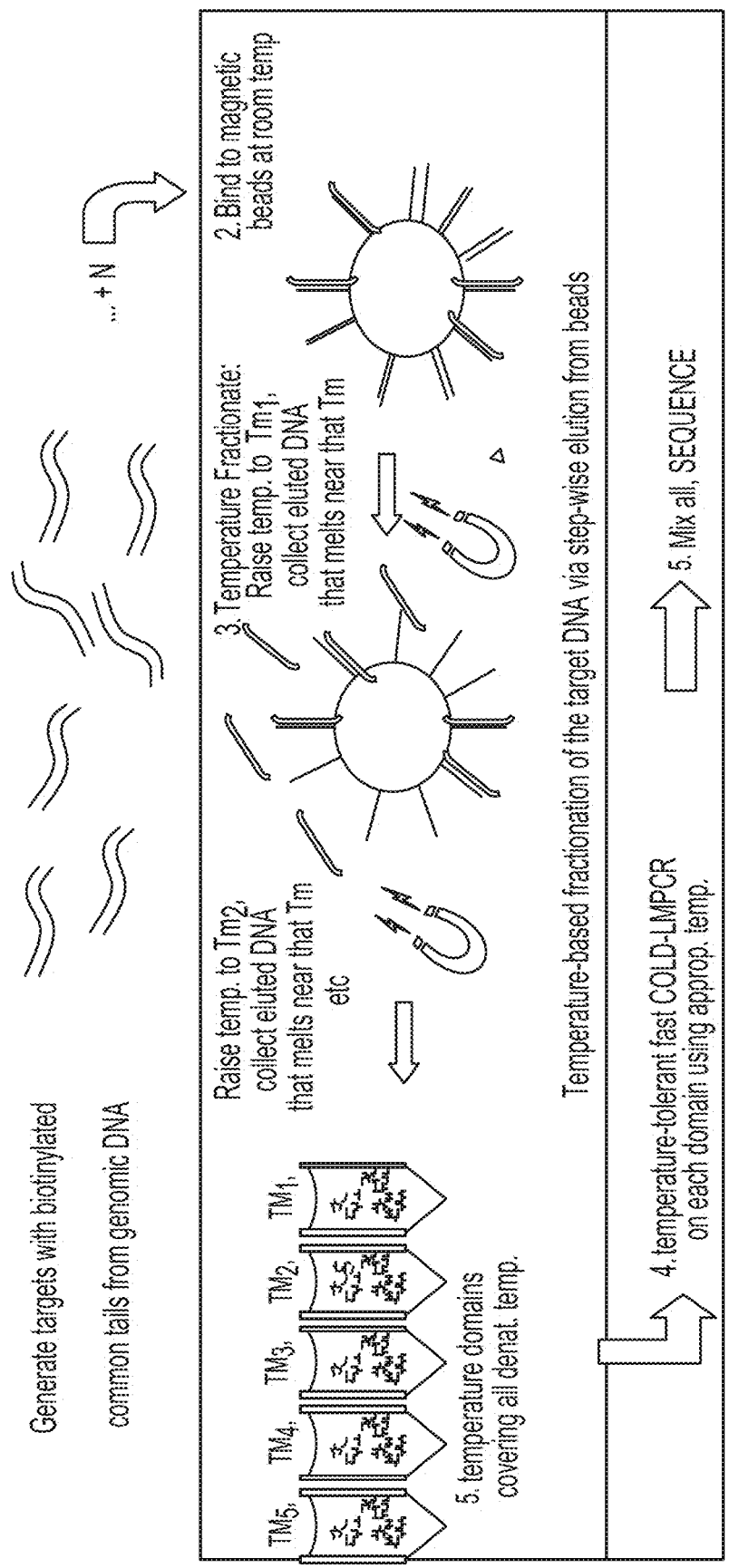
FIG. 17 is a flowchart showing the temperature-based elution of genomic DNA fragments by utilizing binding of DNA to magnetic beads.

Another approach for removing sequences with selected Tm from a genomic DNA sample includes solid support-based temperature fractionation. In some embodiments, the solid support comprises magnetic beads. Magnetic beads may be used for immobilization of the genomic DNA sample in order to enable separation of genomic DNA fragments into discrete temperature domains prior to further treatment (FIG. 17). After separating the genomic DNA fragments into discrete temperature domains, preferential amplification of unmethylated alleles can be applied separately within each domain, with minimal interference from amplification of non-desired lower Tm DNA fragments that do not provide any enrichment advantage. To apply this protocol, the ligation step depicted in FIG. 15 is performed with a mix of biotinylated and non-biotinylated bisulfite-resistant adaptors following which the majority of genomic DNA fragments are captured on streptavidin-coated magnetic beads from one strand only (the opposite strand remaining non-biotinylated). The conditions applied (total beads relative to total DNA) enable immobilization of several hundred nanograms of biotinylated DNA so that enough sequence copies are immobilized to retain low-level events in the fragment population. Following washing of unbound DNA, the temperature is ramped-up in 5 different consecutive steps differing by, for example, 3° C. During each step, the non-biotinylated DNA strands from lower-Tm fragments are gradually denaturing and are eluted in the supernatant which are then collected following bead magnetization (FIG. 17). DNA transitions from double stranded to mostly single stranded within an interval of ~4-5° C. By collecting the supernatant in temperature intervals of 3° C., the genomic DNA fragments are highly enriched (for example, 10-100-fold) in sequences within pre-defined temperature domains.

No DSN

Some aspects of the disclosure provide a method for preparing a target mutant nucleic acid for subsequent enrichment relative to a wild type nucleic acid comprising subjecting a nucleic acid sample comprising a double-stranded wild type nucleic acid and a double-stranded target nucleic acid suspected of containing a mutation to a condition that destabilizes the double stranded wild type and target mutant nucleic acids; contacting the destabilized double stranded wild type and target mutant nucleic acids with a pair of oligonucleotide probes, one of which is complimentary to the wild type nucleic acid top strand and the other is complimentary to the wild type nucleic acid bottom strand, to permit hybridization of the probes to their corresponding sequences on the wild type and target mutant nucleic acids thereby forming complimentary wild-type-probe duplexes on top and bottom strands, and partially complimentary target mutant-probe duplexes, wherein at least one of the probes overlaps a sequence on the target nucleic acid containing the suspected mutation, and wherein one or both probes comprise a locked nucleic acid (LNA), peptide nucleic acid (PNA), xeno nucleic acid (XNA), or a nucleic acid with any known modified base or RNA which is capable of blocking PCR amplification; and subjecting the complimentary wild-type-probe duplexes on top and bottom strands, and partially complimentary target mutant-probe duplexes to an amplification condition. The probes that overlap the mutation position act to block PCR amplification, e.g., acting as a clamp, for the wild-type top and bottom DNA strands, thereby inhibiting amplification of the wild-type nucleic acid. When the probe duplexes with a partially complimentary target mutant sequence, it is less able to inhibit PCR amplification, thereby permitting selective amplification of the mutant nucleic acid as compared to the wild-type, without a need for a cleaving enzyme (e.g., DSN).

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLE

NaME on Double-Stranded DNA

NaME utilizes nucleases (DNases) that have a substantially higher activity on double-stranded DNA (ds DNA) versus single-stranded DNA (ss DNA). Many DNases display such activity, including native shrimp dsDNase, recombinant shrimp dsDNase, King crab nuclease (DSN) and bovine DNase I. In the following sections, NaME embodiments for DSN thermostable nuclease are provided, but the same approaches can be used for all other nucleases that display substantially higher activity for ds DNA versus ss DNA. Thermostable nuclease (DSN) selectively degrades double stranded DNA (or DNA/RNA hybrids), while it has minimal or no action on single stranded DNA or RNA.

For the purposes of the present disclosure, the term "double-strand specific nuclease" or "DSN" includes DNA/RNA guided enzymes which have preferential activity on double-stranded DNA, as opposed to single stranded DNA. Examples of such enzymes that can be employed in conjunction with NaME include the RNA-guided Cas9 enzymes (Gu et al, *Depletion of Abundant Sequences by Hybridization (DASH): Using Cas9 to remove unwanted high-abundance species in sequencing libraries* and *molecular counting applications* Genome Biology 2016; 17, 41), or the Argonaute DNA-guided enzymes (Gao et al, *DNA-guided genome editing using the Natronobacterium gregoryi Argonaute*, Nature Biotechnology May 2016 advanced online publication). These DNA/RNA guided enzymes digest DNA with high preference when the probe ('guide oligonucleotide') is fully matched to the target DNA, and less so when there is a mismatch. By employing probes targeting both top and bottom DNA strands in an overlapping fashion as described in the present invention, NAME can be applied with DNA/RNA guided enzymes, in the same manner as when using other DSN nucleases described herein.

NaME takes advantage of the DSN properties to degrade specific sequences from both the top and bottom DNA strands of wild-type (WT) DNA (FIG. 1A). In contrast, mutation-containing DNA is not degraded or degraded much less than the WT DNA. Hence, a subsequent PCR reaction after DSN digestion specifically amplifies the mutant alleles that remain substantially intact.

An example of the application of this approach is demonstrated in FIG. 1B: a 114 bp ds KRAS PCR amplicon with a 5% mutation was subjected to the process of FIG. 1A. The DNA template used consisted of the KRAS PCR amplicon with a 5% mutation (1:1000, 1:10,000 (approximately 0.001 nM), and 1:100,000) and wtDAN-Taqman-probe (500 nM) and with or without KRAS-cutter (500 nM). The samples were then either incubated with DSN (1U) or without DSN. For the 1:1000 and 1:100,000 samples, the mixture was heated to 67° C. for 10 minutes and then 94° for 2 minutes. For the 1:10,000 samples, the mixture was heated to a selected temperature (63° C., 67° C., 70° C., or 73° C.) for 10 minutes, and then heated to 94° C. for two minutes. By comparing the mutation abundance in parallel reactions without DSN versus reactions with DSN, the data in FIG. 1B and Table 1 demonstrate mutation enrichments of about 10-fold for temperatures 63-67° C.

TABLE 1

KRAS Mutation Abundance at Different Temperatures

| Sample ID | Delta Ct | Final mutation abundance | Enrichment-fold |
|---|---|---|---|
| 1-10k-NO-DSN | 0 | 4.14 | 1.0 (untreated) |
| 1-10k-1U-63C | 9.07 | 38.6 | 9.3 |
| 1-10k-1U-67C | 8.58 | 37.4 | 9.0 |
| 1-10k-1U-70C | 6.54 | 14 | 3.4 |
| 1-10k-1U-73C | 7.11 | 19.5 | 4.7 |
| 1-10k-1U-67C-no-cutter | 5.75 | 6.07 | 1.5 |

NaME Applied Directly from Genomic DNA

FIGS. 5-7 demonstrate NaME applied directly to genomic DNA for a single KRAS target sequence, or single p53 sequence (FIG. 5), two targets simultaneously, duplex KRAS and p53 (FIG. 6) and three different KRAS mutations in a single-target reaction (FIG. 7A). In FIG. 5, genomic DNA with approximately a 0.5% KRAS mutation, or a p53 mutation in a separate reaction was denatured at 95° C. and incubated at 65° C. for 20 minutes in the presence of overlapping blocked probes and DSN. The enrichment of the KRAS or p53 mutations were detected via a subsequent digital PCR that quantifies the mutation abundance. In FIG. 6, the genomic DNA underwent the same protocol as in FIG. 5, except that the KRAS and p53 mutated genomic DNA were mixed in a single tube. Genomic DNA from the SW480 cell line containing both KRAS and p53 mutations was mixed with wild-type DNA to create low-abundance mutations on both genes. Two mutation percentage were tested: approximately 5% and approximately 0.3%. In FIG. 7A, genomic DNA with 1-5% KRAS mutations from three different cell lines, in separate reactions, underwent the same protocol as described above. In FIG. 7B, the DNA was denatured, the temperature was reduced to 67° C., DSN and overlapping probes were added for a 20 minute incubation. The DSN was inactivated, and PCR and digital PCR were performed on each target amplicon to derive their respective mutational abundances. All mutations are enriched simultaneously via NaME. FIG. 7B depicts mutation enrichment when NaME is applied on 11 targets simultaneously, directly from genomic DNA obtained from Horizon Dx, containing known low level mutations on the respective targets. It is demonstrated that all 11 targets are enriched simultaneously following application of NaME directly to genomic DNA.

Mutation Scanning Using NaME

FIGS. 12B and 12C depict the results when using NaME for mutation enrichment of a 40-80 bp region in TP53 exon 8. All of the 4 mutations tested are enriched via NaME. In FIG. 12B, mutation-containing DNA from the PFSK or HCC cell lines was serially diluted into WT DNA, and then a first PCR was applied to amplify the target of interest (tp53). The amplicon was denatured and then incubated at 65° C. in the presence of probes and DSN. The two probes correspond to the WT top and bottom strands, respective. The presence of a mutation inhibits DSN digestion, hence the mutated DNA is amplified during rounds of PCR. The effects of probe length and concentration on mutation enrichment are also depicted in FIG. 12B. In FIG. 12C, mutation-containing DNA from PFSK, HCC, SW480, and MDAMB cell lines, all of which have different mutations on p53 exon 8, were serially diluted into WT DNA, and then the same protocol as described in FIG. 12B was performed. The mutation enrichment-fold was calculated by performing digital PCR both before and after NaME application.

REFERENCES

1. Thomas, R. K., Baker, A. C., Debiasi, R. M., Winckler, W., Laframboise, T., Lin, W. M., Wang, M., Feng, W., Zander, T., Macconnaill, L. E. et al. (2007) High-throughput oncogene mutation profiling in human cancer. *Nat Genet*, 39, 347-351.
2. Chou, L. S., Lyon, E. and Wittwer, C. T. (2005) A comparison of high-resolution melting analysis with denaturing high-performance liquid chromatography for mutation scanning: cystic fibrosis transmembrane conductance regulator gene as a model. Am J Clin Pathol, 124, 330-338.
3. Thomas, R. K., Nickerson, E., Simons, J. F., Janne, P. A., Tengs, T., Yuza, Y., Garraway, L. A., Laframboise, T., Lee, J. C., Shah, K. et al. (2006) Sensitive mutation detection in heterogeneous cancer specimens by massively parallel picoliter reactor sequencing. Nat Med, 12, 852-855.
4. Paez, J. G., Janne, P. A., Lee, J. C., Tracy, S., Greulich, H., Gabriel, S., Herman, P., Kaye, F. J., Lindeman, N., Boggon, T. J. et al. (2004) EGFR Mutations in Lung Cancer: Correlation with Clinical Response to Gefitinib Therapy. *Science*, 304, 1497-1500.
5. Janne, P.A., Borras, A.M., Kuang, Y., Rogers, A.M., Joshi, V.A., Liyanage, H., Lindeman, N., Lee, J.C., Halmos, B., Maher, E. A. et al. (2006) A rapid and sensitive enzymatic method for epidermal growth factor receptor mutation screening. *Clin Cancer Res*, 12, 751-758.
6. Engelman, J. A., Mukohara, T., Zejnullahu, K., Lifshits, E., Borras, A. M., Gale, C. M., Naumov, G. N., Yeap, B. Y., Jarrell, E., Sun, J. et al. (2006) Allelic dilution obscures detection of a biologically significant resistance mutation in EGFR-amplified lung cancer. The Journal of clinical investigation.
7. Diehl, F., Li, M., Dressman, D., He, Y., Shen, D., Szabo, S., Diaz, L. A., Jr., Goodman, S. N., David, K. A., Juhl, H. et al. (2005) Detection and quantification of mutations in the plasma of patients with colorectal tumors. *Proc Natl Acad Sci USA*, 102, 16368-16373.

8. Kimura, T., Holland, W. S., Kawaguchi, T., Williamson, S. K., Chansky, K., Crowley, J. J., Doroshow, J. H., Lenz, H. J., Gandara, D. R. and Gumerlock, P. H. (2004) Mutant DNA in plasma of lung cancer patients: potential for monitoring response to therapy. *Annals of the New York Academy of Sciences,* 1022, 55-60.
9. Nilsen, I. W., Overbo, K., Jensen Havdalen, L., Elde, M., Gjellesvik, D. R. and Lanes, O. (2010) The enzyme and the cDNA sequence of a thermolabile and double-strand specific DNase from Northern shrimps (*Pandalus borealis*). *PLoS One,* 5, e10295.
10. Castellanos-Rizaldos, E., Milbury, C.A., Karatza, E., Chen, C.C., Makrigiorgos, G. M. and Merewood, A. (2014) COLD-PCR amplification of bisulfite-converted DNA allows the enrichment and sequencing of rare unmethylated genomic regions. *PLoS One,* 9, e94103.
11. Li, J., Wang, L., Mamon, H., Kulke, M. H., Berbeco, R. and Makrigiorgos, G. M. (2008) Replacing PCR with COLD-PCR enriches variant DNA sequences and redefines the sensitivity of genetic testing. *Nat Med,* 14, 579-584.
12. Milbury, C. A., Li, J. and Makrigiorgos, G. M. (2011) Ice-COLD-PCR enables rapid amplification and robust enrichment for low-abundance unknown DNA mutations. *Nucleic Acids Res,* 39, e2.
13. Castellanos-Rizaldos, E., Liu, P., Milbury, C.A., Guha, M., Brisci, A., Cremonesi, L., Ferrari, M., Mamon, H. and Makrigiorgos, G. M. (2012) Temperature-Tolerant COLD-PCR Reduces Temperature Stringency and Enables Robust Mutation Enrichment. *Clin Chem,* 58, 1130-1138.
14. Shagin, D. A., Rebrikov, D. V., Kozhemyako, V. B., Altshuler, I. M., Shcheglov, A. S., Zhulidov, P. A., Bogdanova, E. A., Staroverov, D. B., Rasskazov, V. A. and Lukyanov, S. (2002) A novel method for SNP detection using a new duplex-specific nuclease from crab hepatopancreas. *Genome Res,* 12, 1935-1942.
15. Qiu, X., Zhang, H., Yu, H., Jiang, T. and Luo, Y. (2015) Duplex-specific nuclease-mediated bioanalysis. *Trends in biotechnology,* 33, 180-188.

We claim:

1. A method for preparing a target mutant nucleic acid for subsequent enrichment relative to a wild type nucleic acid comprising
    subjecting a nucleic acid sample comprising a double-stranded wild type nucleic acid and a double-stranded target nucleic acid suspected of containing a mutation to a condition that destabilizes the double stranded wild type and target mutant nucleic acids;
    contacting the destabilized double stranded wild type and target mutant nucleic acids with a pair of oligonucleotide probes, one of which is complementary to the wild type nucleic acid top strand and the other is complementary to the wild type nucleic acid bottom strand, to permit hybridization of the probes to their corresponding sequences on the wild type and target mutant nucleic acids thereby forming complementary wild-type-probe duplexes on top and bottom strands, and partially complementary target mutant-probe duplexes, wherein at least one of the probes overlaps the suspected mutation; and
    exposing the complementary wild-type-probe duplexes and the partially complementary target mutant-probe duplexes to a double strand-specific nuclease (DSN), wherein the DSN preferentially cleaves the complementary wild type-probe duplexes relative to the partially complementary target mutant-probe duplexes.

2. The method of claim 1, wherein the condition that destabilizes the double stranded wild type and mutant nucleic acids to permit hybridization of the probes to their corresponding sequences on the wild type and mutant nucleic acids comprises addition of an organic solvent and/or an increase in temperature combined with a thermostable DSN.

3. The method of claim 1, wherein both probes overlap the suspected mutation.

4. The method of claim 1, wherein the method is used to prepare an unmethylated target nucleic acid of interest for subsequent enrichment, and wherein the nucleic acid sample is first treated with sodium bisulfite and one of the oligonucleotide probes is complementary to the top strand of the methylated nucleic acid of interest, while the other oligonucleotide probe is complementary to the bottom strand of the methylated nucleic acid of interest, and wherein the probe that overlaps the suspected mutation is complementary to the methylated nucleic acid of interest.

5. The method of claim 1, wherein the method is used to prepare a methylated target nucleic acid of interest for subsequent enrichment, and wherein the nucleic acid sample is first treated with sodium bisulfite and one of the oligonucleotide probes is complementary to the top strand of the bisulfite converted unmethylated nucleic acid of interest, while the other oligonucleotide probe is complementary to the bottom strand of the bisulfite converted unmethylated nucleic acid of interest, and wherein the probe that overlaps the suspected mutation is complementary to the bisulfite converted unmethylated nucleic acid of interest.

6. The method of claim 1, wherein the method is used to prepare both an unmethylated target nucleic acid of interest and a methylated target nucleic acid of interest for subsequent enrichment, wherein the nucleic acid sample is first treated with sodium bisulfite, and wherein two pairs of oligonucleotide probes are used comprising:
    (i) a pair of oligonucleotide probes, one of which is complementary to the top strand of the methylated form of the unmethylated target nucleic acid of interest, while the other is complementary to the bottom strand of the methylated form of the unmethylated target nucleic acid of interest, and wherein the probe that overlaps the suspected mutation binds to the strand containing the unmethylated nucleic acid; and
    (ii) a pair of oligonucleotide probes, one of which is complementary to the top strand of the bisulfite converted unmethylated form of the methylated target nucleic acid of interest, while the other is complementary to the bottom strand of the bisulfite converted unmethylated form of the methylated target nucleic acid of interest, and wherein the probe that overlaps the suspected mutation binds to the strand containing the methylated nucleic acid.

7. A method for preparing a target mutant nucleic acid for subsequent enrichment relative to a wild type nucleic acid comprising
    exposing a nucleic acid sample comprising a double-stranded wild type nucleic acid and a double-stranded target nucleic acid suspected of containing a mutation to a double strand-specific nuclease (DSN) and a pair of oligonucleotide probes, one of which is complementary to the wild type nucleic acid top strand and the other is complementary to the wild type nucleic acid bottom strand, to create a reaction mixture, wherein at least one of the probes overlaps the suspected mutation; and
    subjecting the reaction mixture to a condition that destabilizes the double stranded wild type and target mutant nucleic acids to permit hybridization of the probes to their corresponding sequences on the wild type and target mutant nucleic acids thereby forming complementary wild-type-probe duplexes on top and bottom strands, and partially complementary target mutant-probe duplexes, wherein the DSN preferentially cleaves the complementary wild type-probe duplexes relative to the partially complementary target mutant-probe duplexes.

8. The method of claim 7, wherein the condition that destabilizes the double stranded wild type and mutant nucleic acids to permit hybridization of the probes to their corresponding sequences on the wild type and mutant nucleic acids comprises addition of an organic solvent and/or an increase in temperature combined with a thermostable DSN.

9. The method of claim 7, wherein both probes overlap the suspected mutation.

10. The method of claim 7, wherein the method is used to prepare an unmethylated target nucleic acid of interest for subsequent enrichment, and wherein the nucleic acid sample is first treated with sodium bisulfite and one of the oligonucleotide probes is complementary to the top strand of the methylated nucleic acid of interest, while the other oligonucleotide probe is complementary to the bottom strand of the methylated nucleic acid of interest, and wherein the probe that overlaps the suspected mutation is complementary to the methylated nucleic acid of interest.

11. The method of claim 7, wherein the method is used to prepare a methylated target nucleic acid of interest for subsequent enrichment, and wherein the nucleic acid sample is first treated with sodium bisulfite and one of the oligonucleotide probes is complementary to the top strand of the bisulfite converted unmethylated nucleic acid of interest, while the other oligonucleotide probe is complementary to the bottom strand of the bisulfite converted unmethylated nucleic acid of interest, and wherein the probe that overlaps the suspected mutation is complementary to the bisulfite converted unmethylated nucleic acid of interest.

12. A method for preparing a target mutant nucleic acid for subsequent enrichment relative to a wild type nucleic acid, the method comprising the steps of:
(a) exposing a nucleic acid sample comprising a double-stranded wild type nucleic acid and a double-stranded target nucleic acid suspected of containing a mutation to a thermostable double strand-specific nuclease (DSN), an organic solvent that lowers the melting temperature of the double-stranded target nucleic acid, and a pair of oligonucleotide probes, one of which is complementary to the wild type nucleic acid top strand and the other is complementary to the wild type nucleic acid bottom strand, to create a reaction mixture, wherein at least one of the probes overlaps the suspected mutation;
(b) subjecting the reaction mixture to a denaturing temperature to permit denaturation of the wild type nucleic acid and the target mutant nucleic acid; and
(c) reducing the temperature to permit hybridization of the probes to their corresponding sequences on the wild type and target mutant nucleic acids thereby forming complementary wild type-probe duplexes on top and bottom strands, and partially complementary target mutant-probe duplexes, wherein the DSN preferentially cleaves the complementary wild type-probe duplexes relative to the partially complementary target mutant-probe duplexes.

13. The method of claim 12, wherein the denaturing temperature is 65° C. to 85° C.

14. The method of claim 12, wherein both probes overlap the suspected mutation.

15. The method of claim 12, wherein the probes only partially overlap each other.

16. The method of claim 12, further comprising repeating steps (b) and (c) for two or more cycles.

17. A method for preparing a target mutant nucleic acid for subsequent enrichment relative to a wild type nucleic acid comprising
exposing a nucleic acid sample comprising a double-stranded wild type nucleic acid and a double-stranded target nucleic acid suspected of containing a mutation to a pair of oligonucleotide probes, one of which is complementary to the wild type nucleic acid top strand and the other is complementary to the wild type nucleic acid bottom strand, to create a reaction mixture, wherein at least one of the probes overlaps the suspected mutation and the two probes only partially overlap each other;
subjecting the reaction mixture to a denaturing temperature to permit denaturation of the wild type nucleic acid and the target mutant nucleic acid;
reducing the temperature of the reaction mixture to permit formation of complementary wild type-probe duplexes on the top and bottom strands and partially complementary target mutant-probe duplexes; and
exposing the reaction mixture to a double strand-specific nuclease (DSN),
wherein the DSN preferentially cleaves the complementary wild type-probe duplexes relative to the partially complementary target mutant-probe duplexes.

18. The method of claim 17, wherein both probes overlap the suspected mutation.

19. The method of claim 17, wherein the method is used to prepare an unmethylated target nucleic acid of interest for subsequent enrichment, and wherein the nucleic acid sample is first treated with sodium bisulfite and one of the oligonucleotide probes is complementary to the top strand of the methylated nucleic acid of interest, while the other oligonucleotide probe is complementary to the bottom strand of the methylated nucleic acid of interest, and wherein the probe that overlaps the suspected mutation is complementary to the methylated nucleic acid of interest.

20. The method of claim 17, wherein the method is used to prepare a methylated target nucleic acid of interest for subsequent enrichment, and wherein the nucleic acid sample is first treated with sodium bisulfite and one of the oligonucleotide probes is complementary to the top strand of the bisulfite converted unmethylated nucleic acid of interest, while the other oligonucleotide probe is complementary to the bottom strand of the bisulfite converted unmethylated nucleic acid of interest, and wherein the probe that overlaps the suspected mutation is complementary to the bisulfite converted unmethylated nucleic acid of interest.

* * * * *